United States Patent
Wahren et al.

(10) Patent No.: US 7,855,177 B1
(45) Date of Patent: Dec. 21, 2010

(54) METHODS AND KITS FOR PREVENTING HYPOGLYCEMIA

(75) Inventors: John Wahren, Djursholm (SE); Karin Ekberg, Tyreso (SE); James Callaway, San Diego, CA (US)

(73) Assignee: Cebix Inc., LaJolla, CA (US)

( * ) Notice: Subject to any disclaimer, the term of this patent is extended or adjusted under 35 U.S.C. 154(b) by 0 days.

(21) Appl. No.: 12/796,149

(22) Filed: Jun. 8, 2010

Related U.S. Application Data

(60) Provisional application No. 61/255,560, filed on Oct. 28, 2009.

(51) Int. Cl.
- A61K 38/28 (2006.01)
- A61K 38/00 (2006.01)
- A61K 38/02 (2006.01)

(52) U.S. Cl. .......................... 514/5.9; 514/1.1; 514/6.7; 514/6.8; 514/6.9

(58) Field of Classification Search ........................ None
See application file for complete search history.

(56) References Cited

U.S. PATENT DOCUMENTS

| | | | |
|---|---|---|---|
| 4,608,364 | A | 8/1986 | Grau et al. |
| 4,652,548 | A | 3/1987 | Chance et al. |
| 7,323,543 | B2 | 1/2008 | Van Antwerp et al. |

FOREIGN PATENT DOCUMENTS

| | | |
|---|---|---|
| WO | 2007015069 | 2/2007 |
| WO | 2008118387 | 3/2008 |
| WO | 2009068911 | 6/2009 |

OTHER PUBLICATIONS

Kamikawa, A., et al, Proinsulin C-Peptide abrogates type-1 diabetes-induced increase of renal endothelial nitric oxide synthase in rats, Diabetes Metab Res Rev, 2008, 24(4), 331-8.

Hills, CE, Intracellular signaling by C-peptide, Exp Diab Res, 2008, Article ID 635158.

Nordquist, L,, Proinsulin C-peptide: Friend or foe in the development of diabetes-associated complications?, Vasc Health Risk Man, 2008, 4(6), 1283-1288.

Ekberg, K, C-Peptide replacement therapy and sensory nerve function in type 1 diabetic neuropathy, J. Diabetes Care. 2007, 30(1), 71-6.

Zhang, W, C-peptide improves neuropathy in type 1 diabetic BB/Wor-rats, Diabetes Metab Res Rev. 2007, 23(1), 63-70.

Vish, MG, Proinsulin c-peptide exerts beneficial effects in endotoxic shock in mice, Crit Care Med. 2007, 35 (5):1348-55.

Kamiya, H, et al, C-peptide reverses nociceptive neuropathy in Type I diabetes, Diabetes. 2006, 55, 3581-3587.

Shafqat, J, et al, Proinsulin C-peptide elicits disaggregation of insulin resulting in enhanced physiological insulin effects, Cell Mol Life Sci. 2006, 63 (15):1805-11.

Rebsomen, L, et al, C-peptide replacement improves weight gain and renal function in diabetic rats, Diabetes Metab. 2006, 32 (3), 223-8.

Wahren, J, et al, C-peptide: new findings and therapeutic implications in diabetes, Clin Physiol Funct Imaging, 2004, 24, 180-189.

Sato, Y, et al, C-peptide fragments stimulate glucose utilization in diabetic rats, Cell Mol Life Sci. 2004, 61(6), 727-32.

Johansson, BL, et al, C-peptide improves adenosine-induced myocardial vasodilation in type 1 diabetes patients, J Physiol Endocrinol Metab, 2004, 286(1), E14-9.

Wahren, J, et al, Biological Effects of C-peptide and Proinsulin, Int. Textbook of Diabetes Mellitus, Third Edition, 2004.

Wahren, J, et al, C-peptide makes a comeback, Diab Met Res. 2003, 19, 345-347.

Cotter, MA, et al, Effects of proinsulin C-peptide in experimental diabetic neuropathy: vascular actions and modulation by nitric oxide synthase inhibition, Diabetes. 2003, 52(7), 1812-7.

Ekberg, K, et al, Amelioration of sensory nerve dysfunction by C-Peptide in patients with type 1 diabetes, J. Diabetes. Feb. 2003;52(2), 536-41.

Hansen, A, C-peptide exerts beneficial effects on myocardial blood flow and function in patients with type 1 diabetes, Diabetes. Oct. 2002;51(10), 3077-82.

Forst, T, et al, Effect of C-peptide on glucose metabolism in patients with type 1 diabetes, Effect of C-peptide on glucose metabolism in patients with type 1 diabetes, Diabetes Care. 2002, 25(6), 1096-7.

Fernqvist-Forbes, E, et al, Effects of C-peptide on forearm blood flow and brachial artery dilatation in patients with type 1 diabetes mellitus, Acta Physiol Scand. 2001, 172(3), 159-65.

Zhang, W, et al, Human C-peptide dose dependently prevents early neuropathy in the BB/Wor-rat, Int. J. Exp. Diabetes. Res. 2001, 2(3), 187-93.

Sima, AA, et al, Proinsulin C-peptide—A consensus statement, Int J Exp Diab Res. 2001, 2, 145-151.

Grunberger, G, et al, Molecular basis for the insulinomimetic effects of C-peptide, Diabetologia. 2001, 44, 1247-1257.

Sima, AA, et al, C-peptide prevents and improves chronic Type I diabetic polyneuropathy in the BB/Wor rat, Diabetologia, 2001, 44(7), 889-97.

Johansson, BL, et al, Beneficial effects of C-peptide on incipient nephropathy and neuropathy in patients with Type 1 diabetes mellitus, J. Diabet Med. Mar. 2000;17(3), 181-9.

Li, L, et al, Rat C peptide I and II stimulate glucose utilization in STZ-induced diabetic rats, Diabetologia. 1999, 42(8), 958-64.

Johansson, BL, et al, C-peptide potentiates the vasoconstrictor effect of neuropeptide Y in insulin dependent diabetic patients, J. Acta Physiol Scand. 1999, 165, 39-44.

Oskarsson, P, et al, Effects of C-peptide on insulin-induced hypoglycaemia and its counterregulatory responses in IDDM patients, Diabet Med. Aug. 1997;14(8), 655-9.

(Continued)

*Primary Examiner*—Julie Ha
(74) *Attorney, Agent, or Firm*—Dennis A. Bennett; Andrew Cubitt

(57) ABSTRACT

Improved methods and kits for treating the long-term complication of diabetes that reduce the risk of the patient developing hypoglycemia during C-peptide therapy. The use of such methods and kits, can also maintain good glycemic control, and avoid excessive weight gain that may otherwise be associated with excessive insulin administration or caloric intake during C-peptide therapy.

20 Claims, 6 Drawing Sheets

OTHER PUBLICATIONS

Ido, Y, et al, Prevention of vascular and neural dysfunction in diabetic rats by C-peptide, Science. 1997, 277(5325), 563-6.

Johansson, BL, C-peptide improves autonomic nerve function in IDDM patients, Diabetologia. 1996, 39(6), 687-95.

Wu, W, Effect of C-peptide administration on whole body glucose utilization in STZ-induced diabetic rats, Acta Physiol Scand. 1996, 157(2), 253-8.

Zierath, JR, et al, C-peptide stimulates glucose transport in isolated human skeletal muscle independent of insulin receptor and tyrosine kinase activation, Diabetologia. 1996, 39, 306-13.

Zierath, JR, et al, In vitro studies of skeletal muscle: Hormonal and metabolic regulation of glucose transport, Acta Physiol Scand. 1995, 155 (Suppl. 626), 11-96.

Johansson, BL, et al, Influence of combined C-peptide and insulin administration on renal function and metabolic control in diabetes type 1, J Clin Endocrinol Metab. 1993, 77(4), 976-81.

Johansson, BL, et al, Effects of C-peptide on blood flow, capillary diffusion capacity and glucose utilization in the exercising forearm of type 1 (insulin-dependent) diabetic patients, Diabetologia. Dec. 1992;35(12), 1151-8.

Johansson, BL, et al, The influence of human C-peptide on renal function and glucose utilization in type 1 (insulin-dependent) diabetic patients, Diabetologia. 1992, 35(2), 121-8.

Sjoberg, S, et al, Renal and splanchnic exchange of human biosynthetic C-peptide in type 1 (insulin-dependent) diabetes mellitus, Diabetologia. Jun. 1991;34(6), 423-8.

Zierath, JR, et al, Effect of human C-peptide on glucose transport in in vitro incubated human skeletal muscle, Diabetologia. 1991, 34(12), 899-901.

Schatz, H, et al, Bioactivity and pharmacokinetics of human proinsulin in comparison to human insulin after intravenous and subcutaneous injection, Horm Metab Res. Jul. 1988;20(7), :445-9.

Wojcikowski, C, et al, Effects of synthetic rat C-peptide in normal and diabetic rats, Diabetologia. Sep. 1983;25(3), 288-90.

Meyer, J.A., et al, Metal-activated C-peptide facilitates glucose clearance and the release of a nitric oxide stimulus via the GLUT1 transporter, Diabetologia, 51, 175-182, 2008.

Kamiya, H., et al, The beneficial effects of C-peptide on Diabetic polyneuropathy, Rev. Diabet. Stud., 6 (3), 187-202, 2009.

Wahren, J., et al, C-peptide is relevant in type 1 diabetes and its complications: Summary and Conclusions to the Special Issue, Rev. Diabet. Stud., 6 (3), 223-224, 2009.

Learning to live well with diabetes, Ed. Cheryl Weiler, DCI Publishing, Minneapolis (1991).

American Diabetes association complete guide to diabetes. American Diabetes Association, Alexandria, VA (1996).

Fig. 1

|  | Screening/ Baseline | Visit 1 1.5 mo ± 2 wks | Visit 2 3 mo ± 2 wks | Visit 3 4.5 mo ± 2 wks | Visit 4 6 mo ± 2 wks | |
|---|---|---|---|---|---|---|
| Demography and medical history | x |  |  |  |  | x[1] |
| Informed consent and inclusion/exclusion criteria | x |  |  |  |  |  |
| ECG | x |  |  |  |  | x |
| E/I ratio | x |  |  |  |  | x[2] |
| Physical examination and safety lab tests[3] | x |  |  | x |  | x |
| HbA1c, serum C-peptide[4], and C-peptide antibodies | x |  |  | x[5] | x[7] | x[5] |
| HLA classification |  |  |  | x |  |  |
| Vital signs | x |  | x | x | x | x |
| NCV and perception thresholds[6] | x | x |  |  | x | x |
| Neurological examination, symptom assessment | x |  |  |  |  | x |
| Sexual dysfunction questionnaire | x |  |  |  |  | x |
| Randomization |  | x |  |  |  |  |
| Drug dispense |  | x | x | x | x |  |
| Drug accountability |  |  | x | x | x | x |
| Treatment of C-peptide or placebo |  | •————————————————————————▶ | | | | |
| AE documentation |  | •————————————————————————▶ | | | | |

[1] only body weight
[2] only for patients with abnormal value/dysfunction at baseline
[3] do not require subject to be in the fasted state
[4] duplicate samples are taken at baseline (one for immediate analysis and one for storage)
[5] C-peptide samples should be taken within 1-2.5 hours after the latest C-peptide/placebo injection
[6] two measurements within 2-14 days
[7] only C-peptide sample, taken prior to the morning dose of C-peptide/placebo (in 22 patients at Karolinska Hospital)

METHODS AND KITS FOR PREVENTING HYPOGLYCEMIA

CROSS-REFERENCE TO RELATED APPLICATIONS

This application claims the benefit of U.S. provisional patent application No. 61/255,560 filed on Oct. 28, 2009 and U.S. non-provisional patent application Ser. No. 12/717,794 filed on Mar. 4, 2010, the entire contents of which are incorporated herein by reference.

TECHNICAL FIELD

The present invention relates to improved dosing regimens for the treatment of the long-term complications of insulin-dependent diabetes with C-peptide in patients with neuropathy that reduce the risk of the patient developing hypoglycemia, while maintaining good glycemic control, and/or avoiding excessive weight gain.

BACKGROUND OF THE INVENTION

C-peptide is the linking peptide between the A- and B-chains in the proinsulin molecule. After cleavage in the endoplasmic reticulum of pancreatic islet β-cells, insulin and a 35 amino acid peptide are generated. The latter is processed to the 31 amino acid peptide, C-peptide, by enzymatic removal of two basic residues on either side of the molecule. C-peptide is co-secreted with insulin in equimolar amounts from the pancreatic islet β-cells into the portal circulation. Besides its contribution to the folding of the two-chain insulin structure, further biologic activity of C-peptide was questioned for many years after its discovery.

Type 1 diabetes, or insulin-dependent diabetes mellitus, is generally characterized by insulin and C-peptide deficiency, due to an autoimmune destruction of the pancreatic islet β-cells. The patients are therefore dependent on exogenous insulin to sustain life. Several factors may be of importance for the pathogenesis of the disease, e.g., genetic background, environmental factors, and an aggressive autoimmune reaction following a temporary infection (Akerblom H K et al.: *Annual Medicine* 29(5): 383-385, (1997)). Currently insulin-dependent diabetics are provided with exogenous insulin which has been separated from the C-peptide, and thus do not receive exogenous C-peptide therapy. By contrast most type 2 diabetics initially still produce both insulin and C-peptide endogenously, but are generally characterized by insulin resistance in skeletal muscle and adipose tissue.

In addition to type 1 and type 2 diabetics, there is increasing recognition of a subclass of diabetes referred to as Latent Autoimmune Diabetes in the Adult (LADA) or Late-onset Autoimmune Diabetes of Adulthood, or "Slow Onset Type 1" diabetes, and sometimes also "Type 1.5" or "Type one-and-a-half" diabetes. In this disorder, diabetes onset generally occurs in ages 35 and older, and antibodies against components of the insulin-producing cells are always present, demonstrating that autoimmune activity is an important feature of LADA. It is primarily antibodies against glutamic acid decarboxylase (GAD) that are found. Some LADA patients show a phenotype similar to that of type 2 patients with increased body mass index (BMI) or obesity, insulin resistance, and abnormal blood lipids. Genetic features of LADA are similar to those for both type 1 and type 2 diabetes. During the first 6-12 months after debut the patients may not require insulin administration and they are able to maintain relative normoglycemia via dietary modification and/or oral anti-diabetic medication. However, eventually all patients become insulin dependent, probably as a consequence of progressive autoimmune activity leading to gradual destruction of the pancreatic islet β-cells. At this stage the LADA patients show low or absent levels of endogenous insulin and C-peptide, and they are prone to develop long-term complications of diabetes involving the peripheral nerves, the kidneys, or the eyes similar to type 1 diabetes patients and thus become candidates for C-peptide therapy (Palmer et al.: *Diabetes* 54(suppl 2): S62-67, (2005); Desai et al.: *Diabetic Medicine* 25(suppl 2): 30-34, (2008); Fourlanos et al.: *Diabetologia* 48: 2206-2212, (2005)).

Type 1 diabetics suffer from a constellation of long-term complications of diabetes that are in many cases more severe and widespread than in type 2 diabetes. Specifically, e.g., microvascular complications involving retina, kidneys, and nerves are a major cause of morbidity and mortality in patients with type 1 diabetes.

Roughly 30% of all patients with type 1 diabetes develop diabetic nephropathy characterized by gradually increasing albuminuria, decline in glomerular filtration rate (GFR), and elevated systemic blood pressure 10 to 20 years after the onset of the disease. Five years later many of these patients may suffer from end-stage renal disease (Bretzel R G: *J. Diabetes Complications* 11(2): 112-122, (1997)); Chiarelli F et al.: *Annual Medicine* 29(5): 439-445, (1997)), a condition requiring hemodialysis or transplantation. Microalbuminuria, defined as a urinary albumin excretion rate between 30 and 300 mg/day, strongly predicts the development of nephropathy in diabetes. The diabetes patients with nephropathy suffer a high mortality rate compared with diabetes patients without nephropathy.

A multiplicity of peripheral nerve dysfunctions may develop in approximately 50% of the patients with type 1 diabetes (Dyck P J et al.: *Neurology* 43(4): 817-824, (1993)). The distal symmetric polyneuropathy that predominantly affects sensory and autonomic function is the most common manifestation (Fedele D et al.: *Drugs* 54(3): 414-421, (1997)) with symptoms such as paresthesias, numbness, and hyperalgesia and in some cases severe pain. Typically, the symptoms initially occur in the lower limbs. Diabetic neuropathy is the leading reason for limb amputation.

Diabetic eye disease and its complications, especially diabetic retinopathy, are leading causes of blindness and visual dysfunction in developed countries. Approximately 25% of the patients with type 1 diabetes have retinopathy after five years of the disease, increasing to 60% and 80% after 10 and 15 years, respectively (Aiello L P et al.: *Diabetics Care* 1(1): 143-56, (1998)).

There is currently no causal treatment for prevention of long-term complications in patients with diabetes. However, maintenance of glucose concentrations at the near-normal level is of utmost importance, as it may to some degree delay the onset and retard the progression of diabetic nephropathy, neuropathy, and retinopathy (DCCT Research Group: *New England Journal of Medicine* 329: 977-86, (1993)).

There is increasing support for the concept that C-peptide deficiency may play a role in the development of the long-term complications of insulin-dependent diabetics. Additionally, in vivo as well as in vitro studies, in diabetic animal models and in patients with type 1 diabetes, demonstrate that C-peptide possesses hormonal activity (Wahren J et al.: *American Journal of Physiology* 278: E759-E768, (2000); Wahren J et al.: In *International textbook of diabetes mellitus* Ferranninni E, Zimmet P, De Fronzo R A, Keen H, Eds. Chichester, John Wiley & Sons, (2004), p. 165-182). Thus, C-peptide used as a complement to regular insulin therapy may provide an effective approach to the management of type 1 diabetes long-term complications.

Studies to date suggest that C-peptide's therapeutic activity involves the binding of C-peptide to a G-protein-coupled membrane receptor, activation of $Ca^{2+}$-dependent intracellular signalling pathways, and phosphorylation of the MAP-kinase system, eliciting increased activities of both $Na^+,K^+$-ATPase and eNOS. Additionally, some studies indicate that C-peptide may interact with insulin, an effect that may be mediated, at least in part, by the dispersal of zinc insulin hexamers via C-peptide. Furthermore, the simultaneous subcutaneous (S.C.) injection of hexameric insulin and C-peptide at the same injection site, but not different injection sites, results in increased glucose utilization, a more pronounced antilipolytic effect, and a more marked depression of plasma glucagon levels in type 1 diabetic patients compared to administration of insulin alone (WO 2007/015069, entitled "Compositions and methods of treating diabetes"; Shafqat et al.: *Cell. Mol. Life. Sci.* 63: 1805-1811, (2006)). It is thus suggested that C-peptide plays a role in promoting the disaggregation of insulin hexamers both in vivo, and when co-administered with insulin at the same site.

The estimated association constant for C-peptide binding to its cellular receptor is $3\times10^9$ $M^{-1}$. Half-saturation of C-peptide binding to renal tubular cells occurs at approximately 0.3 nM (Rigler R et al.: *PNAS USA* 96: 13318-13323, (1999)). Consequently, it is likely that in healthy humans near-saturation of the receptor is reached at normal circulating levels of C-peptide which vary from about 0.47±0.15 nM; (range 0.19 to 0.99 nM) when fasting, to about 2.51±0.75 nM; (range 0.72 to 6.5 nM) postprandially (Dalla-Man et al., *Diabetes* 54: 3265-3273, (2005)). This finding helps explain the consistent observation that effects of C-peptide cannot be demonstrated in non-diabetic animals or healthy subjects (Hoogwerf B et al.: *Metabolism* 35: 122-125, (1986); Johansson B L et al.: *Diabetologia* 35: 1151-1158, (1992); Wójcikowski C et al.: *Diabetologia* 25: 288-290, (1983)); it is only in diabetic animals or in patients with C-peptide deficiency that specific effects of C-peptide have been observed.

Studies of type 1 diabetes in animal models demonstrate that C-peptide in replacement doses has the ability to improve peripheral nerve function and prevent or reverse the development of nerve structural changes. Thus, C-peptide administration for 2 months (75 nmol/kg/24 h S.C. using osmotic pumps) in diabetic BB/Wor rats, starting one week after onset of diabetes, reduces the development of the acute nerve conduction velocity (NCV, sciatic-tibial nerve) defect by 60% compared to non-replaced diabetic control animals (Sima A et al.: *Diabetologia* 44: 889-897, (2001)).

In a short-term study, involving human C-peptide infusion (0.5 nmol/kg/min intravenous [I.V.]) for 60 min in STZ-D rats, it could be demonstrated that compared to control animals, glomerular hyperfiltration decreased, albumin excretion fell and renal functional reserve rose (Sjöquist M et al.: *Kidney International* 54: 758-764, (1998)).

Over the last 15 years at least 19 clinical trials have been performed on C-peptide in humans, including approximately 340 type 1 diabetes patients receiving recombinantly produced C-peptide. C-peptide has been administered I.V. in doses of 5-30 pmol/kg/min for one to three hours and S.C. in single doses of 60-1800 nmol (approximately 0.18 to 5.4 mg) or in repeated injection in a total dose of 600-3,000 nmol/day (approximately 1.8 to 9 mg/day) S.C. given 3-4 times daily for three months. In one study C-peptide was administered together with insulin via a pump for one month (Johansson B L et al.: *J. Clin. Endocrin. Metab.* 77(4): 976-981, (1993)). Most of the studies were randomized, double blind, and placebo controlled. The studies focused on vascular dysfunction, metabolic effects and kinetics, and early-stage nephropathy, neuropathy, and retinopathy. Several physiological effects of C-peptide were observed in diabetes patients lacking endogenous C-peptide production. (Ekberg K et al.: *Diabetes* 55: 536-541, (2003); Hansen A et al.: *Diabetes* 51: 3077-3082, (2002); Johansson B L et al.: *Am. J. Phys. Endocrin. Metab.* 285: E864-E870, (2004); Johansson B L et al.: *Diabetic Med.* 17(3): 181-189, (2000); Fernqist-Forbes E et al.: *Acta Physiol. Scand.* 172: 159-165, (2001); Johansson B L et al.: *Acta Physiol. Scand.* 165: 39-44, (1999); Johansson B L et al.: *Diabetologia* 39(6): 687-695, (1996); Oskarsson P et al.: *Diabetic Med.* 14: 655-659, (1997); Johansson B L et al.: *Diabetologia* 35: 1151-1158, (1992); Sjoberg S et al.: *Diabetologia* 34: 423-428, (1991); Johansson B L et al.: *Diabetologia* 35: 121-128, (1992)).

Despite these intensive efforts, and long-felt need for an effective therapy for the treatment of the long-term complications of insulin-dependent diabetes, C-peptide has yet to be approved for therapeutic use. A significant barrier to the development of a commercially viable C-peptide therapy lies in the need to establish an effective dosing regimen for C-peptide and insulin administration that is both therapeutically effective in preventing or reversing the effects of the long-term complications of insulin-dependent diabetes, and safe and well tolerated by the patient.

The present invention is focused on the development of more effective C-peptide therapies for the treatment of the long-term complications of diabetes. In one aspect, such improved therapies are based on improved dosing regimens for C-peptide and insulin that reduce the risk of the patient developing hypoglycemia, while maintaining good glycemic control, and/or avoiding excessive weight gain. These improved methods and kits are based on clinical trial results that surprisingly demonstrate that subcutaneous C-peptide administration in a subset of patients with neuropathy results in a sustained reduction in insulin requirements, and therefore confers an increased risk of hypoglycemia in such patients. The present invention is further based in part on the discovery that the risk of hypoglycemia in such patients can be mitigated while maintaining good glycemic control by reducing the patient's insulin dose during on-going C-peptide therapy. In one aspect, such improved dosing regimens are based on an assessment of the response of the patient to C-peptide administration.

SUMMARY OF THE INVENTION

In one aspect, the present invention includes a method for treating an insulin-dependent human patient, comprising the steps of; a) administering insulin to said patient, wherein said patient has neuropathy; b) administering subcutaneously to said patient a therapeutic dose of C-peptide in a different site as that used for said patient's insulin administration; c) adjusting the dosage amount, type, or frequency of insulin administered based on monitoring said patient's altered insulin requirements resulting from said therapeutic dose of C-peptide, wherein said adjusted dose of insulin reduces the risk, incidence, or severity of hypoglycemia, wherein said adjusted dose of insulin is at least 10% less than said patient's insulin dose prior to starting C-peptide treatment. In one aspect of this method, the hypoglycemia is severe hypoglycemia. In another aspect of this method, the hypoglycemia is asymptomatic hypoglycemia.

In another aspect, the present invention includes a method of reducing insulin usage in an insulin-dependent human patient, comprising the steps of; a) administering insulin to said patient, wherein said patient has neuropathy; b) administering subcutaneously to said patient a therapeutic dose of C-peptide in a different site as that used for said patient's insulin administration; c) adjusting the dosage amount, type, or frequency of insulin administered based on monitoring said patient's altered insulin requirements resulting from said therapeutic dose of C-peptide, wherein said adjusted dose of insulin does not induce hyperglycemia, wherein said adjusted dose of insulin is at least 10% less than said patient's insulin dose prior to starting C-peptide treatment.

In one aspect, the present invention includes methods for treating an insulin-dependent patient without substantially increasing the risk, incidence, or severity of hypoglycemia comprising the steps of; a) administering insulin to the patient; b) administering subcutaneously to the patient a therapeutic dose of C-peptide in a different site as that used for the patient's insulin administration; and c) adjusting the dosage amount, type, or frequency of insulin administered based on said patient's altered insulin requirements resulting from said therapeutic dose of C-peptide.

In another embodiment, the present invention includes a method for reducing insulin usage in an insulin-dependent patient without inducing hyperglycemia comprising the steps of; a) administering insulin to the patient; b) administering subcutaneously to the patient a therapeutic dose of C-peptide in a different site as that used for the patient's insulin administration; and c) adjusting the dosage amount, type, or frequency of insulin administered based on said patient's altered insulin requirements resulting from said therapeutic dose of C-peptide.

In another embodiment, the present invention includes a method for reducing weight gain in an insulin-dependent patient comprising the steps of; a) administering insulin to the patient; b) administering subcutaneously to the patient a therapeutic dose of C-peptide in a different site as that used for the patient's insulin administration; and c) adjusting the dosage amount, type, or frequency of insulin administered based on said patient's altered insulin requirements resulting from said therapeutic dose of C-peptide.

In an additional embodiment, the invention includes a kit comprising in combination: a pharmaceutical composition of C-peptide and instructions for a dosing regimen for administration of said C-peptide to an insulin-dependent patient to reduce the risk, incidence, or severity of hypoglycemia. In one aspect, the kit includes instructions to reduce the administration of insulin by about 10% to about 35% when starting C-peptide therapy.

In one aspect of any of these methods and kits, the methods further include the step of monitoring the patient to determine the patient's risk factors, patient parameters, and/or insulin requirements.

In a further aspect of any of these methods and kits, the patient of the method has been diagnosed with a long-term complication of type 1 diabetes. In one aspect the long-term complication of type 1 diabetes is selected from the group consisting of retinopathy including early stage retinopathy with microaneurysms, proliferative retinopathy, and macular edema; peripheral neuropathy including sensorimotor polyneuropathy, painful sensory neuropathy, acute motor neuropathy, cranial focal and multifocal polyneuropathies, thoracolumbar radiculoneuropathies, proximal diabetic neuropathies, and focal limb neuropathies including entrapment and compression neuropathies; autonomic neuropathy involving the cardiovascular system, the gastrointestinal tract, the respiratory system, the urigenital system, sudomotor function and papillary function; and nephropathy including disorders with microalbuminuria, overt proteinuria, and end-stage renal disease. In further aspects, the patient may be diagnosed with retinopathy, peripheral neuropathy, autonomic neuropathy, or nephropathy.

In additional embodiments of any of the claimed methods and kits, the therapeutic dose of C-peptide is from about 0.5 mg to about 6.0 mg/24 hours. In another aspect, the therapeutic dose of C-peptide is from about 2.0 mg to about 6.0 mg/24 hours. In another aspect, the therapeutic dose of C-peptide is from about 1.5 mg to about 4.5 mg/24 hours. In one aspect of any of these claimed methods, the administration of C-peptide is via a sustained release composition or device. In one aspect of any of these claimed methods, the therapeutic dose of C-peptide maintains an average steady state concentration of C-peptide ($C_{ss-ave}$) in said patient's plasma of between about 0.2 nM and about 6 nM.

In another aspect of any of these methods and kits, the administration of insulin is via subcutaneous injection.

In another embodiment of any of these methods and kits, the patient's altered insulin requirements are assessed by monitoring one or more clinical parameters, biomarkers, or analytes prior to starting C-peptide treatment.

In a further aspect of any of these methods and kits, the patient's altered insulin requirements are assessed by comparing one or more clinical parameters, biomarkers, or analytes prior to and after starting C-peptide treatment. In one aspect of any of these methods, the therapeutic dose of C-peptide has been administered to said patient for at least one week prior to adjusting the insulin dose. In one aspect of any of these methods, monitoring is conducted over an evaluation period of about two weeks after starting C-peptide therapy.

In additional embodiments of any of these methods and kits, the clinical parameters are selected from one or more of the group consisting of body mass index, nerve conduction velocity, and QTc interval. In another aspect, the analytes are selected from one or more of the group consisting of glucose, insulin, C-peptide, and glycosylated hemoglobin.

In further embodiments of any of these claims, the dose of insulin administrated is reduced by about 5% to about 50% compared to said patient's insulin dose prior to starting C-peptide treatment. In another aspect of any of these claims, the dose of insulin administrated is reduced by about 5% to about 45% compared to said patient's insulin dose prior to starting C-peptide treatment. In another aspect of any of these claims, the dose of insulin administrated is reduced by about 5% to about 35% compared to said patient's insulin dose prior to starting C-peptide treatment. In another aspect of any of these claims, the dose of insulin administrated is reduced by about 5% to about 25% compared to said patient's insulin dose prior to starting C-peptide treatment. In another aspect of any of these claims, the dose of insulin administrated is reduced by about 5% to about 15% compared to said patient's insulin dose prior to starting C-peptide treatment. In another aspect of any of these claims, the dose of insulin administrated is reduced by about 10% to about 15% compared to said patient's insulin dose prior to starting C-peptide treatment In another aspect of any of these claims, the dose of insulin administrated is reduced by about 10% to about 20% compared to said patient's insulin dose prior to starting C-peptide treatment In another aspect of any of these claims, the dose of insulin administrated is reduced by about 10% to about 25% compared to said patient's insulin dose prior to starting C-peptide treatment In another aspect of any of these claims, the dose of insulin administrated is reduced by about 10% to about 30% compared to said patient's insulin dose prior to starting C-peptide treatment In another aspect of any of these claims, the dose of insulin administrated is reduced by about 10% to about 35% compared to said patient's insulin dose prior to starting C-peptide treatment. In another aspect of any of these claims, the dose of insulin administrated is reduced by about 2% to about 15% compared to said patient's insulin dose prior to starting C-peptide treatment In another aspect of any of these claims, the dose of insulin administrated is reduced by at least 10% less than said patient's insulin dose prior to starting C-peptide treatment.

In one aspect of this method, the reduction in insulin administration is made in the form of a reduction in short-acting insulin administration. In another aspect of this method, the reduction in insulin administration is made in the form of a reduction in intermediate-acting insulin administration. In another aspect of this method, the reduction in insulin administration is made in the form of a reduction in long-acting insulin administration.

In a further embodiment, the invention includes a method for identifying patients that respond to C-peptide by a change in insulin requirements by monitoring said patient to determine said patient's basal C-peptide levels prior to starting C-peptide therapy.

In an additional embodiment, the invention includes a method for identifying patients that respond to C-peptide by a change in insulin requirements by monitoring said patient to determine said patient's change in nerve conduction velocity during C-peptide treatment.

In an additional further embodiment, the invention includes a method for identifying patients that respond to C-peptide by a change in insulin requirements by monitoring said patient to determine said patient's change in autonomic nerve function during C-peptide treatment.

In one further embodiment, the present invention includes a method for the treatment of a patient with a long-term complication of diabetes by C-peptide which minimizes the risk of the patient developing hypoglycemia, comprising the steps of; a) monitoring one or more clinical parameters, biomarkers, or analytes from the patient and/or monitoring the patient's insulin usage over a baseline period prior to starting C-peptide therapy; b) administering a therapeutically effective dose of C-peptide for an evaluation period; c) re-monitoring one or more of the clinical parameters, biomarkers, or analytes and/or re-monitoring the patient's insulin usage over the evaluation period to determine a new reference range of parameters; and d) reducing the dose, frequency, or type of insulin administration based on a comparison of the baseline reference range and new reference range of the parameters.

In another embodiment, the present invention includes a method for the treatment for a long-term complication of diabetes via treatment with C-peptide, which reduces the risk of the patient developing hypoglycemia during the therapy, comprising the steps of; a) monitoring one or more clinical parameters, biomarkers, or analytes and/or monitoring the patient's insulin usage over an evaluation period of C-peptide therapy to determine a reference range of insulin sensitivity for the patient when treated with C-peptide; and b) reducing the dose, frequency, or type of insulin administration based on a comparison of the patient's clinical parameters, biomarkers, or analytes obtained during the evaluation period compared to an index reference range of parameters for that patient.

In a further embodiment, the present invention includes a method for the treatment of long-term complications of diabetes via treatment with C-peptide which reduces the risk of the patient developing hypoglycemia during the therapy, of comprising the steps of; a) monitoring at least the incidence of hypoglycemic events experienced by the patient during an evaluation period of C-peptide therapy; and b) reducing the average daily requirement of insulin administered to the patient calculated prior to starting C-peptide therapy by about 5% to about 50% if the incidence of hypoglycemic events observed during the evaluation period of C-peptide therapy is increased compared to the incidence of hypoglycemic events observed prior to starting C-peptide therapy.

In another embodiment, the present invention includes a method for reducing the risk of a patient with insulin-dependent diabetes developing hypoglycemia when treated with C-peptide comprising the steps of; a) assessing the patient's C-peptide levels prior to starting C-peptide therapy; and b) reducing the average daily dose of insulin administered to the patient by about 5% to about 50%.

In another embodiment, the present invention includes a method for reducing weight gain in a patient with insulin-dependent diabetes when treated with C-peptide comprising the steps of; a) assessing the patient's C-peptide levels prior to starting C-peptide therapy; and b) reducing the average daily dose of insulin administered to the patient by about 5% to about 50%.

In another embodiment, the present invention includes a method for the treatment of a patient with insulin-dependent diabetes who is starting a therapy for a long-term complication of diabetes via treatment with C-peptide which reduces the risk of the patient developing hypoglycemia, comprising the steps of; a) assessing the patient's average daily requirement of insulin including number of international units of short-, intermediate-, and long-acting insulin that the patient administers prior to starting C-peptide therapy; b) administering subcutaneously to the patient a therapeutically effective dose of C-peptide for a lead-in period; and c) reducing the average daily requirement of short-, intermediate-, or long-acting insulin administered to the patient by about 5% to about 50% compared to the amount administered prior to starting C-peptide therapy.

In one aspect of any of the claimed methods, the patient is a human. In another aspect of any of the claimed methods, the patient has neuropathy. In another aspect of any of the claimed methods, the patient has incipient neuropathy. In another aspect of any of the claimed methods, the patient has established neuropathy. In another aspect of any of the claimed methods, the patient has type 1.5 diabetes. In another aspect of any of the claimed methods, the patient has type 1 diabetes. In one aspect of any of the claimed methods, the patient is being treated for a long-term complication of type 1 diabetes. In one aspect of this method, the complication of type 1 diabetes is peripheral neuropathy.

BRIEF DESCRIPTION OF THE DRAWINGS

A better understanding of the features and advantages of the present invention can be obtained by reference to the following detailed description that sets forth illustrative embodiments, in which the principles of the invention are utilized, and the accompanying drawings of which:

FIG. 1 shows an overview flow chart of visits and variables determined during the clinical trial of C-peptide therapy (as more fully described in Examples).

DETAILED DESCRIPTION OF THE INVENTION

Definitions

Figure 2:
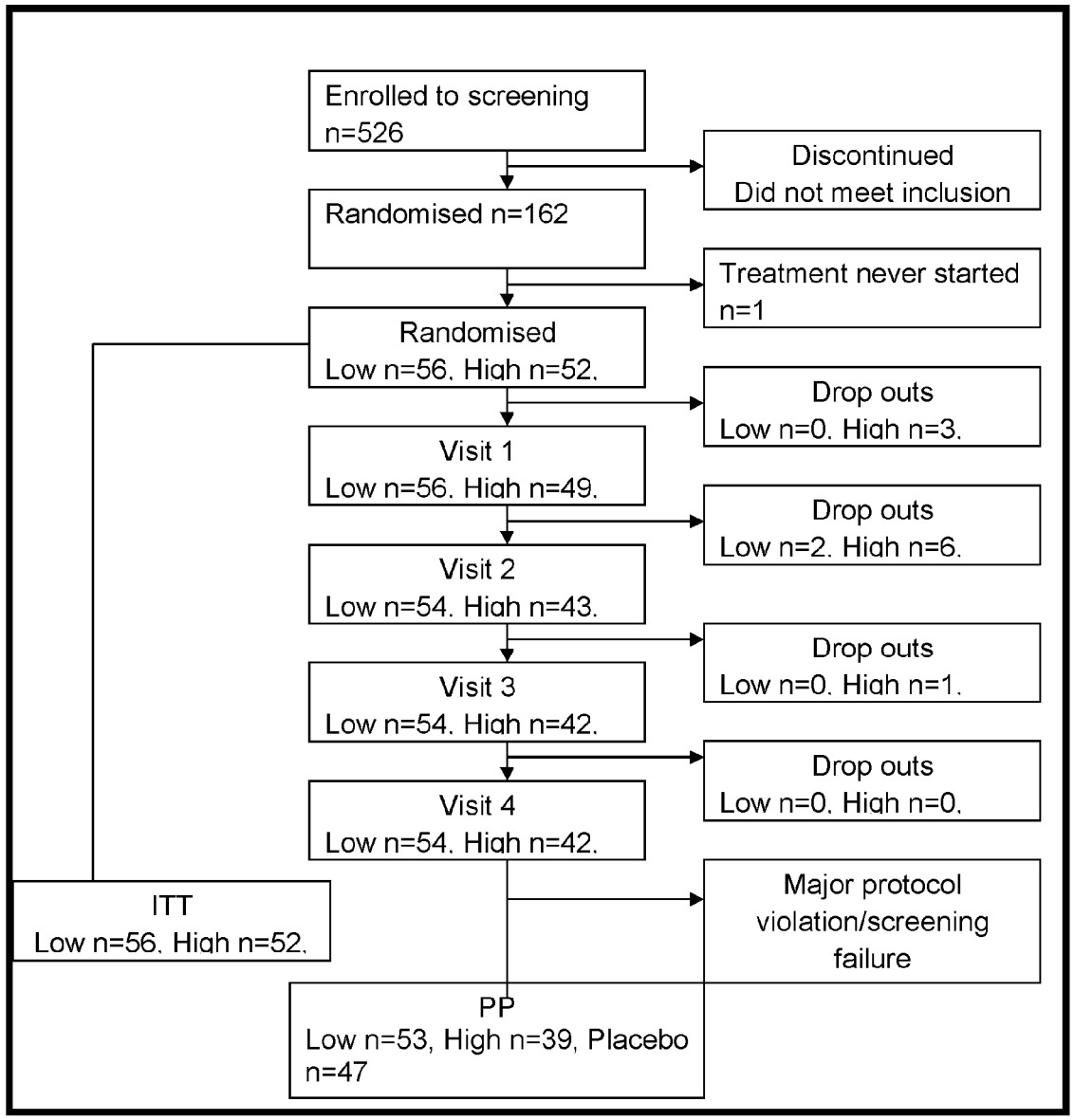
FIG. 2 shows the disposition of patients in the study (ITT=intend-to-treat; PP=per-protocol).

The term "$C_{max}$" as used herein is the maximum serum or plasma concentration of drug which occurs during the period of release which is monitored.

The term "$C_{min}$" as used herein is the minimum serum or plasma concentration of drug which occurs during the period of release during the treatment period.

The term "$C_{ave}$" as used herein is the average serum concentration of drug derived by dividing the area under the curve (AUC) of the release profile by the duration of the release.

The term "$C_{ss-ave}$" as used herein is the average steady-state concentration of drug obtained during a multiple dosing regimen after dosing for at least five elimination half-lives. It will be appreciated that drug concentrations are fluctuating within dosing intervals even once an average steady-state concentration of drug has been obtained.

The term "$t_{max}$" as used herein is the time post-dose at which $C_{max}$ is observed.

The term "AUC" as used herein means "area under curve" for the serum or plasma concentration-time curve, as calculated by the trapezoidal rule over the complete sample collection interval.

The term "analyte" as used herein can mean any substance to be measured and can encompass electrolytes and trace elements, including without limitation, glucose levels, insulin concentration, free fatty acids, glycosylated hemoglobin, free fatty acids, triglycerides, ketones, and C-peptide.

The term "bioavailability" refers to the amount of drug that reaches the circulation system expressed in percent of that administered. The amount of bioavailable material can be defined as the calculated AUC for the release profile of C-peptide during the time period starting at post-administration and ending at a predetermined time point. As is understood in the art, a release profile is generated by graphing the serum levels of a biologically active agent in a subject (Y-axis) at predetermined time points (X-axis). Bioavailability is often referred to in terms of bioavailability, which is the bioavailability achieved for a drug (such as C-peptide) following administration of a sustained release composition of that drug divided by the bioavailability achieved for the drug following intravenous administration of the same dose of drug, multiplied by 100.

The term "biomarker" in the context of the present invention encompasses, without limitation, proteins, nucleic acids, and metabolites, together with their polymorphisms, mutations, variants, modifications, subunits, fragments, protein-ligand complexes, and degradation products, protein-ligand complexes, elements, related metabolites, and other analytes or sample-derived measures. Biomarkers can also include mutated proteins or mutated nucleic acids. Biomarkers also encompass non-blood-borne factors, non-analyte physiological markers of health status, or other factors or markers not measured from samples (e.g., biological samples such as bodily fluids), such as "clinical parameters" defined herein, or results from scanning technologies such as MRI or PET (with or without diagnostic tracers). Biomarkers also include any calculated indices created mathematically or combinations of any one or more of the foregoing measurements, including temporal trends and differences.

The term "BMI" as used herein means the body mass index, calculated as weight in kg divided by the squared height in m (i.e., $m^2$).

The term "clinical parameters" or "CPs" encompasses all non-sample or non-analyte biomarkers of a subject's health status or other characteristics, such as, without limitation, body temperature, age, race, length of disease duration, length of time of insulin treatment, severity of disease complications, or ethnicity, gender, EEG recordings, diastolic and systolic blood pressures, heart rate variability (HRV) and complexity analyses, pulse, QTc interval (QT interval corrected for heart rate), peak or initial nerve conduction velocity, amplitude of the nerve signal, vibration perception threshold, family history, height, weight, waist and hip circumference, waist-to-hip ratio, bio-impedance, BMI, caloric intake, exercise regimen, erectile function, daily insulin usage, including dosage forms and type.

The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz G E and R H Schirmer, Principles of Protein Structure, Springer-Verlag (1979)). According to such analyses, groups of amino acids can be defined where amino acids within a group exchange preferentially with each other, and therefore resemble each other most in their impact on the overall protein structure (Schulz G E and R H Schirmer, Principles of Protein Structure, Springer-Verlag (1979)).

Examples of amino acid groups defined in this manner include: a "charged/polar group," consisting of Glu, Asp, Asn, Gln, Lys, Arg, and His; an "aromatic or cyclic group," consisting of Pro, Phe, Tyr, and Trp; and an "aliphatic group," consisting of Gly, Ala, Val, Leu, Ile, Met, Ser, Thr, and Cys.

Within each group, subgroups can also be identified, e.g., the group of charged/polar amino acids can be sub-divided into the subgroups consisting of the "positively-charged subgroup," consisting of Lys, Arg, and His; the "negatively-charged subgroup," consisting of Glu and Asp, and the "polar subgroup" consisting of Asn and Gln. The aromatic or cyclic group can be sub-divided into the subgroups consisting of the "nitrogen ring subgroup," consisting of Pro, His, and Trp; and the "phenyl subgroup" consisting of Phe and Tyr. The aliphatic group can be sub-divided into the subgroups consisting of the "large aliphatic non-polar subgroup," consisting of Val, Leu, and Ile; the "aliphatic slightly-polar subgroup," consisting of Met, Ser, Thr, and Cys; and the "small-residue subgroup," consisting of Gly and Ala.

Examples of conservative mutations include amino acid substitutions of amino acids within the subgroups above, e.g., Lys for Arg and vice versa such that a positive charge can be maintained; Glu for Asp and vice versa such that a negative charge can be maintained; Ser for Thr such that a free —OH can be maintained; and Gln for Asn such that a free —$NH_2$ can be maintained. "Semi-conservative mutations" include amino acid substitutions of amino acids with the same groups listed above, that do not share the same subgroup. For example, the mutation of Asp for Asn, or Asn for Lys, all involve amino acids within the same group, but different subgroups. "Non-conservative mutations" involve amino acid substitutions between different groups, e.g., Lys for Leu, Phe for Ser.

The terms "diabetes", "diabetes mellitus", or "diabetic condition", unless specifically designated otherwise, encompass all forms of diabetes. The term "Type 1 diabetic" or "Type 1 diabetes" refers to a patient with a fasting plasma glucose concentration of greater than about 7.0 mmoL/L and a fasting C-peptide level of about, or less than about 0.2 nmoL/L. The term "Type 1.5 diabetic" or "Type 1.5 diabetes" refers to a patient with a fasting plasma glucose concentration of greater than about 7.0 mmoL/L and a fasting C-peptide level of about, or less than about 0.4 nmoL/L. The term "Type 2 diabetic" or "Type 2 diabetes" generally refers to a patient with a fasting plasma glucose concentration of greater than about 7.0 mmoL/L and fasting C-peptide level that is within or higher than the normal physiological range of C-peptide levels (about 0.47 to 2.5 nmoL/L). It will be appreciated that a patient initially diagnosed as a type 2 diabetic may subsequently develop insulin-dependent diabetes, and may remain diagnosed as a type 2 patient, even though their C-peptide levels drop to those of a type 1.5 or type 1 diabetic patient (<0.2 nmol/L).

The terms "insulin-dependent patient" or "insulin-dependent diabetes" encompass all forms of diabetics/diabetes who/that require insulin administration to adequately maintain normal glucose levels unless specified otherwise.

Diabetes is frequently diagnosed by measuring fasting blood glucose, insulin, or glycated hemoglobin levels (which are typically referred to as hemoglobin A1c, $Hb_{1c}$, $Hb_{A1c}$, or A1C). Normal adult glucose levels are 60-126 mg/dL. Normal insulin levels are 30-60 pmoL/L. Normal HbA1c levels are generally less than 6%. The World Health Organization defines the diagnostic value of fasting plasma glucose concentration to 7.0 mmoL/L (126 mg/dL) and above for diabetes mellitus (whole blood 6.1 mmoL/L or 110 mg/dL), or 2-hour glucose level greater than or equal to 11.1 mmoL/L (greater than or equal to 200 mg/dL). Other values suggestive of or indicating high risk for diabetes mellitus include elevated arterial pressure greater than or equal to 140/90 mm Hg; elevated plasma triglycerides (greater than or equal to 1.7 mmoL/L [150 mg/dL]) and/or low HDL-cholesterol (less than 0.9 mmoL/L [35 mg/dL] for men; and less than 1.0 mmoL/L [39 mg/dL] for women); central obesity (BMI exceeding 30 $kg/m^2$); microalbuminuria, where the urinary albumin excretion rate is greater than or equal to 20 μg/min or the albumin creatinine ratio is greater than or equal to 30 mg/g.

The term "delivery agent" refers to carrier compounds or carrier molecules that are effective in the oral delivery of therapeutic agents, and may be used interchangeably with "carrier".

The phrase "equivalent therapeutically effective reduction" as used herein means that a maximal reduction of blood glucose concentration achieved by a first dose of insulin administration (e.g., via administration of insulin to a patient(s) in the absence of C-peptide) is not more than 20%, and preferably not more than 10%, and even more preferably not more than 5% different from a maximal reduction of blood glucose concentration after administration of a second dose of insulin to the same patient who is receiving C-peptide therapy or a different patient requiring the same reduction in blood glucose level. The phrase may also mean the dose required to approximate normoglycemia by any method of administration, normoglycemia being defined as variability from a patient's baseline blood glucose of not more than 20%, preferably 10%, more preferably 5%, in the fasted state.

The term "homology" describes a mathematically-based comparison of sequence similarities which is used to identify genes or proteins with similar functions or motifs. The nucleic acid and protein sequences of the present invention can be used as a "query sequence" to perform a search against public databases to, e.g., identify other family members, related sequences, or homologs. Such searches can be performed using the NBLAST and XBLAST programs (version 2.0) of Altschul et al.: J. Mol. Biol. 215: 403-410, (1990). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al.: Nucleic Acids Res. 25(17): 3389-3402, (1997). When utilizing BLAST and Gapped BLAST programs, the default parameters of the respective programs (e.g., XBLAST and BLAST) can be used (see www.ncbi.nlm.nih.gov).

The term "homologous" refers to the relationship between two proteins that possess a "common evolutionary origin", including proteins from superfamilies (e.g., the immunoglobulin superfamily) in the same species of animal, as well as homologous proteins from different species of animal (e.g., myosin light chain polypeptide; see Reeck et al.: Cell 50: 667, (1987)). Such proteins (and their encoding nucleic acids) have sequence homology, as reflected by their sequence similarity, whether in terms of percent identity or by the presence of specific residues or motifs and conserved positions. In specific embodiments, two nucleic acid sequences are "substantially homologous" or "substantially similar" when at least about 85%, and more preferably at least about 90% or at least about 95% of the nucleotides match over a defined length of the nucleic acid sequences, as determined by a sequence comparison algorithm known such as BLAST, FASTA, DNA Strider, CLUSTAL, etc. An example of such a sequence is an allelic or species variant of the specific genes of the present invention. Sequences that are substantially homologous may also be identified by hybridization, e.g., in a Southern hybridization experiment under, e.g., stringent conditions as defined for that particular system.

Similarly, in particular embodiments of the invention, two amino acid sequences are "substantially homologous" or "substantially similar" when greater than 80% of the amino acid residues are identical, or when greater than about 90% of the amino acid residues are similar (i.e., are functionally identical). Preferably the similar or homologous polypeptide sequences are identified by alignment using, e.g., the GCG (Genetics Computer Group, version 7, Madison, Wis.) pileup program, or using any of the programs and algorithms described above. The program may use the local homology algorithm of Smith and Waterman with the default values: gap creation penalty=−(1+⅓ k), k being the gap extension number, average match=1, average mismatch=−0.333.

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in Computational Molecular Biology, Lesk A M, ed., Oxford University Press, New York, (1988); Biocomputing: Informatics and Genome Projects, Smith D W, ed., Academic Press, New York, (1993); Computer Analysis of Sequence Data, Part I, Griffin A M and Griffin H G, eds., Humana Press, New Jersey, (1994); Sequence Analysis in Molecular Biology, von Heinje G, Academic Press, (1987); and Sequence Analysis Primer, Gribskov M and Devereux J, eds., M Stockton Press, New York, (1991); and Carillo H and Lipman D, SIAM J. Applied Math., 48: 1073, (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux J et al.: *Nucleic Acids Res.* 12(1): 387, (1984)), BLASTP, BLASTN, and FASTA (Altschul S F et al.: *J. Molec. Biol.* 215: 403-410, (1990) and Altschul S F et al.: *Nucleic Acids Res.* 25: 3389-3402, (1997)). The BLAST X program is publicly available from NCBI and other sources (BLAST Manual, Altschul S F et al., NCBI NLM NIH Bethesda, Md. 20894; Altschul S F et al., *J. Mol. Biol.* 215: 403-410, (1990)). The well-known Smith Waterman algorithm (Smith T F, Waterman M S: *J. Mol. Biol.* 147(1): 195-197, (1981)) can also be used to determine similarity between sequences.

The term "insulin" includes all forms of insulin including, without limitation, rapid-acting forms, such as Insulin Lispro rDNA origin: HUMALOG (1.5 mL, 10 mL, Eli Lilly and Company, Indianapolis, Ind.), Insulin Injection (Regular Insulin) from beef and pork (regular ILETIN I, Eli Lilly), human: rDNA: HUMULIN R (Eli Lilly), NOVOLIN R (Novo Nordisk, New York, N.Y.), Semi synthetic: VELOSULIN Human (Novo Nordisk), rDNA Human, Buffered: VELOSULIN BR, pork: regular Insulin (Novo Nordisk), purified pork: Pork Regular ILETIN II (Eli Lilly), Regular Purified Pork Insulin (Novo Nordisk), and Regular (Concentrated) ILETIN II U-500 (500 units/mL, Eli Lilly); intermediate-acting forms such as Insulin Zinc Suspension, beef and pork: LENTE ILETIN G I (Eli Lilly), Human, rDNA: HUMULIN L (Eli Lilly), NOVOLIN L (Novo Nordisk), purified pork: LENTE ILETIN II (Eli Lilly), Isophane Insulin Suspension (NPH): beef and pork: NPH ILETIN I (Eli Lilly), Human, rDNA: HUMULIN N (Eli Lilly), Novolin N (Novo Nordisk), purified pork: Pork NPH Eetin II (Eli Lilly), NPH-N (Novo Nordisk); and long-acting forms such as Insulin zinc suspension, extended (ULTRALENTE, Eli Lilly), human, rDNA: HUMULIN U (Eli Lilly).

The terms "measuring" or "measurement" mean assessing the presence, absence, quantity, or amount (which can be an effective amount) of either a given substance within a clinical- or patient-derived sample, including the derivation of qualitative or quantitative concentration levels of such substances, or otherwise evaluating the values or categorization of a patient's clinical parameters.

The term "meal" as used herein means a standard and/or a mixed meal.

The term "mean", when preceding a pharmacokinetic value (e.g., mean $t_{max}$), represents the arithmetic mean value of the pharmacokinetic value unless otherwise specified.

The term "mean baseline level" as used herein means the measurement, calculation, or level of a certain value that is used as a basis for comparison, which is the mean value over a statistically significant number of subjects, e.g., across a single clinical study or a combination of more than one clinical study.

The term "multiple dose" means that the patient has received at least two doses of the drug composition in accordance with the dosing interval for that composition.

The term "neuropathy" in the context of a "patient with neuropathy" or a patient that "has neuropathy", means that the patient meets at least one of the four criteria outlined in the San Antonio Conference on diabetic neuropathy (Report and recommendations of the San Antonio Conference on diabetic neuropathy. Ann. Neurol. 24 99-104 (1988)), which in brief include 1) clinical signs of polyneuropathy, 2) symptoms of nerve dysfunction, 3) nerve conduction deficits in at least two nerves, or 4) quantitative sensory deficits. The term "established neuropathy" means that the patient meets at least two of the four criteria outlined in the San Antonio Conference on diabetic neuropathy. The term "incipient neuropathy" refers to a patient that exhibits only nerve conduction deficits, and no other symptoms of neuropathy.

The terms "nighttime" or "bedtime" as used herein means a time before the patient goes to sleep and is not limited to clock time or cycles of light and dark, and alternately refers to a time during a day or night of longest fast, a period without external glucose source. As used herein, the phrase administered "at nighttime" or "at or shortly before (prior to) bedtime" means administered less than about 3 hours, preferably less than about 2 hours, and more preferably less than about 1 hour prior to a prolonged period of sleep, or relative physical and/or mental inactivity, and fast, e.g., overnight. Whereas overnight typically means from the late night (p.m.) hours to the early morning (a.m.) hours, it could mean any period of a sleep-wake cycle during which a person obtains his/her necessary period of sleep. For the purposes of the present specification, administration should also occur at least about one hour, preferably at least about 1.5 hours, more preferably at least about 2 hours, and still more preferably at least about 2 to about 3 hours after the last meal of the day. As used herein, the phrase administered "at mealtime" or "at or shortly before (prior to) ingestion of a meal" means administered within about 30 minutes prior to the meal. For the purposes of the present specification, the administration is preferably within about 25 minutes, more preferably within about 20 minutes, even more preferably within about 15 minutes, still more preferably within about 10 minutes, further more preferably within about 5 minutes of ingestion of the meal, and most preferably administered concurrently with ingestion of the meal (within about 0 minutes).

The term "normal glucose levels" is used interchangeably with the term "normoglycemic" and "normal" and refers to a fasting venous plasma glucose concentration of less than about 6.1 mmoL/L (110 mg/dL). Sustained glucose levels above normoglycemic are considered a pre-diabetic condition.

As used herein, the term "patient" in the context of the present invention is preferably a mammal. The mammal can be a human, non-human primate, mouse, rat, dog, cat, horse, or cow, but are not limited to these examples. Mammals other than humans can be advantageously used as patients that represent animal models of insulin-dependent diabetes mellitus, or diabetic conditions. A patient can be male or female. A patient can be one who has been previously diagnosed or identified as having insulin-dependent diabetes, or a diabetic condition, and optionally has already undergone, or is undergoing, a therapeutic intervention for the diabetes. A patient can also be one who is suffering from a long-term complication of diabetes. Preferably the patient is human.

The term "replacement dose" in the context of a replacement therapy for C-peptide refers to a dose of C-peptide that maintains C-peptide levels in the blood within a desirable range, particularly at a level which is at or above the minimum effective therapeutic level. In another aspect, the replacement dose maintains the average steady-state concentration C-peptide levels above a minimum level of about 0.1 nM between dosing intervals. In a preferred aspect the replacement dose maintains the average steady state concentration C-peptide levels above a minimum level of about 0.2 nM between dosing intervals.

The term "risk" in the context of the present invention, relates to the probability that an event will occur over a specific time period, and can mean a patient's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low-risk cohorts or an average population risk, which can vary by how clinical risk factors are assessed. Odds ratios, the proportion of positive events to negative events for a given test result, are also commonly used (odds are according to the formula $p/(1-p)$, where p is the probability of event and $(1-p)$ is the probability of no event) to no-conversion. Alternative continuous measures that may be assessed in the context of the present invention include time to diabetes conversion and therapeutic diabetes conversion risk reduction ratios.

The term "risk evaluation" or "evaluation of risk" in the context of the present invention encompasses making a prediction of the probability, odds, or likelihood that an event may occur, the rate of occurrence of the event, i.e., from a normoglycemic condition to a hypoglycemic condition, or the development or frequency of hypoglycemic events.

A "sample" in the context of the present invention is a biological sample isolated from a patient and can include, by way of example and not limitation, whole blood, serum, plasma, blood cells, endothelial cells, tissue biopsies, lymphatic fluid, ascites fluid, interstitial fluid (also known as "extracellular fluid" and encompasses the fluid found in spaces between cells, including inter alia, gingival crevicular fluid), bone marrow, cerebrospinal fluid (CSF), saliva, mucous, sputum, sweat, urine, or any other secretion, excretion, or other bodily fluids. "Blood sample" refers to whole blood or any fraction thereof, including blood cells, serum, and plasma; serum is a preferred blood sample.

The term "Standard Deviation Score" or "SDS", when referring to nerve conduction velocity, refers to the observed value minus the mean of the reference value divided by the standard deviation of the method. The quantitative sensory testing (QST) data are presented as corrected for age. The reference values were estimated from linear regression analysis of data in a cohort of 63 healthy subjects (27 men and 36 women, 22-55 years of age, body height 150-196 cm).

The terms "subcutaneous" or "subcutaneously" or "S.C." in reference to a mode of administration of insulin or C-peptide, refers to a drug that is administered as a bolus injection, or via an implantable device into the area in, or below the subcutis, the layer of skin directly below the dermis and epidermis, collectively referred to as the cutis. Preferred sites for subcutaneous administration and/or implantation include the outer area of the upper arm, just above and below the waist, except the area right around the navel (a 2-inch circle). The upper area of the buttock, just behind the hipbone. The front of the thigh, midway to the outer side, 4 inches below the top of the thigh to 4 inches above the knee.

The term "single dose" means that the patient has received a single dose of the drug composition or that the repeated single doses have been administered with washout periods in between. Unless specifically designated as "single dose" or at "steady-state" the pharmacokinetic parameters disclosed and claimed herein encompass both single-dose and multiple-dose conditions.

The term "sequence similarity" refers to the degree of identity or correspondence between nucleic acid or amino acid sequences that may or may not share a common evolutionary origin (see Reeck et al., supra). However, in common usage and in the present application, the term "homologous", when modified with an adverb such as "highly", may refer to sequence similarity and may or may not relate to a common evolutionary origin.

By "statistically significant", it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

As defined herein, the terms "sustained release", "extended release", or "depot formulation" refers to the release of a drug such as C-peptide from the sustained release composition or sustained release device which occurs over a period which is longer than that period during which the C-peptide would be available following direct I.V. or S.C. administration of a single dose of C-peptide. In one aspect, sustained release will be a release that occurs over a period of at least about one to two weeks. In another aspect, sustained release will be a release that occurs over a period of at least about one year. The continuity of release and level of release can be affected by the type of sustained release device (e.g., programmable pump or osmotically-driven pump) or sustained release composition used (e.g., monomer ratios, molecular weight, block composition, and varying combinations of polymers), polypeptide loading, and/or selection of excipients to produce the desired effect, as more fully described herein.

Various sustained release profiles can be provided in accordance with any of the methods and kits of the present invention. "Sustained release profile" means a release profile in which less than 50% of the total release of C-peptide that occurs over the course of implantation/insertion or other method of administering C-peptide in the body occurs within the first 24 hours of administration. In a preferred embodiment of the present invention, the extended release profile is selected from the group consisting of; a) the 50% release point occurring at a time that is between 48 and 72 hours after implantation/insertion or other method of administration; b) the 50% release point occurring at a time that is between 72 and 96 hours after implantation/insertion or other method of administration; c) the 50% release point occurring at a time that is between 96 and 110 hours after implantation/insertion or other method of administration; d) the 50% release point occurring at a time that is between 1 and 2 weeks after implantation/insertion or other method of administration; e) the 50% release point occurring at a time that is between 2 and 4 weeks after implantation/insertion or other method of administration; f) the 50% release point occurring at a time that is between 4 and 8 weeks after implantation/insertion or other method of administration; g) the 50% release point occurring at a time that is between 8 and 16 weeks after implantation/insertion or other method of administration; h) the 50% release point occurring at a time that is between 16 and 52 weeks (1 year) after implantation/insertion or other method of administration; and i) the 50% release point occurring at a time that is between 52 and 104 weeks after implantation/insertion or other method of administration.

Additionally, use of a sustained release composition can reduce the degree of fluctuation ("DFL") of C-peptide's plasma concentration. DFL is a measurement of how much the plasma levels of a drug vary over the course of a dosing interval ($C_{max}$–$C_{min}$/$C_{min}$). For simple cases, such as I.V. administration, fluctuation is determined by the relationship between the elimination half-life ($t_{1/2}$) and dosing interval. If the dosing interval is equal to the half-life then the trough concentration is exactly half of the peak concentration, and the degree of fluctuation is 100%. Thus a sustained release composition with a reduced DFL (for the same dosing interval) signifies that the difference in peak and trough plasma levels has been reduced. Preferably, the patients receiving a sustained release composition of C-peptide have a DFL approximately 50%, 40%, or 30% of the DFL in patients receiving a non-extended release composition with the same dosing interval.

The terms "treating" or "treatment" means to relieve, alleviate, delay, reduce, reverse, improve, manage, or prevent at least one symptom of a condition in a patient. The term "treating" may also mean to arrest, delay the onset (i.e., the period prior to clinical manifestation of a disease), and/or reduce the risk of developing or worsening a condition.

As used herein, the terms "therapeutically effective amount", "prophylactically effective amount", or "diagnostically effective amount" is the amount of the drug, e.g., insulin or C-peptide, needed to elicit the desired biological response following administration.

The term "Unit-Dose Forms" refers to physically discrete units suitable for human and animal patients and packaged individually as is known in the art. It is contemplated for purposes of the present invention that dosage forms of the present invention comprising therapeutically effective amounts of C-peptide may include one or more unit doses (e.g., tablets, capsules, powders, semisolids [e.g., gelcaps or films], liquids for oral administration, ampoules or vials for injection, loaded syringes) to achieve the therapeutic effect. It is further contemplated for the purposes of the present invention that a preferred embodiment of the dosage form is a subcutaneously injectable dosage form.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the compositions can mean plus or minus a range of up to 20%, preferably up to 10%, more preferably up to 5%.

As used herein and in the appended claims, the singular forms "a", "an", and "the" include plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods and kits described herein.

Unless defined otherwise, all technical and scientific terms used herein have the same meaning as commonly understood by one of ordinary skill in the art to which the invention belongs. Although any methods, compositions, reagents, cells, similar or equivalent to those described herein can be used in the practice or testing of the invention, the preferred methods and materials are described herein. All publications mentioned herein are incorporated herein, including all figures, graphs, equations, illustrations, and drawings, to describe and disclose specific information for which the reference was cited in connection with.

The publications discussed above are provided solely for their disclosure before the filing date of the present application. Nothing herein is to be construed as an admission that the invention is not entitled to antedate such disclosure by virtue of prior invention.

Overview of Methods and Kits for Reducing the Risk of Hypoglycemia

The present invention relates to the development of improved methods and kits for treating the long-term complication of diabetes that reduce the risk of the patient developing hypoglycemia during or when starting C-peptide therapy. Significantly, such improved dosing regimens also maintain good glycemic control, and avoid excessive weight gain that may otherwise be associated with excessive insulin administration or caloric intake during C-peptide therapy. In one aspect, these methods may be applied to patients with neuropathy who exhibit altered sensitivity to hypoglycemia and reduced insulin usage during C-peptide therapy.

Thus in one aspect, the present invention includes a method for treating an insulin-dependent human patient, comprising the steps of; a) administering insulin to said patient, wherein said patient has neuropathy; b) administering subcutaneously to said patient a therapeutic dose of C-peptide in a different site as that used for said patient's insulin administration; c) adjusting the dosage amount, type, or frequency of insulin administered based on monitoring said patient's altered insulin requirements resulting from said therapeutic dose of C-peptide, wherein said adjusted dose of insulin reduces the risk, incidence, or severity of hypoglycemia, wherein said adjusted dose of insulin is at least 10% less than said patient's insulin dose prior to starting C-peptide treatment.

In one aspect of this method, the hypoglycemia is severe hypoglycemia. In another aspect of this method, the hypoglycemia is asymptomatic hypoglycemia.

In another aspect, the present invention includes a method of reducing insulin usage in an insulin-dependent human patient, comprising the steps of; a) administering insulin to said patient, wherein said patient has neuropathy; b) administering subcutaneously to said patient a therapeutic dose of C-peptide in a different site as that used for said patient's insulin administration; c) adjusting the dosage amount, type, or frequency of insulin administered based on monitoring said patient's altered insulin requirements resulting from said therapeutic dose of C-peptide, wherein said adjusted dose of insulin does not induce hyperglycemia, wherein said adjusted dose of insulin is at least 10% less than said patient's insulin dose prior to starting C-peptide treatment.

In another aspect, the present invention comprises a method for treating an insulin-dependent patient without substantially increasing the risk, incidence, or severity of hypoglycemia in comprising the steps of; a) administering insulin to the patient; b) administering subcutaneously to the patient a therapeutic dose of C-peptide in a different site as that used for the patient's insulin administration; and c) adjusting the dosage amount, type, or frequency of insulin administered with the therapeutic dose of C-peptide based on the patient's altered insulin requirements.

In another embodiment, the present invention includes a method of reducing insulin usage in an insulin-dependent patient without inducing hyperglycemia comprising the steps of; a) administering insulin to the patient; b) administering subcutaneously to the patient a therapeutic dose of C-peptide in a different site as that used for the patient's insulin administration; and c) adjusting the dosage amount, type, or frequency of insulin administered with the therapeutic dose of C-peptide based on said patient's altered insulin requirements.

In another embodiment, the present invention includes a method for reducing weight gain in an insulin-dependent patient comprising the steps of; a) administering insulin to the patient; b) administering subcutaneously to the patient a therapeutic dose of C-peptide in a different site as that used for the patient's insulin administration; and c) adjusting the dosage amount, type, or frequency of insulin administered with the therapeutic dose of C-peptide based on the patient's altered insulin requirements.

In a further embodiment, the invention includes a method for identifying patients that respond to C-peptide by a change in insulin requirements by monitoring the patient to determine the patient's basal C-peptide levels prior to starting C-peptide therapy.

In an additional embodiment, the invention includes a method for identifying patients that respond to C-peptide by a change in insulin requirements by monitoring the patient to determine the patient's change in nerve conduction velocity during C-peptide treatment.

In an additional further embodiment, the invention includes a method for identifying patients that respond to C-peptide by a change in insulin requirements by monitoring the patient to determine the patient's change in autonomic nerve function during C-peptide treatment.

In one further embodiment, the present invention includes a method for the treatment of a patient with a long-term complication of diabetes by C-peptide which minimizes the risk of the patient developing hypoglycemia, comprising the steps of; a) monitoring one or more clinical parameters, biomarkers, or analytes from the patient and/or monitoring the patient's insulin usage over a baseline period prior to starting C-peptide therapy; b) administering a therapeutically effective dose of C-peptide for an evaluation period; c) re-monitoring one or more of the clinical parameters, biomarkers, or analytes and/or re-monitoring the patient's insulin usage over the evaluation period to determine a new reference range of parameters; and d) reducing the dose, frequency, or type of insulin administration based on a comparison of the baseline reference range and new reference range of the parameters.

In another embodiment, the present invention includes a method for the treatment for a long-term complication of type 1 diabetes via treatment with C-peptide, which reduces the risk of the patient developing hypoglycemia during the therapy, comprising the steps of; a) monitoring one or more clinical parameters, biomarkers, or analytes and/or monitoring the patient's insulin usage over an evaluation period of C-peptide therapy to determine a reference range of insulin sensitivity for the patient when treated with C-peptide; and b) reducing the dose, frequency, or type of insulin administration based on a comparison of the patient's clinical parameters, biomarkers, or analytes obtained during the evaluation period compared to an index reference range of parameters for that patient.

In a further embodiment, the present invention includes a method for the treatment of a long-term complication of type 1 diabetes via treatment with C-peptide which reduces the risk of the patient developing hypoglycemia during the therapy, of comprising the steps of; a) monitoring at least the incidence of hypoglycemic events experienced by the patient during an evaluation period of C-peptide therapy; and b) reducing the average daily requirement of insulin administered to the patient calculated prior to starting C-peptide therapy by about 5% to about 50% if the incidence of hypoglycemic events observed during the evaluation period of C-peptide therapy is increased compared to the incidence of hypoglycemic events observed prior to starting C-peptide therapy.

In another embodiment, the present invention includes a method for reducing the risk of a patient with insulin-dependent diabetes developing hypoglycemia when treated with C-peptide comprising the steps of; a) assessing the patient's C-peptide levels prior to starting C-peptide therapy; and b) reducing the average daily dose of insulin administered to the patient by about 10% to about 35%.

In another embodiment, the present invention includes a method for reducing weight gain in a patient with insulin-dependent diabetes when treated with C-peptide comprising the steps of; a) assessing the patient's C-peptide levels prior to starting C-peptide therapy; and b) reducing the average daily dose of insulin administered to the patient by about 10% to about 35%.

In another embodiment, the present invention includes a method for the treatment of a patient with insulin-dependent diabetes who is starting a therapy of a long-term complication of type 1 diabetes via treatment with C-peptide which reduces the risk of the patient developing hypoglycemia, comprising the steps of; a) assessing the patient's average daily requirement of insulin including number of international units of short-, intermediate-, and long-acting insulin that the patient administers prior to starting C-peptide therapy; b) administering subcutaneously to the patient a therapeutically effective dose of C-peptide for a lead-in period; and c) independently reducing the average daily requirement of either short-, intermediate-, or long-acting insulin administered to the patient by about 5% to about 50% compared to the amount administered prior to starting C-peptide therapy.

Insulin-Dependent Diabetes

In any of the methods and kits disclosed herein, the terms "insulin-dependent patient" or "insulin-dependent diabetes" encompasses all forms of diabetics/diabetes who/that require insulin administration to adequately maintain normal glucose levels.

In broad terms, the term "diabetes" refers to the situation where the body either fails to properly respond to its own insulin, does not make enough insulin, or both. The primary result of impaired insulin production is the accumulation of glucose in the blood, and a C-peptide deficiency leading to various short- and long-term complications. Three principal forms of diabetes exist:

Type 1: Results from the body's failure to produce insulin and C-peptide. It is estimated that 5-10% of Americans who are diagnosed with diabetes have type 1 diabetes. Presently almost all persons with type 1 diabetes must take insulin injections. The term "type 1 diabetes" has replaced several former terms, including childhood-onset diabetes, juvenile diabetes, and insulin-dependent diabetes mellitus (IDDM). For patients with type 1 diabetes, basal levels of C-peptide are typically less than about 0.20 nM (Ludvigsson et al.: *New Engl. J. Med.* 359: 1909-1920, (2008)).

Type 2: Results from tissue insulin resistance, a condition in which cells fail to respond properly to insulin, sometimes combined with relative insulin deficiency. The term "type 2 diabetes" has replaced several former terms, including adult-onset diabetes, obesity-related diabetes, and non-insulin-dependent diabetes mellitus (NIDDM). For type 2 patients in the basal state, C-peptide levels of about 0.8 nM (range 0.64 to 1.56 nM), and glucose stimulated levels of about 5.7 nM (range 3.7 to 7.7 nM) have been reported. (Retnakaran R et al.: *Diabetes Obes. Metab.* (2009) DOI 10.11 111/j.1463-1326.2009.01129.x; Zander et al.: *Lancet* 359: 824-830, (2002)).

Gestational diabetes: Pregnant women who have never had diabetes before but who have high blood sugar (glucose) levels during pregnancy are said to have gestational diabetes. Gestational diabetes affects about 4% of all pregnant women. It may precede development of type 2 (or rarely type 1).

Several other forms of diabetes mellitus are categorized separately from these. Examples include congenital diabetes due to genetic defects of insulin secretion, cystic fibrosis-related diabetes, steroid diabetes induced by high doses of glucocorticoids, and several forms of monogenic diabetes.

Acute complications of diabetes include hypoglycemia, diabetic ketoacidosis, or nonketotic hyperosmolar coma that may occur if the disease is not adequately controlled. Serious long-term complications can also occur, and are discussed in more detail below.

Long-Term Complications of Diabetes

In any of these methods and kits, the terms "long-term complication of type 1 diabetes", or "long-term complications of diabetes" refers to the long-term complications of impaired glycemic control, and C-peptide deficiency associated with insulin-dependent diabetes. Accordingly in any of these methods and kits, the patient may be being treated for a long-term complication of diabetes. Typically long-term complications of type 1 diabetes are associated with type 1 diabetics. However the term can also refer to long-term complications of diabetes that arise in type 1.5 and type 2 diabetic patients who develop a C-peptide deficiency as a consequence of losing pancreatic islet β-cells and therefore also become insulin dependent. In broad terms, many such complications arise from the primary damage of blood vessels (angiopathy), resulting in subsequent problems that can be grouped under "microvascular disease" (due to damage to small blood vessels) and "macrovascular disease" (due to damage to the arteries).

Specific diseases and disorders included within the term long-term complications of diabetes include, without limitation; retinopathy including early stage retinopathy with microaneurysms, proliferative retinopathy, and macular edema; peripheral neuropathy including sensorimotor polyneuropathy, painful sensory neuropathy, acute motor neuropathy, cranial focal and multifocal polyneuropathies, thoracolumbar radiculoneuropathies, proximal diabetic neuropathies, and focal limb neuropathies including entrapment and compression neuropathies; autonomic neuropathy involving the cardiovascular system, the gastrointestinal tract, the respiratory system, the urigenital system, sudomotor function, and papillary function; and nephropathy including disorders with microalbuminuria, overt proteinuria, and end-stage renal disease.

Impaired microcirculatory perfusion appears to be crucial to the pathogenesis of both neuropathy and retinopathy in diabetics. This in turn reflects a hyperglycemia-mediated perturbation of vascular endothelial function that results in: overactivation of protein kinase C, reduced availability of nitric oxide (NO), increased production of superoxide and endothelin-1 (ET-1), impaired insulin function, diminished synthesis of prostacyclin/PGE1, and increased activation and endothelial adherence of leukocytes. This is ultimately a catastrophic group of clinical events.

Diabetic retinopathy is an ocular manifestation of the systemic damage to small blood vessels leading to microangiopathy. In retinopathy, growth of friable and poor-quality new blood vessels in the retina as well as macular edema (swelling of the macula) can lead to severe vision loss or blindness. As new blood vessels form at the back of the eye as a part of proliferative diabetic retinopathy (PDR), they can bleed (hemorrhage) and blur vision. It affects up to 80% of all patients who have had diabetes for 10 years or more.

The symptoms of diabetic retinopathy are often slow to develop and subtle and include blurred version and progressive loss of sight. Macular edema, which may cause vision loss more rapidly, may not have any warning signs for some time. In general, however, a person with macular edema is likely to have blurred vision, making it hard to do things like read or drive. In some cases, the vision will get better or worse during the day.

Accordingly in any of these methods and kits, a patient who is in need of treatment for a long-term complication of diabetes can include a patient with one of more of the symptoms of diabetic retinopathy.

Diabetic neuropathies are neuropathic disorders that are associated with diabetic microvascular injury involving small blood vessels that supply nerves (vasa nervorum). Relatively common conditions which may be associated with diabetic neuropathy include third nerve palsy; mononeuropathy; mononeuropathy multiplex; diabetic amyotrophy; a painful polyneuropathy; peripheral neuropathy; autonomic neuropathy; and thoracoabdominal neuropathy.

Diabetic neuropathy affects all peripheral nerves: pain fibers, motor neurons, autonomic nerves. It therefore necessarily can affect all organs and systems since all are innervated. There are several distinct syndromes based on the organ systems and members affected, but these are by no means exclusive. A patient can have sensorimotor and autonomic neuropathy or any other combination. Symptoms vary depending on the nerve(s) affected and may include symptoms other than those listed. Symptoms usually develop gradually over years.

Symptoms of diabetic neuropathy may include: numbness and tingling of extremities, dysesthesia (decreased or loss of sensation to a body part), diarrhea, erectile dysfunction, urinary incontinence (loss of bladder control), impotence, facial, mouth and eyelid drooping, vision changes, dizziness, muscle weakness, difficulty swallowing, speech impairment, fasciculation (muscle contractions), anorgasmia, and burning or electric pain.

Additionally, different nerves are affected in different ways by neuropathy. Sensorimotor polyneuropathy, in which longer nerve fibers are affected to a greater degree than shorter ones, because nerve conduction velocity is slowed in proportion to a nerve's length. In this syndrome, decreased sensation and loss of reflexes occurs first in the toes on each foot, then extends upward. It is usually described as glove-stocking distribution of numbness, sensory loss, dysesthesia, and nighttime pain. The pain can feel like burning, pricking sensation, achy, or dull. Pins and needles sensation is common. Loss of proprioception, the sense of where a limb is in space, is affected early.

These patients cannot feel when they are stepping on a foreign body, like a splinter, or when they are developing a callous from an ill-fitting shoe. Consequently, they are at risk for developing ulcers and infections on the feet and legs, which can lead to amputation. Similarly, these patients can get multiple fractures of the knee, ankle, or foot, and develop a Charcot joint. Loss of motor function results in dorsiflexion, contractures of the toes, loss of the interosseous muscle function, and leads to contraction of the digits, so called hammer toes. These contractures occur not only in the foot, but also in the hand where the loss of the musculature makes the hand appear gaunt and skeletal. The loss of muscular function is progressive.

Autonomic neuropathy impacts the autonomic nervous system serving the heart, gastrointestinal system, and genitourinary system. The most commonly recognized autonomic dysfunction in diabetics is orthostatic hypotension, or fainting when standing up. In the case of diabetic autonomic neuropathy, it is due to the failure of the heart and arteries to appropriately adjust heart rate and vascular tone to keep blood continually and fully flowing to the brain. This symptom is usually accompanied by a loss of the usual change in heart rate seen with normal breathing. These two findings suggest autonomic neuropathy.

Gastrointestinal system symptoms include delayed gastric emptying, gastroparesis, nausea, bloating, and diarrhea. Because many diabetics take oral medication for their diabetes, absorption of these medicines is greatly affected by the delayed gastric emptying. This can lead to hypoglycemia when an oral diabetic agent is taken before a meal and does not get absorbed until hours, or sometimes days later, when there is normal or low blood sugar already. Sluggish movement of the small intestine can cause bacterial overgrowth, made worse by the presence of hyperglycemia. This leads to bloating, gas, and diarrhea.

Genitourinary system symptoms include urinary frequency, urgency, incontinence, and retention. Urinary retention can lead to bladder diverticula, stones, reflux nephropathy, and frequent urinary tract infections.

Cranial neuropathy occurs when cranial nerves are affected, and oculomotor (3rd) neuropathies are most commonly observed. The oculomotor nerve controls all of the muscles that move the eye with the exception of the lateral rectus and superior oblique muscles. It also serves to constrict the pupil and open the eyelid. The onset of a diabetic third nerve palsy is usually abrupt, beginning with frontal or periorbital pain and then diplopia. All of the oculomotor muscles innervated by the third nerve may be affected, except for those that control pupil size. This is because pupillary function within the oculomotor nerve (CNIII) is found on the periphery of the nerve (in terms of a cross sectional view), which makes it less susceptible to ischemic damage (as it is closer to the vascular supply).

The sixth nerve, the abducens nerve, which innervates the lateral rectus muscle of the eye (moves the eye laterally), is also commonly affected but the fourth nerve, the trochlear nerve (innervates the superior oblique muscle, which moves the eye downward), involvement is unusual. Mononeuropathies of the thoracic or lumbar spinal nerves can occur and lead to painful syndromes that mimic myocardial infarction, cholecystitis, or appendicitis. Diabetics have a higher incidence of entrapment neuropathies.

Accordingly in any of these methods and kits, the insulin-dependent patient in need of treatment for a long-term complication of diabetes includes a patient with one of more of the symptoms of diabetic neuropathy. In another aspect of the claimed methods, the patient has neuropathy, and in one aspect the patient has incipient neuropathy, and in one aspect the patient has established neuropathy.

Diabetic nephropathy is a progressive kidney disease caused by angiopathy of capillaries in the kidney glomeruli. It is characterized by nephrotic syndrome and diffuse glomerulosclerosis. It is due to long-standing diabetes mellitus, and is a prime cause for dialysis in many Western countries.

The symptoms of diabetic nephropathy can be seen in patients with chronic diabetes (15 years or more after onset). The disease is progressive and is more frequent in men. Diabetic nephropathy is the most common cause of chronic kidney failure and end-stage kidney disease in the United States. People with both type 1 and type 2 diabetes are at risk. The risk is higher if blood-glucose levels are poorly controlled. Further, once nephropathy develops, the greatest rate of progression is seen in patients with poor control of their blood pressure. Also people with high cholesterol level in their blood have much more risk than others.

The earliest detectable change in the course of diabetic nephropathy is an abnormality of the glomerular filtration barrier. At this stage, the kidney may start allowing more serum albumin than normal in the urine (albuminuria), and this can be detected by sensitive medical tests for albumin. This stage is called "microalbuminuria". As diabetic nephropathy progresses, increasing numbers of glomeruli are destroyed by nodular glomerulosclerosis. Now the amounts of albumin being excreted in the urine increases, and may be detected by ordinary urinalysis techniques. At this stage, a kidney biopsy clearly shows diabetic nephropathy.

Kidney failure provoked by glomerulosclerosis leads to fluid filtration deficits and other disorders of kidney function. There is an increase in blood pressure (hypertension) and fluid retention in the body plus a reduced plasma oncotic pressure causes edema. Other complications may be arteriosclerosis of the renal artery and proteinuria.

Throughout its early course, diabetic nephropathy has no symptoms. They develop in late stages and may be a result of excretion of high amounts of protein in the urine or due to renal failure. Symptoms include, edema: swelling, usually around the eyes in the mornings; later, general body swelling may result, such as swelling of the legs, foamy appearance or excessive frothing of the urine (caused by the proteinura), unintentional weight gain (from fluid accumulation), anorexia (poor appetite), nausea and vomiting, malaise (general ill feeling), fatigue, headache, frequent hiccups, and generalized itching.

Accordingly in any of these methods and kits, a patient who is in need of treatment for a long-term complication of diabetes can include a patient with one of more of the symptoms of diabetic nephropathy.

Diabetic cardiomyopathy (DCM), damage to the heart, leading to diastolic dysfunction and eventually heart failure. Aside from large vessel disease and accelerated atherosclerosis, which is very common in diabetes, DCM is a clinical condition diagnosed when ventricular dysfunction develops in patients with diabetes in the absence of coronary atherosclerosis and hypertension. DCM may be characterized functionally by ventricular dilation, myocyte hypertrophy, prominent interstitial fibrosis, and decreased or preserved systolic function in the presence of a diastolic dysfunction.

One particularity of DCM is the long latent phase, during which the disease progresses but is completely asymptomatic. In most cases, DCM is detected with concomitant hypertension or coronary artery disease. One of the earliest signs is mild left ventricular diastolic dysfunction with little effect on ventricular filling. Also, the diabetic patient may show subtle signs of DCM related to decreased left ventricular compliance or left ventricular hypertrophy or a combination of both. A prominent "a" wave can also be noted in the jugular venous pulse, and the cardiac apical impulse may be overactive or sustained throughout systole. After the development of systolic dysfunction, left ventricular dilation and symptomatic heart failure, the jugular venous pressure may become elevated and the apical impulse would be displaced downward and to the left. Systolic mitral murmur is not uncommon in these cases.

These changes are accompanied by a variety of electrocardiographic changes that may be associated with DCM in 60% of patients without structural heart disease, although usually not in the early asymptomatic phase. Later in the progression, a prolonged QT interval may be indicative of fibrosis. Given that DCM's definition excludes concomitant atherosclerosis or hypertension, there are no changes in perfusion or in atrial natriuretic peptide levels up until the very late stages of the disease, when the hypertrophy and fibrosis become very pronounced.

Macrovascular diseases of diabetes include coronary artery disease, leading to angina or myocardial infarction ("heart attack"), stroke (mainly the ischemic type), peripheral vascular disease, which contributes to intermittent claudication (exertion-related leg and foot pain), as well as diabetic foot and diabetic myonecrosis ("muscle wasting").

Hypoglycemia and Hypoglycemic Events

In any of these methods and kits, the term "hypoglycemia" or "hypoglycemic events" refers to all episodes of abnormally low plasma glucose concentration that exposes the patient to potential harm. The American Diabetes Association Workgroup has recommended that people with insulin-dependent diabetes become concerned about the possibility of developing hypoglycemia at a plasma glucose concentration of less than 70 mg/dL (3.9 mmoL/L). Accordingly in one aspect of any of the claimed methods and kits, the terms hypoglycemia or hypoglycemic event refers to the situation where the plasma glucose concentration of the patient drops to less than about 70 mg/dL (3.9 mmoL/L).

Hypoglycemia is a serious medical complication in the treatment of diabetes, and causes recurrent morbidity in most people with type 1 diabetes and many with advanced type 2 diabetes and is sometimes fatal. In addition, hypoglycemia compromises physiological and behavioral defenses against subsequent falling plasma glucose concentrations and thus causes a vicious cycle of recurrent hypoglycemia. Accordingly the prevention of hypoglycemia is of significant importance in the treatment of diabetes, as well as the treatment of the long-term complications of diabetes.

Unfortunately hypoglycemia is a fact of life for most people with type 1 diabetes (Cryer P E et al.: *Diabetes* 57: 3169-3176, (2008)). The average patient has untold numbers of episodes of asymptomatic hypoglycemia and suffers two episodes of symptomatic hypoglycemia per week, with thousands of such episodes over a lifetime of diabetes. He or she suffers one or more episodes of severe, temporarily disabling hypoglycemia often with seizure or coma, per year.

Overall, hypoglycemia is less frequent in type 2 diabetes; however, the risk of hypoglycemia becomes progressively more frequent and limiting to glycemic control later in the course of type 2 diabetes. The prospective, population-based data of Donnelly et al. (*Diabetes Med.* 22: 749-755, (2005)) indicate that the overall incidence of hypoglycemia in insulin-treated type 2 diabetes is approximately one third of that in type 1 diabetes. The incidence of any hypoglycemia and of severe hypoglycemia was 4,300 and 115 episodes per 100 patient years, respectively, in type 1 diabetes and 1600 and 35 episodes per 100 patient years, respectively, in insulin-treated type 2 diabetes.

Hypoglycemia may be classified based on the severity of the hypoglycemic event. For example, the American Diabetes Association Workgroup has suggested the following classification of hypoglycemia in diabetes: 1) severe hypoglycemia (i.e., hypoglycemic coma requiring assistance of another person); 2) documented symptomatic hypoglycemia (with symptoms and a plasma glucose concentration of less than 70 mg/dL); 3) asymptomatic hypoglycemia (with a plasma glucose concentration of less than 70 mg/dL without symptoms); 4) probable symptomatic hypoglycemia (with symptoms attributed to hypoglycemia, but without a plasma glucose measurement); and 5) relative hypoglycemia (with a plasma glucose concentration of greater than 70 mg/dL but falling towards that level).

Thus in another aspect of any of the methods and kits disclosed herein, the term "hypoglycemia" refers to severe hypoglycemia, and/or hypoglycemic coma. In another aspect of any of these methods and kits, the term "hypoglycemia" refers to symptomatic hypoglycemia. In another aspect of any of these methods and kits, the term "hypoglycemia" refers to probable symptomatic hypoglycemia. In another aspect of any of these methods and kits, the term "hypoglycemia" refers to asymptomatic hypoglycemia. In another aspect of any of these methods and kits, the term "hypoglycemia" refers to relative hypoglycemia.

Although hypoglycemic events are typically associated with symptoms, the signs of hypoglycemia are not specific. Thus, clinical hypoglycemia is most convincingly documented by a combination of: 1) symptoms, signs, or both consistent with hypoglycemia, 2) a low measured plasma glucose concentration, and 3) resolution of these symptoms and signs after the plasma glucose concentration is raised.

Symptoms of hypoglycemia are categorized as neuroglycopenic (those that are the direct result of brain glucose deprivation per se) and neurogenic (or autonomic), and those that are largely the result of the perception of physiological changes caused by the sympathoadrenal (largely the sympathetic neural discharge triggered by hypoglycemia). Neuroglycopenic manifestations include cognitive impairments, behavioral changes, and psychomotor abnormalities, and, at lower plasma glucose concentrations, seizure and coma.

Adrenergic neurogenic symptoms include palpitations, tremor, and anxiety/arousal. Cholingeric neurogenic symptoms include sweating, hunger, and paresthesias. Central, as well as peripheral mechanisms may be involved in the generation of some symptoms such as hunger. Awareness of hypoglycemia is largely the result of the perception of the neurogenic symptoms. Pallor and diaphoresis (the result of adrenergic cutaneous vasoconstriction and cholinergic stimulation of sweat glands, respectively) are common signs of hypoglycemia.

Accordingly in one aspect of any of the methods and kits disclosed herein, hypoglycemic events may be determined by monitoring one or more of the symptoms of hypoglycemia. In one aspect, or any of these methods and kits, the symptoms of hypoglycemia can be selected from palpitations, tremor, anxiety/arousal, sweating, hunger, and paresthesias. In a preferred aspect, hypoglycemia may be determined by measuring or monitoring the patient's blood glucose levels.

In another aspect of any of the claimed methods and kits, a patient undergoing or initiating C-peptide therapy may be evaluated for one or more risk factors for developing hypoglycemia.

Conventional risk factors for hypoglycemia in diabetes include:

Insulin or insulin secretagogue doses are excessive, ill-timed, or of a wrong type.

Exogenous glucose delivery is decreased (e.g., following missed meals and during the overnight fast).

Glucose utilization is increased (e.g., during and shortly after exercise).

Endogenous glucose production is decreased (e.g., following alcohol ingestion).

Sensitivity to insulin is increased (e.g., in the middle of the night and following weight loss, improved fitness, or improved glycemic control).

Insulin clearance is decreased (e.g., with renal failure).

Additionally, recent antecedent hypoglycemia, as well as prior exercise or sleep, causes both defective glucose counter regulation and hypoglycemia unawareness and therefore, a vicious cycle of recurrent iatrogenic hypoglycemia referred to as hypoglycemia-associated autonomic failure (HAAF).

Accordingly in one aspect of any of the claimed methods and kits, one or more risk factors for hypoglycemia may be monitored. In one aspect of these methods and kits, the risk factors for hypoglycemia may be monitored prior to initiating C-peptide therapy. In another aspect, the risk factors may be monitored during an evaluation period of C-peptide therapy.

The risk factors indicative of HAAF include the degree of endogenous insulin deficiency; a history of severe hypoglycemia, hypoglycemia unawareness, or both as well as recent antecedent hypoglycemia, prior exercise, or sleep, and lower mean glycemic associated with aggressive glycemic therapy per se (lower HbA1c levels, lower glycemic goals).

Accordingly in another aspect of any of the methods and kits disclosed herein the risk of hypoglycemia events may be assessed by monitoring one or more of the risk factors of hypoglycemia or HAAF.

Methods for Monitoring Patient Parameters and Determination of Risk Factors

An assessment of one or more biomarkers, analytes, and clinical parameters in any of the claimed methods and kits of the invention allows one of skill in the art to identify and assess those patients who respond to C-peptide therapy with an increase in insulin sensitivity, and who are therefore at risk for developing hypoglycemia, or for excessive weight gain.

Effective regulation of glucose levels and the prevention of hypoglycemia however are ultimately dependent on modifying human behavior. Consequently, people with diabetes face a life-long behaviorally controlled optimization problem to reduce hyperglycemic excursions and maintain strict glycemic control, without increasing their risk for hypoglycemia. While intensive treatment with insulin to maintain nearly normal levels of glucose markedly reduces the incidence of long-term complications of diabetes, this approach may also increase the risk of severe hypoglycemia. Additionally, the present invention recognizes for the first time that co-treatment with C-peptide may present the patient with an additional risk of developing a hypoglycemia coma caused by a C-peptide-mediated reduction in insulin requirements in a subset of patients. Accordingly, the development of hypoglycemia can be considered a primary barrier to the successful treatment of the long-term complications of diabetes with C-peptide.

The warning symptoms and hormonal defenses against hypoglycemia are typically attenuated in type 1 diabetes, and may be particularly problematic in patients that have suffered from diabetes for several years and who are therefore at increased risk of, or have, one or more long-term complications of diabetes. Accordingly, the present invention provides methods for monitoring and assessing a patient's risk of hypoglycemia by providing one or more periods of evaluation of the patient either prior to, during, or as the patient starts C-peptide therapy.

In one aspect, the present invention is based on the discovery that patients who exhibit a reduced severity of peripheral neuropathy relative to their duration of disease, may respond more effectively to C-peptide therapy, and are therefore at increased risk of developing hypoglycemia. Accordingly in one aspect, disease severity may be monitored by measuring or assessing the patient's height-adjusted sensory or motor nerve conduction velocity. In one aspect of this method, initial nerve conduction velocity is assessed. In another embodiment, peak nerve conduction velocity is assessed. In another aspect of any of the claimed methods and kits, patients are identified to be at risk of developing hypoglycemia based on their baseline nerve conduction velocity, and taking into account their length of disease duration. In one aspect, identification is based on the patient exhibiting a peak nerve conduction velocity that is at least about 2 standard deviations from the mean peak nerve conduction velocity for a similar height-matched patient group comprising patients that have had insulin-dependent diabetes for a comparable time. In one aspect, the patients with a disease duration of about 30 years are selected with a peak nerve conduction velocity of greater than about 35 m/s. In one aspect of any of the claimed methods and kits, the patients are selected with a peak nerve conduction velocity of greater than about 40 m/s. In one aspect, the patients are selected with a peak nerve conduction velocity of greater than about 45 m/s. In one aspect, the patients are selected with a peak nerve conduction velocity of greater than about 50 m/s. In another aspect of any of the claimed methods and kits, the patients are selected based on their relative improvement in nerve conduction velocity.

In one aspect of any of the claimed methods and kits, patients are selected based on exhibiting an improvement in nerve conduction velocity of greater than about 1.5 m/s after starting C-peptide therapy. In another aspect of these methods and kits, patients are selected based on exhibiting an improvement in nerve conduction velocity of greater than about 2 m/s after starting C-peptide.

In embodiment of any of the claimed methods and kits, the patient is monitored over a baseline period prior to initiating C-peptide therapy. In one aspect, monitoring involves measuring, monitoring, or assessing a change in a biomarker, analyte, or clinical parameter in a patient starting C-peptide therapy. In one aspect, such monitoring is conducted by the patient. In another aspect, the results are downloaded to a computer or PC for data analysis at a remote site.

In one aspect of any of the claimed methods and kits, the analyte is selected from blood glucose concentration, glycosylated hemoglobin level, C-peptide, and insulin concentration and/or usage. In one aspect of these methods and kits, an assessment of insulin usage can include an assessment of the type of insulin administered, as well as the type, timing, and mode of administration.

In one aspect of any of these methods and kits, a computer is used to capture long-term trends towards increased risk for hypoglycemia. In one aspect of these methods and kits, a computer program may be used to identify periods of increased risk for hypoglycemia that may be associated with C-peptide therapy. These analyses may be based on specific algorithms that enable the comprehensive evaluation of glycemic control. (See generally, e.g., US Patent Application No. 20080154513 entitled, "Systems, Methods and Computer Program Codes for Recognition of Patterns of Hyperglycemia and Hypoglycemia, Increased Glucose Variability, and Ineffective Self-Monitoring in Diabetes".)

In one aspect of any of the claimed methods and kits, blood glucose concentrations are determined by the patient by self-monitoring of blood glucose (SMBG). Contemporary home blood glucose meters offer convenient means for frequent and accurate blood glucose determinations through self-monitoring of blood glucose. Most meters are capable of storing hundreds of SMBG readings, together with the date and time of each reading, and have interfaces to download these readings into a PC. The meters are usually accompanied by software that has capabilities for basic data analyses (e.g., calculation of mean blood glucose [BG], estimates of the average BG over the previous two weeks, percentages in target, hypoglycemic, and hyperglycemic zones, etc.), log of the data, and graphical representation (e.g., histograms, pie charts).

In another aspect of any of these methods and kits, glycosylated hemoglobin levels are determined. Glycosylated hemoglobin includes three components; namely, HbA1a, HbA1b, and HbA1c. It has been shown that a normal level of HbA1c in a diabetic patient's blood is a good indication that the treatment regime is effective and the risk of secondary complications of diabetes is low. The level of HbA1c in a healthy person's blood is between 4% and 6% of the total hemoglobin while in a diabetic person the level may be significantly higher (e.g., greater than 8%). It is generally sought to reduce the level of HbA1c in a diabetic patient's blood to between 6% and 7%. The HbA1c level reflects the idiosyncratic (i.e., patient-specific) effectiveness of blood glucose treatment over a period of several months preceding the HbA1c measurement. The HbA1c level is commonly measured by laboratory tests in order to provide information related to the long-term effectiveness of diabetes treatment.

In another aspect of the claimed methods and kits, blood glucose concentrations may be measured by a continuous glucose monitor that determines blood glucose levels on a continuous basis (every few minutes). A typical system comprises a disposable glucose sensor placed under the skin, a link from the sensor to a non-implanted transmitter which communicates to a radio receiver, and an electronic receiver worn like a pager that displays blood glucose levels in a continuous manner, as well as monitors rising and falling trends. In an additional aspect, blood glucose levels may be monitored by non-invasive technique not requiring access to blood. Such techniques include infra-red detection, ultra-sound measurements, or dielectric spectroscopy. While HbA1c levels provide valuable information, HbA1c levels are measured infrequently for typical patients and give little direct information as to the variability associated with a patient's glycemic control or the propensity for hypoglycemia or hyperglycemia. For example, a patient may have an acceptable HbA1c level ranging between 4% and 7%, but may have frequent hypoglycemic and/or hyperglycemic episodes because such episodes are not reflected in an HbA1c level.

In one aspect of any of these methods and kits, the baseline period of evaluation extends from about one hour to any period of time prior to starting C-peptide therapy. In another aspect of any of these methods and kits, the baseline period may include historical logs of glucose, insulin, nerve conduction velocity, C-peptide levels, or HbA1c data collected over any period of time prior to starting C-peptide therapy. In one embodiment, the baseline period extends from about one day prior to starting C-peptide therapy to about 24 weeks prior to starting therapy. In another aspect, the baseline period extends from about one day to about 12 weeks. In another aspect, the baseline period extends from about one day to about 6 weeks. In another aspect, the baseline period extends from about one day to about 4 weeks. In another aspect, the baseline period extends from about one day to about 2 weeks. In another aspect, the baseline period extends from about one day to about one week.

In one aspect, the present invention is based on the discovery that patients who exhibit a reduced basal or meal-stimulated C-peptide level may respond more effectively to C-peptide therapy, and are therefore at increased risk of developing hypoglycemia. Accordingly in one aspect of the invention, C-peptide levels are monitored prior to initiating C-peptide therapy to assess the relative risk of the patient developing hypoglycemia. In one embodiment of any of the claimed methods and kits, the patient's C-peptide levels are measured and the patients are grouped according to their basal C-peptide level prior to starting C-peptide therapy. In one aspect, patients are grouped into group I (about 0.05 nM or less C-peptide); group II (about 0.05 to about 0.1 nM C-peptide); group III (about 0.1 to about 0.2 nM C-peptide), group IV (about 0.2 to about 0.3 nM C-peptide); group V (about 0.3 to about 0.4 nM C-peptide); group VI (about 0.4 to about 0.5 nM C-peptide). In one aspect of the invention, patients with altered C-peptide levels display an altered risk of developing hypoglycemia. In one aspect of the invention, an altered risk of developing hypoglycemia when initiating C-peptide therapy is found in patients in groups I to III compared to groups IV to VI. Accordingly in one aspect of any of the methods and kits described herein, the invention includes a method for assessing a patient's risk for developing hypoglycemia by measuring the patient's basal or meal-stimulated C-peptide levels prior to initiating C-peptide therapy, and reducing the insulin dosage of the patient at risk of hypoglycemia when the patient starts C-peptide therapy.

In another aspect of any of these methods and kits, the clinical parameter is selected from energy expenditure, weight gain, caloric intake, body mass index, and nerve conduction velocity, amplitude of the nerve signal, or vibration perception threshold. In one aspect, the clinical parameter is sensory nerve conduction velocity. In one aspect, the clinical parameter is motor nerve conduction velocity. In one aspect, sensory nerve conduction is measured using the sural, ulnar, or median nerves. In one aspect, motor nerve conduction is measured using the median, ulnar, or peroneal nerves.

In one aspect, energy expenditure may be estimated based on reference ranges of energy expenditure for various activities, including work-related activity, exercise regimen, and other daily activities and functions, and as refined by the patient's weight, gender, and age. Such data may be collected, or monitored directly by the patient. In another aspect of any of these methods and kits, the patient's weight gain when starting C-peptide therapy is used as a proxy of appropriate insulin usage when combined with C-peptide therapy, and is therefore used to assess the relative long-term risk of the patient developing hypoglycemia.

In a clinical setting, insulin administration is frequently associated with body weight gain secondary to increased caloric intake to prevent the development of hypoglycemia combined with the anabolic effects of insulin, resulting in increased lipogenesis in adipose tissue and skeletal muscle. In type 2 diabetes patients starting on insulin therapy, the weight gain may amount to 2-4 kg over a period of 4-8 months (Goudswaard et al., Cochrane Data Base Syst Rev, 4: CD 003418 (2004); Carver C, *Diabetes Educ.*, 32:910-917, (2006)). Indeed it is well-established that insulin exerts potent effects on lipid metabolism. It stimulates catabolism of lipoproteins and triglycerides via activation of lipoprotein lipase in the vascular capillaries and enhances esterification of free fatty acids, resulting in storage of lipids in adipose tissue, skeletal muscle, and liver. Moreover, epidemiological data and experimental evidence indicate that hyperinsulinemia may be linked to the development of atherosclerotic vascular disease. Thus increased weight gain is indicative of increased caloric intake and/or increased insulin usage that can signify that the patient is at increased risk of developing hypoglycemia, or of developing a hypoglycemic coma when starting, or during, C-peptide therapy.

Accordingly in one aspect of any of the claimed methods and kits, the patient's body mass index (BMI), or a change in BMI upon starting, or during, C-peptide therapy, may be monitored. BMI is measured (kg/m$^2$ [or lb/in$^2$×704.5]). Alternatively, changes in any of the following parameters (alone or in any combination) may be used to estimate a change in BMI; weight, waist circumference (estimates fat distribution), waist-to-hip ratio (estimates fat distribution), skin fold thickness (if measured at several sites, estimates fat distribution), or bio-impedance (based on principle that lean mass conducts current better than fat mass [i.e., fat mass impedes current], estimates % fat). The parameters for normal, overweight, or obese individuals are as follows: Underweight: BMI less than 18.5; Normal: BMI 18.5 to 24.9; Overweight: BMI=25 to 29.9. Obese individuals are characterized as having a BMI of 30 to 34.9, being greater than 20% above "normal" weight for height. Individuals with severe or morbid obesity are characterized as having a BMI of greater than 35.

In one aspect of any of these methods and kits, caloric intake over the baseline, or evaluation periods of C-peptide therapy may be monitored. In one aspect of these methods and kits, caloric intake may be further differentiated based on the type of food ingested; e.g., based on the relative consumption of carbohydrates, proteins, and fat. Such estimates may be based on any art-recognized methods for determining such parameters.

In another embodiment of any of the claimed methods and kits, the parameters monitored over the baseline are compared to one or more biomarkers, analytes, or clinical parameters monitored after the patient has initiated C-peptide therapy. In one aspect of any of these methods and kits, the same biomarker, analyte, or clinical parameter is compared before and after therapy. In another aspect, distinct biomarker, analyte, or clinical parameters are used before and after starting C-peptide therapy to assess the risk of the patient developing hypoglycemia, or potential for the patient gaining weight.

In one aspect of any of these methods and kits, one or more biomarkers, analytes, or clinical parameters are monitored during a lead-in evaluation period of C-peptide therapy. In one aspect of any of these methods and kits, the evaluation period of C-peptide therapy extends from about one hour, to any period of time after starting C-peptide therapy. In another aspect of any of these methods and kits, the evaluation period may include historical logs of glucose, insulin, C-peptide, nerve conduction velocity, or HbA1c data collected over any period of time after starting C-peptide therapy. In one embodiment, the evaluation period extends from about one day after starting C-peptide therapy to about 24 weeks after starting therapy. In another aspect, the evaluation period extends from about one day to about 12 weeks. In another aspect, the evaluation period extends from about one day to about 6 weeks. In another aspect, the evaluation period extends from about one day to about 4 weeks. In another aspect, the evaluation period extends from about one day to about 2 weeks. In another aspect, the evaluation period extends from about one day to about one week.

In another aspect of any of these methods and kits, data from a biomarker, analyte, or clinical parameter may be compared to an index reference value that represents the expected normal value, or range, for that patient variable. For example, such index reference values may be based on historical data sets matched for the patient's age, gender, race, medical history, pre-existing medical conditions, length of diabetes duration, etc. In any of these methods and kits, data from the patient may be obtained prior, during, or when starting C-peptide therapy, and compared to an index reference value or range, e.g., by variance of greater than about 2 standard deviations from the mean.

Accordingly, in another aspect of any of the claimed methods and kits, risk prediction for the development of hypoglycemia can also encompass risk prediction algorithms and computed indices that assess and estimate a patient's absolute risk for developing hypoglycemia with reference to a historical cohort. Risk assessment using such predictive mathematical algorithms and computed indices has increasingly been incorporated into guidelines for diagnostic testing and treatment, and encompass indices obtained from and validated with, inter alia, multistage, stratified samples from a representative population.

Tests to measure biomarkers, analytes, and clinical parameters can be implemented on a wide variety of diagnostic test systems, including remote monitoring systems that can be connected via wireless communication systems and web-based patient monitoring and tracking systems. Such sensors typically provide continuous monitoring of a particular physiological function and an alarm output if a critical event arises. The alarm output can be transmitted utilizing conventional communication technology such as a wired hospital network, radio frequency, Bluetooth or magnetic coupling (B-field), or via a cell phone. Representative monitoring systems include, e.g., those described in US Patent Applications Nos. 20090231125, 20090182204, and 20090171169.

Insulin Types and Administration Forms

There are over 180 individual insulin preparations available worldwide which have been developed to provide different lengths of activity (activity profiles). Approximately 25% of these are soluble insulin (unmodified form); about 35% are long- or intermediate-acting basal insulins (mixed with NPH [neutral protamine Hagedorn] insulin or Lente insulin [insulin zinc suspension], or forms that are modified to have an increased isoelectric point [insulin glargine], or acylation [insulin detemir]; these forms have reduced solubility, slow subcutaneous absorption, and long duration of action relative to soluble insulins); about 2% are rapid-acting insulins (e.g., which are engineered by amino acid change, and have reduced self-association and increased subcutaneous absorption); and about 38% are pre-mixed insulins (e.g., mixtures of short-, intermediate-, and long-acting insulins; these preparations have the benefit of a reduced number of daily injections).

Short-acting insulin preparations that are commercially available in the US include regular insulin and rapid-acting insulins. Regular insulin has an onset of action of 30-60 minutes, peak time of effect of 1.5 to 2 hours, and duration of activity of 5 to 12 hours. Rapid-acting insulins, such as Aspart (Novo Rapid), Lispro (Humalog), and Glulisine (Apidra), have an onset of action of 10-30 minutes, peak time of effect of around 30 minutes, and a duration of activity of 3 to 5 hours.

Intermediate-acting insulins, such as NPH and Lente insulins, have an onset of action of 1 to 2 hours, peak time of effect of 4 to 8 hours, and a duration of activity of 10 to 20 hours.

Long-acting insulins, such as Ultralente insulin, have an onset of action of 2 to 4 hours, peak time of effect of 8 to 20 hours, and a duration of activity of 16 to 24 hours. Other examples of long-acting insulins include Glargine and Detemir. Glargine insulin has an onset of action of 1 to 2 hours, and a duration of action of 24 hours, but with no peak effect.

In many cases, regimens that use insulin in the management of diabetes combine long-acting and short-acting insulin. For example, Lantus, from Aventis Pharmaceuticals Inc., is a recombinant human insulin analog that is a long-acting, parenteral blood-glucose-lowering agent whose longer duration of action (up to 24 hours) is directly related to its slower rate of absorption. Lantus is administered subcutaneously once a day, preferably at bedtime, and is said to provide a continuous level of insulin, similar to the slow, steady (basal) secretion of insulin provided by the normal pancreas. The activity of such a long-acting insulin results in a relatively constant concentration/time profile over 24 hours with no pronounced peak, thus allowing it to be administered once a day as a patient's basal insulin. Such long-acting insulin has a long-acting effect by virtue of its chemical composition, rather than by virtue of an addition to insulin when administered.

More recently automated wireless controlled systems for continuous infusion of insulin, such as the system sold under the trademark OMNIPOD™ Insulin Management System (Insulet Corporation, Bedford, Mass.) have been developed. These systems provide continuous subcutaneous insulin delivery with blood glucose monitoring technology in a discreet two-part system. This system eliminates the need for daily insulin injections, and does not require a conventional insulin pump which is connected via tubing.

OMNIPOD™ is a small lightweight device that is worn on the skin like an infusion set. It delivers insulin according to pre-programmed instructions transmitted wirelessly from the Personal Diabetes Manager (PDM). The PDM is a wireless, hand-held device that is used to program the OMNIPOD™ Insulin Management System with customized insulin delivery instructions, monitor the operation of the system, and check blood glucose levels using blood glucose test strips sold under the trademark FREESTYLE™. There is no tubing connecting the device to the PDM. OMNIPOD™ Insulin Management System is worn beneath the clothing, and the PDM can be carried separately in a backpack, briefcase, or purse. Similar to currently available insulin pumps, the OMNIPOD™ Insulin Management System features fully programmable continuous subcutaneous insulin delivery with multiple basal rates and bolus options, suggested bolus calculations, safety checks, and alarm features.

The aim of insulin treatment of diabetics is typically to administer enough insulin such that the patient will have blood glucose levels within the physiological range and normal carbohydrate metabolism throughout the day. Because the pancreas of a diabetic individual does not secrete sufficient insulin throughout the day, in order to effectively control diabetes through insulin therapy, a long-lasting insulin treatment, known as basal insulin, must be administered to provide the slow and steady release of insulin that is needed to control blood glucose concentrations and to keep cells supplied with energy when no food is being digested. Basal insulin is necessary to suppress glucose production between meals and overnight and preferably mimics the patient's normal pancreatic basal insulin secretion over a 24-hour period. Thus, a diabetic patient may administer a single dose of a long-acting insulin each day subcutaneously, with an action lasting about 24 hours.

Furthermore, in order to effectively control diabetes through insulin therapy by dealing with postprandial rises in glucose levels, a bolus, fast-acting treatment must also be administered. The bolus insulin, which is generally administered subcutaneously, provides a rise in plasma insulin levels at approximately 1 hour after administration, thereby limiting hyperglycemia after meals. Thus, these additional quantities of regular insulin, with a duration of action of, e.g., 5 to 6 hours, may be subcutaneously administered at those times of the day when the patient's blood glucose level tends to rise too high, such as at meal times. As an alternative to administering basal insulin in combination with bolus insulin, repeated and regular lower doses of bolus insulin may be administered in place of the long-acting basal insulin, and bolus insulin may be administered postprandially as needed.

Currently, regular subcutaneously injected insulin is recommended to be dosed at 30 to 45 minutes prior to mealtime. As a result, diabetic patients and other insulin users must engage in considerable planning of their meals and of their insulin administrations relative to their meals. Unfortunately, intervening events that may take place between administration of insulin and ingestion of the meal may affect the anticipated glucose excursions.

Furthermore, there is also the potential for hypoglycemia if the administered insulin provides a therapeutic effect over too great a time, e.g., after the rise in glucose levels that occur as a result of ingestion of the meal has already been lowered. As outlined in the Examples, this risk of hypoglycemia is increased in patients who have been treated with C-peptide due to a reduced requirement for insulin.

Accordingly, in one aspect of any of the methods and kits disclosed herein, the present invention includes a method for reducing the risk of the patient developing hypoglycemia by reducing the average daily dose of insulin administered to the patient by about 5% to about 50% after starting C-peptide therapy. In another aspect, the dose of insulin administered is reduced by about 5% to about 45% compared to the patient's insulin dose prior to starting C-peptide treatment. In another aspect, the dose of insulin administered is reduced by about 5% to about 40% compared to the patient's insulin dose prior to starting C-peptide treatment. In another aspect, the dose of insulin administered is reduced by about 5% to about 35% compared to the patient's insulin dose prior to starting C-peptide treatment. In another aspect, the dose of insulin administered is reduced by about 5% to about 30% compared to the patient's insulin dose prior to starting C-peptide treatment. In another aspect, the dose of insulin administered is reduced by about 5% to about 25% compared to the patient's insulin dose prior to starting C-peptide treatment. In another aspect, the dose of insulin administered is reduced by about 5% to about 20% compared to the patient's insulin dose prior to starting C-peptide treatment. In another aspect, the dose of insulin administered is reduced by about 5% to about 15% compared to the patient's insulin dose prior to starting C-peptide treatment. In another aspect, the dose of insulin administered is reduced by about 5% to about 10% compared to the patient's insulin dose prior to starting C-peptide treatment.

In another aspect, the dose of insulin administered is reduced by about 2% to about 10% compared to the patient's insulin dose prior to starting C-peptide treatment. In another aspect, the dose of insulin administered is reduced by about 2% to about 15% compared to the patient's insulin dose prior to starting C-peptide treatment.

In another aspect, the dose of insulin administered is reduced by about 2% to about 20% compared to the patient's insulin dose prior to starting C-peptide treatment.

In another aspect, the dose of insulin administered is reduced by about 10% to about 50% compared to the patient's insulin dose prior to starting C-peptide treatment. In another aspect, the dose of insulin administered is reduced by about 10% to about 45% compared to the patient's insulin dose prior to starting C-peptide treatment. In another aspect, the dose of insulin administered is reduced by about 10% to about 40% compared to the patient's insulin dose prior to starting C-peptide treatment. In another aspect, the dose of insulin administered is reduced by about 10% to about 35% compared to the patient's insulin dose prior to starting C-peptide treatment. In another aspect, the dose of insulin administered is reduced by about 10% to about 30% compared to the patient's insulin dose prior to starting C-peptide treatment. In another aspect, the dose of insulin administered is reduced by about 10% to about 25% compared to the patient's insulin dose prior to starting C-peptide treatment. In another aspect, the dose of insulin administered is reduced by about 10% to about 20% compared to the patient's insulin dose prior to starting C-peptide treatment. In another aspect, the dose of insulin administered is reduced by at least 10% compared to the patient's insulin dose prior to starting C-peptide treatment.

In one aspect of any of these methods and kits, the dose of short-acting insulin administered is selectively reduced by any of the prescribed ranges listed above. In another aspect of any of these methods and kits, the dose of intermediate-acting insulin administered is selectively reduced by any of the prescribed ranges. In one aspect of any of these methods and kits, the dose of long-acting insulin administered is selectively reduced by any of the prescribed ranges listed above.

In another aspect of any of these methods and kits, the dose of intermediate- and long-acting insulin administered is independently reduced by any of the prescribed ranges listed above, while the dose of short-acting insulin remains substantially unchanged.

In one aspect of these methods and kits, the dose of short-acting insulin administered is reduced by about 5% to about 50% compared to the patient's insulin dose prior to starting C-peptide treatment. In another embodiment, the dose of short-acting insulin administered is reduced by about 5% to about 35% compared to the patient's insulin dose prior to starting C-peptide treatment. In another embodiment, the dose of short-acting insulin administered is reduced by about 10% to about 20% compared to the patient's insulin dose prior to starting C-peptide treatment. In one aspect of these methods and kits, the dose of short-acting insulin administered preprandially for a meal is reduced. In another aspect of these methods and kits, the dose of short-acting insulin administered in the morning or at nighttime is reduced. In another aspect of any of these methods and kits, the dose of short-acting insulin administered is reduced while the dose of long-acting and/or intermediate-acting insulin administered to the patient is substantially unchanged.

In another aspect of any of the methods and kits disclosed herein, the present invention includes a method for reducing the risk of the patient developing hypoglycemia by reducing the average daily dose of intermediate-acting insulin administered to the patient by about 5% to about 35% after starting C-peptide therapy. In one aspect of these methods and kits, the dose of intermediate-acting insulin administered is reduced by about 5% to about 50% compared to the patient's insulin dose prior to starting C-peptide treatment. In another embodiment, the dose of intermediate-acting insulin administration is reduced by about 5% to about 35% compared to the patient's insulin dose prior to starting C-peptide treatment. In another embodiment, the dose of intermediate-acting insulin administered is reduced by about 10% to about 20% compared to the patient's insulin dose prior to starting C-peptide treatment. In another aspect of these methods and kits, the dose of intermediate-acting insulin administered in the morning or at nighttime is reduced. In another aspect of any of these methods and kits, the dose of intermediate-acting insulin administered is reduced while the dose of short-acting insulin administered to the patient is substantially unchanged.

In another aspect of any of the methods and kits disclosed herein, the present invention includes a method for reducing the risk of the patient developing hypoglycemia by reducing the average daily dose of long-acting insulin administered to the patient by about 5% to about 50% after starting C-peptide therapy. In one embodiment, the dose of long-acting insulin administered is reduced by about 5% to about 35% compared to the patient's insulin dose prior to starting C-peptide treatment. In another embodiment, the dose of long-acting insulin administered is reduced by about 10% to about 20% compared to the patient's insulin dose prior to starting C-peptide treatment. In another aspect of these methods and kits, the dose of long-acting insulin administered in the morning or at nighttime is reduced. In another aspect of any of these methods and kits, the dose of long-acting insulin administered is reduced while the dose of short-acting insulin administered to the patient is substantially unchanged.

In certain preferred embodiments, the patient achieves improved insulin utilization and insulin sensitivity while experiencing a reduced risk of developing hypoglycemia after treatment with C-peptide as compared with baseline levels prior to treatment. Preferably, the improved insulin utilization and insulin sensitivity are measured by a statistically significant decline in HOMA (Homeostasis Model Assessment) (Turner et al.: Metabolism 28(11): 1086-1096, (1979)).

Therapeutic forms of C-peptide

The terms "C-peptide" or "proinsulin C-peptide" as used herein includes all naturally-occurring and synthetic forms of C-peptide that retain C-peptide activity. Such C-peptides include the human peptide, as well as peptides derived from other animal species and genera, preferably mammals. Preferably, "C-peptide" refers to human C-peptide having the amino acid sequence EAEDLQVGQVELGGGPGAGSLQPLALEGSLQ (Seq ID No. 1 in Table D1).

C-peptides from a number of different species have been sequenced, and are known in the art to be at least partially functionally interchangeable. It would thus be a routine matter to select a variant being a C-peptide from a species or genus other than human. Several such variants of C-peptide (i.e., representative C-peptides from other species) are shown in Table D1 (see Seq ID Nos. 1-29).

TABLE D1

| C-Peptide Variants | | | |
|---|---|---|---|
| human M-proinsulin | Human (Seq ID No. 1) | EAEDLQVGQVELGGGPGAGSLQPLALEGSLQ | gb\|AAA7 2531.1\| dbj\|BAH5 9081.1\| |
| Pan troglodytes | (Seq ID No. 1) Alignment (Seq ID No. 2) | EAEDLQVGQVELGGGPGAGSLQPLALEGSLQ EAEDLQVGQVELGGGPGAGSLQPLALEGSLQ EAEDLQVGQVELGGGPGAGSLQPLALEGSLQ | NP_00100 8996.1\| emb\|CAA |

TABLE D1-continued

C-Peptide Variants

| | | | |
|---|---|---|---|
| | Identities = 31/31 (100%), Positives = 31/31 (100%), Gaps = 0/31 (0%) | | 43403.1\| GENE ID: 449570 INS |
| *Gorilla gorilla* | (Seq ID No. 1) Alignment (Seq ID No. 3) Identities = 31/31 (100%), Positives = 31/31 (100%), Gaps = 0/31 (0%) | EAEDLQVGQVELGGGPGAGSLQPLALEGSLQ EAEDLQVGQVELGGGPGAGSLQPLALEGSLQ EAEDLQVGQVELGGGPGAGSLQPLALEGSLQ | gb\|AAN0 6935.1\| |
| *Pongo pygmaeus* (Bornean orangutan) | (Seq ID No. 1) (Seq ID No. 4) Identities = 31/31 (100%), Positives = 31/31 (100%), Gaps = 0/31 (0%) | EAEDLQVGQVELGGGPGAGSLQPLALEGSLQ EAEDLQVGQVELGGGPGAGSLQPLALEGSLQ EAEDLQVGQVELGGGPGAGSLQPLALEGSLQ | gb\|AAN0 6937.1\| |
| *Chlorocebus aethiops* (Monkey) | (Seq ID No. 1) (Seq ID No. 5) Identities = 30/31 (96%), Positives = 30/31 (96%), Gaps = 0/31 (0%) | EAEDLQVGQVELGGGPGAGSLQPLALEGSLQ EAED QVGQVELGGGPGAGSLQPLALEGSLQ EAEDPQVGQVELGGGPGAGSLQPLALEGSLQ | emb\|CAA 43405.1\| |
| *Canis lupus familiaris* (Dog) | (Seq ID No. 1) (Seq ID No. 6) Identities = 23/31 (74%), Positives = 24/31 (77%), Gaps = 0/31 (0%) | EAEDLQVGQVELGGGPGAGSLQPLALEGSLQ E EDLQV VEL G PG G LQPLALEG+LQ EVEDLQVRDVELAGAPGEGGLQPLALEGALQ | ref\|NP_00 1123565.1 \|sp\|P01321 .1\|INS_C ANFAem b\|CAA234 75.1\| GENE ID: 483665 INS |
| *Oryctolagus cuniculus* (Rabbit) | (Seq ID No. 1) (Seq ID No. 7) Identities = 23/31 (74%), Positives = 25/31 (80%), Gaps = 0/31 (0%) | EAEDLQVGQVELGGGPGAGSLQPLALEGSLQ E E+LQVGQ ELGGGP AG LQP ALE +LQ EVEELQVGQAELGGGPDAGGLQPSALELALQ | gb\|ACK44 319.1\| |
| *Rattus norvegicus* | (Seq ID No. 1) (Seq ID No. 8) Identities = 22/31 (70%), Positives = 24/31 (77%), Gaps = 0/31 (0%) | EAEDLQVGQVELGGGPGAGSLQPLALEGSLQ E ED QV Q+ELGGGPGAG LQ LALE + Q EVEDPQVAQLELGGGPGAGDLQTLALEVARQ | ref\|NP_06 2003.1\| sp\|P01323 .1\|INS2_R AT emb\|CAA 24560.1\| GENE ID: 24506 Ins2 |
| *Apodemus semotus* (Taiwan field mouse) | (Seq ID No. 1) (Seq ID No. 9) Identities = 22/31 (70%), Positives = 24/31 (77%), Gaps = 0/31 (0%) | EAEDLQVGQVELGGGPGAGSLQPLALEGSLQ E ED QV Q+ELGGGPGAG LQ LALE + Q EVEDPQVAQLELGGGPGAGDLQTLALEVARQ | gb\|ABB89 748.1\| |
| *Geodia cydonium* sponge | (Seq ID No. 1) (Seq ID No. 10) Identities = 23/31 (74%), Positives = 24/31 (77%), Gaps = 0/31 (0%) | EAEDLQVGQVELGGGPGAGSLQPLALEGSLQ E ED QVGQVELG GPGAGS Q LALE + Q EVEDPQVGQVELGAGPGAGSEQTLALEVARQ | pir\|\|S0927 8 |
| *Mus musculus* | (Seq ID No. 1) (Seq ID No. 11) Identities = 21/27 (77%), Positives = 22/27 (81%), Gaps = 0/27 (0%) | EAEDLQVGQVELGGGPGAGSLQPLALE E ED QV Q+ELGGGPGAG LQ LALE EVEDPQVAQLELGGGPGAGDLQTLALE | ref\|NP_03 2413.1\| sp\|P01326 .1\|INS2_ MOUSEe mb\|CAA2 8433.1\| GENE ID: 16334 Ins2 |
| *Mus caroli* (Ryukyu mouse) | (Seq ID No. 1) (Seq ID No. 12) Identities = 21/27 (77%), Positives = 22/27 (81%), Gaps = 0/27 (0%) | EAEDLQVGQVELGGGPGAGSLQPLALE E ED QV Q+ELGGGPGAG LQ LALE EVEDPQVAQLELGGGPGAGDLQTLALE | gb\|ABB89 749.1\| |
| *Rattus norvegicus* | (Seq ID No. 1) (Seq ID No. 13) Identities = 22/31 (70%), Positives = 24/31 (77%), Gaps = 0/31 (0%) | EAEDLQVGQVELGGGPGAGSLQPLALEGSLQ E ED QV Q+ELGGGPGAG LQ LALE + Q EVEDPQVPQLELGGGPGAGDLQTLALEVARQ | prf\|\|72046 0B |
| *Rattus losea* | (Seq ID No. 1) (Seq ID No. 14) | EAEDLQVGQVELGGGPGAGSLQPLALEGSLQ E ED QV Q ELGGGPGAG LQ LALE + Q EVEDPQVAQQELGGGPGAGDLQTLALEVARQ | gb\|ABB89 747.1\| |

TABLE D1-continued

C-Peptide Variants

| | | | |
|---|---|---|---|
| | | Identities = 22/31 (70%), Positives = 23/31 (74%), Gaps = 0/31 (0%) | |
| *Niviventer coxingi* (Coxing's white-bellied rat) | (Seq ID No. 1) | EAEDLQVGQVELGGGPGAGSLQPLALEGSLQ<br>E ED QV Q+ELGGGPG G LQ LALE + Q | gb\|ABB89750.1\| |
| | (Seq ID No. 15) | EVEDPQVPQLELGGGPGTGDLQTLALEVARQ<br>Identities = 21/31 (67%), Positives = 23/31 (74%), Gaps = 0/31 (0%) | |
| *Microtus kikuchii* (Taiwan vole) | (Seq ID No. 1) | AEDLQVGQVELGGGPGAGSLQPLALE<br>ED QV Q+ELGGGPGAG LQ LALE | gb\|ABB89752.1\| |
| | (Seq ID No. 16) | VEDPQVAQLELGGGPGAGDLQTLALE<br>Identities = 20/26 (76%), Positives = 21/26 (80%), Gaps = 0/26 (0%) | |
| *Rattus norvegicus* insulin 1 precursor | (Seq ID No. 1) | EAEDLQVGQVELGGGPGAGSLQPLALEGSLQ<br>E ED QV Q+ELGGGP AG LQ LALE + Q | ref\|NP_062002.1\| |
| | (Seq ID No. 17) | EVEDPQVPQLELGGGPEAGDLQTLALEVARQ<br>Identities = 21/31 (67%), Positives = 23/31 (74%), Gaps = 0/31 (0%) | gb\|AAA41439.1\|<br>gb\|AAA41442.1\|<br>emb\|CAA24559.1\|<br>gb\|EDL94407.1\|<br>GENE ID: 24505 Ins1 |
| *Felis catus* (Domestic cat) | (Seq ID No. 1) | EAEDLQVGQVELGGGPGAGSLQPLALEGSLQ<br>EAEDLQ ELG PGAG LQP ALE LQ | ref\|NP_001009272.1\| |
| | (Seq ID No. 18) | EAEDLQGKDAELGEAPGAGGLQPSALEAPLQ<br>Identities = 21/31 (67%), Positives = 21/31 (67%), Gaps = 0/31 (0%) | sp\|P06306.2\|INS_FELCA<br>dbj\|BAB84110.1\|<br>GENE ID: 493804 INS |
| Golden hamster | (Seq ID No. 1) | AEDLQVGQVELGGGPGAGSLQPLALE<br>ED QV Q+ELGGGPGA LQ LALE | sp\|P01313.2\|INS_CRILO |
| | (Seq ID No. 19) | VEDPQVAQLELGGGPGADDLQTLALE<br>Identities = 19/26 (73%), Positives = 20/26 (76%), Gaps = 0/26 (0%) | pir\|\|I48166<br>gb\|AAA37089.1\| |
| *Niviventer coxingi* (Coxing's white-bellied rat) | (Seq ID No. 1) | EAEDLQVGQVELGGGPGAGSLQPLALEGSLQ<br>E ED QV Q+ELG GP AG LQ LALE + Q | gb\|ABB89746.1\| |
| | (Seq ID No. 20) | EVEDPQVAQLELGEGPEAGDLQTLALEVARQ<br>Identities = 20/31 (64%), Positives = 22/31 (70%), Gaps = 0/31 (0%) | |
| *Apodemus semotus* (Taiwan field mouse) | (Seq ID No. 1) | EAEDLQVGQVELGGGPGAGSLQPLALEGSLQ<br>E ED QV Q+ELGG PG G L+ LALE + Q | gb\|ABB89744.1\| |
| | (Seq ID No. 21) | EVEDPQVEQLELGGAPGTGDLETLALEVARQ<br>Identities = 19/31 (61%), Positives = 22/31 (70%), Gaps = 0/31 (0%) | |
| *Rattus losea* | (Seq ID No. 1) | EAEDLQVGQVELGGGPGAGSLQPLALEGSLQ<br>E ED QV Q+ELGG P AG LQ LALE + Q | gb\|ABB89743.1\| |
| | (Seq ID No. 22) | EVEDPQVPQLELGGSPEAGDLQTLALEVARQ<br>Identities = 20/31 (64%), Positives = 22/31 (70%), Gaps = 0/31 (0%) | |
| *Meriones unguiculatus* (Mongolian gerbil) | (Seq ID No. 1) | AEDLQVGQVELGGGPGAGSLQPLALEGSLQ<br>ED Q+ Q+ELGG PGAG LQ LALE + Q | gb\|ABB89751.1\| |
| | (Seq ID No. 23) | VEDPQMPQLELGGSPGAGDLQALALEVARQ<br>Identities = 19/30 (63%), Positives = 22/30 (73%), Gaps = 0/30 (0%) | |
| *Psammomys obesus* (Fat sand rat) | (Seq ID No. 1) | AEDLQVGQVELGGGPGAGSLQPLALEGSLQ<br>+D Q+ Q+ELGG PGAG L+ LALE + Q | sp\|Q62587.1\|INS_PSAOB |
| | (Seq ID No. 24) | VDDPQMPQLELGGSPGAGDLRALALEVARQ<br>Identities = 17/30 (56%), Positives = 22/30 (73%), Gaps = 0/30 (0%) | emb\|CAA66897.1\| |
| *Sus scrofa* (Pig) | (Seq ID No. 1) | EAEDLQVGQVELGGGPGAGSLQPLALEG<br>EAE+ Q G VELGG G GL LQ LALEG | ref\|NP_001103242.1\| |
| | (Seq ID No. 25) | EAENPQAGAVELGG--GLGGLQALALEG<br>Identities = 19/28 (67%), Positives = 20/28 (71%), Gaps = 2/28 (7%) | |
| *Rhinolophus ferrumequinum* | (Seq ID No. 26) | EVEDPQAGQVELGGGPGTGGLQSLALEGPPQ | gb\|ACC68945.1\| |

TABLE D1-continued

C-Peptide Variants

| | | | |
|---|---|---|---|
| *Equus przewalskii* (Horse) | (Seq ID No. 27) | EAEDPQVGEVELGGGPGLGGLQPLALAGPQQ | GENE ID: 100060077 LOC100060077 gb\|AAB25818.1\| |
| *Bos Taurus* (Bovine) | (Seq ID No. 28) | EVEGPQVGALELAGGPGAGGLEGPPQ | gb\|AAI42035.1\| |
| *Otolemur garnettii* (Small-eared galago) | (Seq ID No. 29) | DTEDPQVGQVGLGGSPITGDLQSLALDVPPQ | gb\|ACH53103.1\| |

Thus all such homologues, orthologs, and naturally-occurring isoforms of C-peptide from human as well as other species (Seq ID Nos. 1-29) are included in any of the methods and kits of the invention, as long as they retain detectable C-peptide activity.

The C-peptides may be in their native form, i.e., as different variants as they appear in nature in different species which may be viewed as functionally equivalent variants of human C-peptide, or they may be functionally equivalent natural derivatives thereof, which may differ in their amino acid sequence, e.g., by truncation (e.g., from the N- or C-terminus or both) or other amino acid deletions, additions, insertions, substitutions, or post-translational modifications. Naturally-occurring chemical derivatives, including post-translational modifications and degradation products of C-peptide, are also specifically included in any of the methods and kits of the invention including, e.g., pyroglutamyl, iso-aspartyl, proteolytic, phosphorylated, glycosylated, oxidatized, isomerized, and deaminated variants of C-peptide.

It is known in the art to synthetically modify the sequences of proteins or peptides, while retaining their useful activity, and this may be achieved using techniques which are standard in the art and widely described in the literature, e.g., random or site-directed mutagenesis, cleavage, and ligation of nucleic acids, or via the chemical synthesis or modification of amino acids or polypeptide chains. Similarly it is within the skill in the art to address and/or mitigate immunogenicity concerns if they arise using C-peptide variants, e.g., by the use of automated computer recognition programs to identify potential T cell epitopes, and directed evolution approaches to identify less immunogenic forms.

Any such modifications, or combinations thereof, may be made and used in any of the methods and kits of the invention, as long as activity is retained. The C-terminal end of the molecule is known to be important for activity. Preferably, therefore, the C-terminal end of the C-peptide should be preserved in any such C-peptide variants or derivatives, more preferably the C-terminal pentapeptide of C-peptide (EGSLQ) (Seq ID No. 31) should be preserved or sufficient (see Henriksson M et al.: *Cell Mol. Life. Sci.* 62: 1772-1778, (2005)). As mentioned above, modification of an amino acid sequence may be by amino acid substitution, e.g., an amino acid may be replaced by another that preserves the physico-chemical character of the peptide (e.g., A may be replaced by G or vice versa, V by A or L; E by D or vice versa; and Q by N). Generally, the substituting amino acid has similar properties, e.g., hydrophobicity, hydrophilicity, electronegativity, bulky side chains, etc., to the amino acid being replaced.

Modifications to the mid-part of the C-peptide sequence (e.g., to residues 13 to 25 of human C-peptide) allow the production of functional derivatives or variants of C-peptide. Thus, C-peptides which may be used in any of the methods or kits of the invention may have amino acid sequences which are substantially homologous, or substantially similar to the native C-peptide amino acid sequences, e.g., to the human C-peptide sequence of Seq ID No. 1 or any of the other native C-peptide sequences shown in Table D1. Alternatively, the C-peptide may have an amino acid sequence having at least 30% preferably at least 40, 50, 60, 70, 75, 80, 85, 90, 95, 98, or 99% identity with the amino acid sequence of any one of Seq ID Nos. 1-29 as shown in Table D1, preferably with the native human sequence of Seq ID No. 1. In a preferred embodiment, the C-peptide for use in any of the methods or kits of the present invention is at least 80% identical to a sequence selected from Table D1. In another aspect, the C-peptide for use in any of the methods or kits of the invention is at least 80% identical to human C-peptide (Seq ID No. 1). Although any amino acid of C-peptide may be altered as described above, it is preferred that one or more of the glutamic acid residues at positions 3, 11, and 27 of human C-peptide (Seq ID No. 1) or corresponding or equivalent positions in C-peptide of other species, are conserved. Preferably, all of the glutamic acid residues at positions 3, 11, and 27 (or corresponding Glu residues) of Seq ID No. 1 are conserved. Alternatively, it is preferred that Glu27 of human C-peptide (or a corresponding Glu residue of a non-human C-peptide) is conserved. An exemplary functional equivalent form of C-peptide which may be used in any of the methods or kits of the invention includes the amino acid sequences:

EXEXXQXXXXELXXXXXXXXXXXXALBXXXQ (Seq ID No. 30).

GXEXXQXXXXELXXXXXXXXXXXXALBXXXQ (Seq ID No. 33).

As used herein, X is any amino acid. The N-terminal residue may be either Glu or Gly (Seq ID No. 30 or Seq ID No. 33 respectively). Functionally equivalent derivatives or variants of native C-peptide sequences may readily be prepared according to techniques well-known in the art, and include peptide sequences having a functional, e.g., a biological activity of a native C-peptide.

Fragments of native or synthetic C-peptide sequences may also have the desirable functional properties of the peptide from which they were derived and may be used in any of the methods or kits of the invention. The term "fragment" as used herein thus includes fragments of a C-peptide provided that the fragment retains the biological or therapeutically beneficial activity of the whole molecule. The fragment may also include a C-terminal fragment of C-peptide. Preferred fragments comprise residues 15-31 of native C-peptide, more especially residues 20-31. Peptides comprising the pentapeptide EGSLQ (Seq ID No. 31) (residues 27-31 of native human C-peptide) are also preferred. The fragment may thus vary in size from, e.g., 4 to 30 amino acids or 5 to 20 residues. Suitable fragments are disclosed in WO 98/13384 the contents of which are incorporated herein by reference.

The fragment may also include an N-terminal fragment of C-peptide, typically having the sequence EAEDLQVGQVEL (Seq ID No. 32), or a fragment thereof which comprises 2 acidic amino acid residues, capable of adopting a conformation where said two acidic amino acid residues are spatially separated by a distance of 9-14 Å between the alpha-carbons thereof. Also included are fragments having N- and/or C-terminal extensions or flanking sequences. The length of such extended peptides may vary, but typically are not more than 50, 30, 25, or 20 amino acids in length. Representative suitable fragments are described in U.S. Pat. No. 6,610,649, which is hereby incorporated by reference in its entirety.

In such a case it will be appreciated that the extension or flanking sequence will be a sequence of amino acids which is not native to a naturally-occurring or native C-peptide, and in particular a C-peptide from which the fragment is derived. Such a N- and/or C-terminal extension or flanking sequence may comprise, e.g., from 1 to 10, 1 to 6, 1 to 5, 1 to 4, or 1 to 3 amino acids.

The term "derivative" as used herein thus refers to C-peptide sequences or fragments thereof, which have modifications as compared to the native sequence. Such modifications may be one or more amino acid deletions, additions, insertions, and/or substitutions. These may be contiguous or non-contiguous. Representative variants may include those having 1 to 6, or more preferably 1 to 4, 1 to 3, or 1 or 2 amino acid substitutions, insertions, and/or deletions as compared to any of Seq ID Nos. 1-33. The substituted amino acid may be any amino acid, particularly one of the well-known 20 conventional amino acids (Ala (A); Cys (C); Asp (D); Glu (E); Phe (F); Gly (G); His (H); Ile (I); Lys (K); Leu (L); Met (M); Asn (N); Pro (P); G in (O); Arg (R); Ser (S); Thr (T); Val (V); Trp (W); and Tyr (Y)). Any such variant or derivative of C-peptide may be used in any of the methods or kits of the invention.

Fusion proteins of C-peptide to other proteins are also included, and these fusion proteins may enhance C-peptide's biological activity, targeting, biological life, or pharmacokinetic properties. Examples of fusion proteins that improve pharmacokinetic properties include without limitation, fusions to human albumin (Osborn et al.: *Eur. J. Pharmacol.* 456(1-3): 149-158, (2002)), antibody fc domains, poly Glu or poly Asp sequences, and transferrin. Additionally, fusion with conformationally disordered polypeptide sequences composed of the amino acids Pro, Ala, and Ser ('PASylation') or hydroxyethyl starch (sold under the trademark HESYLATION®) provides a simple way to increase the hydrodynamic volume of the C-peptide. This additional extension adopts a bulky random structure, which significantly increases the size of the resulting fusion protein. By this means the typically rapid clearance of the C-peptide via kidney filtration is retarded by several orders of magnitude.

An additional fusion protein approach contemplated for use within the present invention includes the fusion of C-peptide to a multimerization domain. Representative multimerization domains include without limitation coiled-coil dimerization domains such as leucine zipper domains which are found in certain DNA-binding polypeptides, the dimerization domain of an immunoglobulin Fab constant domain, such as an immunoglobulin heavy chain $CH_1$ constant region or an immunoglobulin light chain constant region. In a preferred embodiment, the multimerisation domain is derived from tetranectin, and more specifically comprises the tetranectin trimerising structural element, which is described in detail in WO 98/56906.

It will be appreciated that a flexible molecular linker (or spacer) optionally may be interposed between, and covalently join, the C-peptide and any of the fusion proteins disclosed herein. Any such fusion protein many be used in any of the methods or kits of the present invention.

Chemical modifications of the native C-peptide structure, which retain or stabilize C-peptide activity or biological half-life, may also be used with any of the methods or kits described herein. Such chemical modification strategies include, without limitation, pegylation, glycosylation, and acylation (Clark et al.: *J. Biol. Chem.* 271(36): 21969-21977, (1996); Roberts et al.: *Adv. Drug. Deliv. Rev.* 54(4): 459-476, (2002); Felix et al.: *Int. J. Pept. Protein. Res.* 46(3-4): 253-264, (1995); Garber A J: *Diabetes Obes. Metab.* 7(6): 666-74 (2005)). C- and N-terminal protecting groups and peptomimetic units may also be included.

A wide variety of PEG derivatives are both available and suitable for use in the preparation of PEG-conjugates. For example, NOF Corp.'s SUNBRIGHT® Series provides numerous PEG derivatives, including methoxypolyethylene glycols and activated PEG derivatives such as methoxy-PEG amines, maleimides, and carboxylic acids, for coupling by various methods to drugs, enzymes, phospholipids, and other biomaterials and Nektar Therapeutics' Advanced PEGylation also offers diverse PEG-coupling technologies to improve the safety and efficacy of therapeutics.

A search of patents, published patent applications, and related publications will also provide those skilled in the art reading this disclosure with significant possible PEG-coupling technologies and PEG-derivatives. For example, U.S. Pat. Nos. 6,436,386; 5,932,462; 5,900,461; 5,824,784; and 4,904,584; the contents of which are incorporated by reference in their entirety, describe such technologies and derivatives, and methods for their manufacture. Thus, one skilled in the art, considering both the disclosure of this invention and the disclosures of these other patents could couple PEG, a PEG-derivative, or some other polymer to C-peptide for its extended release.

PEG is a well-known polymer having the properties of solubility in water and in many organic solvents, lack of toxicity, lack of immunogenicity, and also clear, colorless, odorless, and stable. One use of PEG is to covalently attach the polymer to insoluble molecules to make the resulting PEG-molecule conjugate soluble. For these reasons and others, PEG has been selected as the preferred polymer for attachment, but it has been employed solely for purposes of illustration and not limitation. Similar products may be obtained with other water-soluble polymers, including without limitation; polyvinyl alcohol, other poly(alkylene oxides) such as poly(propylene glycol) and the like, poly(oxyethylated polyols) such as poly(oxyethylated glycerol) and the like, carboxymethylcellulose, dextran, polyvinyl alcohol, polyvinyl purrolidone, poly-1,3-dioxolane, poly-1,3,6-trioxane, ethylene/maleic anhydride, and polyaminoacids. One skilled in the art will be able to select the desired polymer based on the desired dosage, circulation time, resistance to proteolysis, and other considerations.

Isomers of the native L-amino acids, e.g., D-amino acids may be incorporated in any of the above forms of C-peptide, and used in any of the methods or kits of the invention. Additional variants may include amino and/or carboxyl terminal fusions as well as intrasequence insertions of single or multiple amino acids. Longer peptides may comprise multiple copies of one or more of the C-peptide sequences, such as any of Seq ID Nos. 1-33. Insertional amino acid sequence variants are those in which one or more amino acid residues are introduced at a site in the protein. Deletional variants are characterized by the removal of one or more amino acids from the sequence. Variants may include, e.g., different allelic variants as they appear in nature, e.g., in other species or due to geographical variation. All such variants, derivatives, fusion proteins, or fragments of C-peptide are included, may be used in any of the methods claims or kits disclosed herein, and are subsumed under the term "C-peptide".

The variants, derivatives, and fragments are functionally equivalent in that they have detectable C-peptide activity. More particularly, they exhibit at least 40%, preferably at least 60%, more preferably at least 80% of the activity of proinsulin C-peptide, particularly human C-peptide. Thus they are capable of functioning as proinsulin C-peptide, i.e., can substitute for C-peptide itself. Such activity means any activity exhibited by a native C-peptide, whether a physiological response exhibited in an in vivo or in vitro test system, or any biological activity or reaction mediated by a native C-peptide, e.g., in an enzyme assay or in binding to test tissues, membranes, or metal ions. Thus, it is known that C-peptide increases the intracellular concentration of calcium. An assay for C-peptide activity can thus be made by assaying for changes in intracellular calcium concentrations upon addition or administration of the peptide (e.g., fragment or derivative) in question. Such an assay is described in, e.g., Ohtomo Y et al. (*Diabetologia* 39: 199-205, (1996)), Kunt T et al. (*Diabetologia* 42(4): 465-471, (1999)), Shafqat J et al. (*Cell Mol. Life. Sci.* 59: 1185-1189, (2002)). Further, C-peptide has been found to induce phosphorylation of the MAP-kinases ERK 1 and 2 of a mouse embryonic fibroblast cell line (Swiss 3T3), and measurement of such phosphorylation and MAPK activation may be used to assess, or assay for C-peptide activity, as described, e.g., by Kitamura T et al. (*Biochem. J.* 355: 123-129, (2001)). C-peptide also has a well-known effect in stimulating $Na^+K^+$-ATPase activity and this also may form the basis of an assay for C-peptide activity, e.g., as described in WO 98/13384 or in Ohtomo Y et al. (supra) or Ohtomo Y et al. (*Diabetologia* 41: 287-291, (1998)). An assay for C-peptide activity based on endothelial nitric oxide synthase (eNOS) activity is also described in Kunt T et al. (supra) using bovine aortic cells and a reporter cell assay. Binding to particular cells may also be used to assess or assay for C-peptide activity, e.g., to cell membranes from human renal tubular cells, skin fibroblasts, and saphenous vein endothelial cells using fluorescence correlation spectroscopy, as described, e.g., in Rigler R et al. (*PNAS USA* 96: 13318-13323, (1999)), Henriksson M et al. (*Cell Mol. Life. Sci.* 57: 337-342, (2000)) and Pramanik A et al. (*Biochem Biophys. Res. Commun.* 284: 94-98, (2001)).

C-Peptide Therapeutic Dose Forms

Human C-peptide may be produced by recombinant technology, e.g., as a by-product in the production of human insulin from human proinsulin, or using genetically modified *E. coli* (see WO 1999007735) or synthetically using standard solid-phase peptide synthesis.

Administration of the C-peptide may be by any suitable method known in the medicinal arts, including oral, parenteral, topical, or subcutaneous administration, inhalation, or the implantation of a sustained delivery device or composition. In one aspect, administration is by subcutaneous administration. The C-peptide may be administered at any time during the day. For humans, the daily dosage used may range from about 0.1 to 10 mg/24 hours of C-peptide, e.g., from about 0.1 to 0.3 mg, about 0.3 to 1.5 mg, about 1.5 to 2.25 mg, about 2.25 to 3.0 mg, about 3.0 to 6.0 mg, and about 6.0 to 10 mg/24 hours. Preferably the total daily dose used is about 0.45 to 0.9 mg, about 0.6 to 1.2 mg, about 1.2 to 2.4 mg, or about 2.5 to 3.0 mg/24 hours. The total daily dose may be about 0.3 mg, about 0.45 mg, about 0.6 mg, about 0.9 mg, about 1.2 mg, about 1.5 mg, about 1.8 mg, about 2.1 mg, about 2.4 mg, about 2.7 mg, about 3.0 mg, about 3.3 mg, about 3.6 mg, about 3.9 mg, about 4.2 mg, or about 4.5 mg/24 hours. (It will be appreciated that masses of C-peptide referred to above are dependent on the bioavailability of the delivery system and based on the use of C-peptide with a molecular mass of approximately 3,020 Da).

In another aspect of any of these methods and kits, the therapeutic dose of C-peptide comprises a daily dose ranging from about 1.5 to about 4.5 mg per 24 hours. In another aspect of any of these methods and kits, the therapeutic dose of C-peptide comprises a daily dose ranging from about 0.3 mg to about 1.5 mg per 24 hours. In another aspect of any of these methods and kits, the therapeutic dose of C-peptide comprises a daily dose ranging from about 3.0 mg to about 6 mg per 24 hours. In another aspect of any of these methods and kits, the therapeutic dose of C-peptide maintains the average steady state concentration of C-peptide ($C_{ss\text{-}ave}$) in the patient's plasma of between about 0.2 nM and about 6 nM.

In another aspect of any of these methods and kits, the therapeutic dose of C-peptide is provided to the patient so as to maintain the average steady state concentration of C-peptide in the patient's plasma between about 0.2 nM and about 6 nM for at least 24 hours. In another aspect of any of these methods and kits, the therapeutic dose of C-peptide is provided to the patient so as to maintain the average steady state concentration of C-peptide in the patient's plasma between about 0.2 nM and about 6 nM for at least 48 hours. In another aspect of any of these methods and kits, the therapeutic dose of C-peptide is provided to the patient so as to maintain the average steady state concentration of C-peptide in the patient's plasma between about 0.2 nM and about 6 nM for at least 72 hours. In another aspect of any of these methods and kits, the therapeutic dose of C-peptide is provided to the patient so as to maintain the average steady state concentration of C-peptide in the patient's plasma between about 0.2 nM and about 6 nM for at least one week. In any of these methods and kits, the therapeutic dose is administered by daily subcutaneous injections. In another aspect of any of these methods and kits, the therapeutic dose is administered by a sustained release formulation or device.

It will be further appreciated that for sustained delivery devices and compositions the total dose of C-peptide contained in such delivery system will be correspondingly larger depending upon the release profile of the sustained release system. Thus, a sustained release composition or device that is intended to deliver C-peptide over a period of 5 days will typically comprise at least about 5 to 10 times the daily dose of C-peptide; a sustained release composition or device that is intended to deliver C-peptide over a period of 365 days will typically comprise at least about 400 to 600 times the daily dose of C-peptide (depending upon the stability and bioavailability of C-peptide when administered using the sustained release system). Typically such devices and systems will maintain an average steady state concentration of C-peptide in the patient's plasma of between about 0.2 nM and about 6 nM.

In one aspect of any of these modes of administration, the total daily dose of C-peptide may be administered in multiple, single doses throughout the day to maintain the steady-state level of C-peptide above the minimum effective therapuetic level. The size of the single dose as administered will vary depending on the frequency of administration and bioavailability, but may typically be in the region of about 0.15 to 6.0 mg, about 0.15 to 4.5 mg, about 0.15 to 3.0 mg, about 0.15 to 2.4 mg, about 0.15 to 1.8 mg, or about 0.15 to 1.2 mg. Other ranges include about 0.1 to 4.5 mg, about 0.3 to 0.6 mg, about 0.3 to 1.5 mg, or about 0.5 to 3.0 mg. Representative single doses include about 5.0 mg, about 4.5 mg, about 4.0 mg, about 3.5 mg, about 3.0 mg, about 2.5 mg, about 2.0 mg, about 1.5 mg, about 1.0 mg, or about 0.5 mg. In one aspect, the dosing interval of such multiple administration regimens will be about 3 hours between doses, or about 4 hours between doses, or about 6 hours between doses.

In one aspect of any of these methods and kits, the dose and dosing interval of C-peptide administered may vary depending on the time of administration. For example, a total daily dose of 1.8 mg/24 hours may be divided into 4 doses; 0.45 mg in the morning (06:00-10:00); at lunch (11:00-14:00); at dinner (16:00-19:00); and 0.9 mg at bedtime (20:00-24:00). Typically such dosing schedules maintain the average steady-state C-peptide level in the blood above the minimum effective therapeutic level for at least 50% of the time for any one 24 hour dosing period. In a preferred aspect, the dosing schedule maintains the C-peptide level in the blood above the minimum effective therapeutic level for at least 75% of the time for any one 24 hour dosing period. In a more preferred aspect, the dosing schedule maintains the C-peptide level in the blood above the minimum effective therapeutic level for at least 85% of the time for any one 24 hour dosing period. In another aspect of any of these modes of administration, the total daily dose of C-peptide may be administered continuously throughout the day to coordinate C-peptide levels with insulin levels, meals, or periods of exercise, sleep, or any other patient-specific clinical parameter or biomarker.

The dose may or may not be in solution. If the dose is administered in solution, it will be appreciated that the volume of the dose may vary, but will typically be 10 μL-2 mL. Preferably the dose for S.C. administration will be given in a volume of 1000 uL, 900 μL, 800 μL, 700 μL, 600 μL, 500 μL, 400 μL, 300 μL, 200 μL, 100 μL, 50 μL, or 20 μL. Sustained release compositions and depot formulations may include doses in volumes of about 2 mL to about 50 uL.

C-peptide doses in solution can also comprise a preservative and/or a buffer. For example, the preservative m-cresol can be used. Typical concentrations of preservatives include 0.5 mg/mL, 1 mg/mL, 2 mg/mL, 3 mg/mL, 4 mg/mL, or 5 mg/mL. Thus, a range of concentration of preservative may include 0.2 to 10 mg/mL, particularly 0.5 to 6 mg/mL, or 0.5 to 5 mg/mL. Examples of buffers that can be used include histidine (pH 6.0), sodium phosphate buffer (pH 7.3), or sodium bicarbonate buffer (pH 7.3). It will be appreciated that the C-peptide dose may comprise one or more of a native or intact C-peptide, fragments, derivatives, or other functionally equivalent variants of C-peptide.

A dose of C-peptide may comprise full-length human C-peptide (Seq ID No. 1) and the C-terminal C-peptide fragment EGSLQ (Seq ID No. 31) and/or a C-peptide homolog or C-peptide derivative. Further, the dose may if desired only contain a fragment of C-peptide, e.g., EGSLQ. Thus, the term "C-peptide" may encompass a single C-peptide entity or a mixture of different "C-peptides".

Pharmaceutical compositions for use in the present invention may be formulated according to techniques and procedures well-known in the art and widely discussed in the literature and may comprise any of the known carriers, diluents, or excipients. In one aspect, the compositions may be in the form of sterile aqueous solutions and/or suspensions of the pharmaceutically active ingredients, aerosols, ointments, and the like. Formulations which are aqueous solutions are most preferred. Such formulations typically contain the C-peptide itself, water, and one or more buffers which act as stabilizers (e.g., phosphate-containing buffers) and optionally one or more preservatives. Such formulations containing, e.g., about 0.3 to 12.0 mg, about 0.3 to 10.0 mg, about 0.3 to 8.0 mg, about 0.3 to 6.0 mg, about 0.3 to 4.0 mg, about 0.3 to 3.0 mg, or any of the ranges mentioned above, e.g., about 12 mg, about 10 mg, about 8 mg, about 6 mg, about 5 mg, about 4 mg, about 3 mg, about 2 mg, or about 1 mg of the C-peptide and constitute a further aspect of the invention.

Pharmaceutical compositions may include pharmaceutically acceptable salts of C-peptide. For a review on suitable salts, see *Handbook of Pharmaceutical Salts: Properties, Selection, and Use* by Stahl and Wermuth (Wiley-VCH, 2002). Suitable base salts are formed from bases which form non-toxic salts. Representative examples include the aluminium, arginine, benzathine, calcium, choline, diethylamine, diolamine, glycine, lysine, magnesium, meglumine, olamine, potassium, sodium, tromethamine, and zinc salts. Hemisalts of acids and bases may also be formed, e.g., hemisulphate and hemicalcium salts. In one embodiment, C-peptide may be prepared as a gel with a pharmaceutically acceptable positively charged ion. In one aspect, the positively charged ion may be a divalent metal ion. In one aspect, the metal ion is selected from calcium, magnesium, and zinc.

Compositions to be used in the invention suitable for parenteral administration may comprise sterile aqueous solutions and/or suspensions of the pharmaceutically active ingredients preferably made isotonic with the blood of the recipient, generally using sodium chloride, glycerin, glucose, mannitol, sorbitol, and the like.

Compositions of the invention suitable for oral administration may, e.g., comprise peptides in sterile purified stock powder form preferably covered by an envelope or envelopes (enterocapsules) protecting from degradation of the peptides in the stomach and thereby enabling absorption of these substances from the gingiva or in the small intestines. The total amount of active ingredient in the composition may vary from 99.99 to 0.01 percent of weight.

Methods for Administration of C-Peptide

Pharmaceutical compositions suitable for the delivery of C-peptide and methods for their preparation will be readily apparent to those skilled in the art. Such compositions and methods for their preparation may be found, e.g., in *Remington's Pharmaceutical Sciences,* 19th Edition (Mack Publishing Company, 1995).

Pharmaceutical compositions of C-peptide may be administered directly into the blood stream, into muscle, or into an internal organ. Suitable means for parenteral administration include intravenous, intra-arterial, intraperitoneal, intrathecal, intraventricular, intraurethral, intrasternal, intracranial, intramuscular, intrasynovial, and subcutaneous. Suitable devices for parenteral administration include needle (including microneedle) injectors, needle-free injectors, and infusion techniques. Subcutaneous administration of C-peptide is preferred. Subcutaneous administration of C-peptide will typically not be into the same site as that most recently used for insulin administration. In one aspect of any of the claimed methods and kits, C-peptide is administered to the opposite side of the abdomen to the site most recently used for insulin administration. In another aspect of any of the claimed methods and kits, C-peptide is administered to the upper arm. In another aspect of any of the claimed methods and kits, C-peptide is administered to the abdomen. In another aspect of any of the claimed methods and kits, C-peptide is administered to the upper area of the buttock. In another aspect of any of the claimed methods and kits, C-peptide is administered to the front of the thigh.

Parenteral formulations are typically aqueous solutions which may contain excipients such as salts, carbohydrates, and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, e.g., by lyophilization, may readily be accomplished using standard pharmaceutical techniques well-known to those skilled in the art.

Formulations for parenteral administration may be formulated to be immediate and/or sustained release. Sustained release compositions include delayed, modified, pulsed, controlled, targeted and programmed release. Thus C-peptide may be formulated as a suspension or as a solid, semi-solid, or thixotropic liquid for administration as an implanted depot providing sustained release of C-peptide. Examples of such formulations include without limitation, drug-coated stents and semi-solids and suspensions comprising drug-loaded poly(DL-lactic-co-glycolic)acid (PGLA), poly(DL-lactide-co-glycolide) (PLG) or poly(lactide) (PLA) lamellar vesicles or microparticles, hydrogels (Hoffman A S: Ann. N.Y. Acad. Sci. 944: 62-73 (2001)), poly-amino acid nanoparticles systems, such as the Medusa system developed by Flamel Technologies Inc., non aequous gel systems such as Atrigel developed by Atrix, Inc., and SABER (Sucrose Acetate Isobutyrate Extended Release) developed by Durect Corporation, and lipid-based systems such as DepoFoam developed by SkyePharma.

Sustained release devices capable of delivering desired doses of C-peptide over extended periods of time are known in the art. For example, U.S. Pat. Nos. 5,034,229; 5,557,318; 5,110,596; 5,728,396; 5,985,305; 6,113,938; 6,156,331; 6,375,978; and 6,395,292; teach osmotically-driven devices capable of delivering an active agent formulation, such as a solution or a suspension, at a desired rate over an extended period of time (i.e., a period ranging from more than one week up to one year or more). Other exemplary sustained release devices include regulator-type pumps that provide constant flow, adjustable flow, or programmable flow of beneficial agent formulations, which are available from, e.g., Insulet Corporation, Codman of Raynham, Mass., (sold under the trademark OMNIPODT™ Insulin Management System), Medtronic of Minneapolis, Minn., Intarcia Therapeutics of Hayward, Calif., and Tricumed Medinzintechnik GmbH of Germany. Further examples of devices are described in U.S. Pat. Nos. 6,283,949; 5,976,109; 5,836,935; and 5,511,355.

Generally, in an osmotic pump system, a core is encased by a semi-permeable membrane having at least one orifice. The semi-permeable membrane is permeable to water, but impermeable to the active agent. When the system is exposed to body fluids, water penetrates through the semi-permeable membrane into the core containing osmotic excipients and the active agent. Osmotic pressure increases within the core and the agent is displaced through the orifice at a controlled, predetermined rate.

In many osmotic pumps, the core contains more than one internal compartment. For example, a first compartment may contain the active agent. A second compartment contains an osmotic agent and/or "driving member." See, e.g., U.S. Pat. No. 5,573,776, the contents of which are incorporated herein by reference. This compartment may have a high osmolality, which causes water to flux into the pump through the semi permeable membrane. The influx of water compresses the first compartment. This can be accomplished, e.g., by using a polymer in the second compartment, which swells on contact with the fluid. Accordingly, the agent is displaced at a predetermined rate.

In another embodiment, the osmotic pump may comprise more than one active agent-containing compartment, with each compartment containing the same agent or a different agent. The concentrations of the agent in each compartment, as well as the rate of release, may also be the same or different.

The rate of delivery is generally controlled by the water permeability of the semi-permeable membrane. Thus, the delivery profile of the pump is independent of the agent dispensed, and the molecular weight of an agent, or its physical and chemical properties, generally have no bearing on its rate of delivery. Further discussion regarding the principle of operation, the design criteria, and the delivery rate for osmotic pumps is provided in Theeuwes and Yum (*Ann. of Biomed. Eng.* 4(4): 343-353, (1976)) and Urquhart J et al. (*Ann. Rev. Pharmacol. Toxicol.* 24:199-236, (1984)), the contents of which are incorporated by reference.

Sustained release devices based on osmotic pumps are well-known in the art and readily available to one of ordinary skill in the art from companies experienced in providing osmotic pumps for extended release drug delivery. For example, the technology sold under the trademark DUROS® which was originally developed by ALZA is an implantable, nonbiodegradable, osmotically-driven system that enables delivery of small drugs, peptides, proteins, DNA, and other bioactive macromolecules for up to one year; ALZA's technology sold under the trademark OROS® embodies tablets that employ osmosis to provide precise, controlled drug delivery for up to 24 hours; Osmotica Pharmaceutical's system sold under the trademark OSMODEX® includes a tablet, which may have more than one layer of the drug(s) with the same or different release profiles; Shire Laboratories' system sold under the trademark ENSOTROI® solubilizes drugs within the core and delivers the solubilized drug through a laser-drilled hole by osmosis; and osmotic pumps sold under the trademark ALZET® are miniature, implantable pumps used for research in mice, rats, and other laboratory animals.

A search of patents, published patent applications, and related publications will also provide those skilled in the art reading this disclosure with significant possible osmotic pump technologies. For example, U.S. Pat. Nos. 6,890,918; 6,838,093; 6,814,979; 6,713,086; 6,534,090; 6,514,532; 6,361,796; 6,352,721; 6,294,201; 6,284,276; 6,110,498; 5,573,776; 4,200,0984; and 4,088,864; the contents of which are incorporated herein by reference, describe osmotic pumps and methods for their manufacture. One skilled in the art, considering both the disclosure of this invention and the disclosures of these other patents, could produce an osmotic pump for the sustained release of C-peptide.

Typical materials for the semi-permeable membrane include semi-permeable polymers known to the art as osmosis and reverse osmosis membranes, such as cellulose acylate, cellulose diacylate, cellulose triacylate, cellulose acetate, cellulose diacetate, cellulose triacetate, agar acetate, amylase triacetate, beta glucan acetate, acetaldehyde dimethyl acetate, cellulose acetate ethyl carbamate, polyamides, plyurethanes, sulfonated polystyrenes, cellulose acetate phthalate, cellulose acetate methyl carbamate, cellulose acetate succinate, cellulose acetate dimethyl aminoacetate, cellulose acetate ethyl carbamate, cellulose acetate chloracetate, cellulose dipalmitate, cellulose dioctanoate, cellulose dicaprylate, cellulose dipentanlate, cellulose acetate valerate, cellulose acetate succinate, cellulose propionate, succinate, methyl cellulose, cellulose acetate p-toluene sulfonate, cellulose acetate butyrate, cross-linked selectively semi-permeable polymers formed by the coprecipitation of a polyanion and a polycation, semi-permeable polymers, lightly cross-linked polystyrene derivatives, cross-linked poly(sodium styrene sulfonate), poly(vinylbenzyltrimethyl ammonium chloride), cellulose acetate having a degree of substitution up to 1 and an acetyl content up to 50%, cellulose diacetate having a degree of substitution of 1 to 2 and an acetyl content of 21 to 35%, cellulose triacetate having a degree of substitution of 2 to 3 and an acetyl content of 35 to 44.8%, as disclosed in U.S. Pat. No. 6,713,086, the contents of which are incorporated herein by reference.

The osmotic agent(s) present in the pump may comprise any osmotically effective compound(s) that exhibit an osmotic pressure gradient across the semi-permeable wall against the exterior fluid. Effective agents include, without limitation, magnesium sulfate, calcium sulfate, magnesium chloride, sodium chloride, lithium chloride, potassium sulfate, sodium carbonate, sodium sulfite, lithium sulfate, potassium chloride, sodium sulfate, d-mannitol, urea, sorbitol, inositol, raffinose, sucrose, flucose, hydrophilic polymers such as cellulose polymers, mixtures thereof, and the like, as disclosed in U.S. Pat. No. 6,713,086, the contents of which are incorporated herein by reference.

The "driving member" is typically a hydrophilic polymer that interacts with biological fluids and swells or expands. The polymer exhibits the ability to swell in water and retain a significant portion of the imbibed water within the polymer structure. The polymers swell or expand to a very high degree, usually exhibiting a 2- to 50-fold volume increase. The polymers can be non-cross-linked or cross-linked. Hydrophilic polymers suitable for the present purpose are well-known in the art.

The orifice may comprise any means and methods suitable for releasing the active agent from the system. The osmotic pump may include one or more apertures or orifices that have been bored through the semi-permeable membrane by mechanical procedures known in the art, including, but not limited to, the use of lasers as disclosed in U.S. Pat. No 4,088,864. Alternatively, it may be formed by incorporating an erodible element, such as a gelatin plug, in the semi-permeable membrane.

Because they can be designed to deliver a desired active agent at therapeutic levels over an extended period of time, implantable delivery systems can advantageously provide long-term therapeutic dosing of a desired active agent without requiring frequent visits to a healthcare provider or repetitive self-medication. Therefore, implantable delivery devices can work to provide increased patient compliance, reduced irritation at the site of administration, fewer occupational hazards for healthcare providers, reduced waste hazards, and increased therapeutic efficacy through enhanced dosing control.

Among other challenges, two problems must be addressed when seeking to deliver biomolecular material over an extended period of time from an implanted delivery device. First, the biomolecular material must be contained within a formulation that substantially maintains the stability of the material at elevated temperatures (i.e., 37° C. and above) over the operational life of the device. Second, the biomolecular material must be formulated in a way that allows delivery of the biomolecular material from an implanted device into a desired environment of operation over an extended period time. This second challenge has proven particularly difficult where the biomolecular material is included in a flowable composition that is delivered from a device over an extended period of time at low flow rates (i.e., 100 μL/day).

Peptide drugs such as C-peptide may degrade via one or more of several different mechanisms, including deamidation, oxidation, hydrolysis, and racemization. Significantly, water is a reactant in many of the relevant degradation pathways. Moreover, water acts as a plasticizer and facilitates the unfolding and irreversible aggregation of biomolecular materials. To work around the stability problems created by aqueous formulations of biomolecular materials, dry powder formulations of biomolecular materials have been created using known particle formation processes, such as by known lyophilization, spray-drying, or desiccation techniques. Though dry powder formulations of biomolecular material have been shown to provide suitable stability characteristics, it would be desirable to provide a formulation that is not only stable over extended periods of time, but is also flowable and readily deliverable from an implantable delivery device.

Accordingly in one aspect of any of the claimed methods and kits, the C-peptide is provided in a nonaqueous drug formulation, and is delivered from a sustained release implantable device, wherein the C-peptide is stable for at least two months of time at 37° C.

Representative nonaqueous formulations for C-peptide include those disclosed in International Publication Number WO00/45790 that describes nonaqueous vehicle formulations that are formulated using at least two of a polymer, a solvent, and a surfactant.

WO98/27962 discloses an injectable depot gel composition containing a polymer, a solvent that can dissolve the polymer and thereby form a viscous gel, a beneficial agent, and an emulsifying agent in the form of a dispersed droplet phase in the viscous gel.

WO04089335 discloses nonaqueous vehicles that are formed using a combination of polymer and solvent that results in a vehicle that is miscible in water. As it is used herein, the term "miscible in water" refers to a vehicle that, at a temperature range representative of a chosen operational environment, can be mixed with water at all proportions without resulting in a phase separation of the polymer from the solvent such that a highly viscous polymer phase is formed. For the purposes of the present invention, a "highly viscous polymer phase" refers to a polymer containing composition that exhibits a viscosity that is greater than the viscosity of the vehicle before the vehicle is mixed with water.

Accordingly in another aspect of any of the claimed methods and kits, C-peptide is provided in a sustained release device comprising: a reservoir having at least one drug delivery orifice, and a stable nonaqueous drug formulation. In one aspect of these methods and kits, the formulation comprises: at least C-peptide; and a nonaqueous, single-phase vehicle comprising at least one polymer and at least one solvent, the vehicle being miscible in water, wherein the drug is insoluble in one or more vehicle components and the C-peptide formulation is stable at 37° C. for at least two months. In one aspect, the solvent is selected from the group consisting of glycofurol, benzyl alcohol, tetraglycol, n-methylpyrrolidone, glycerol formal, propylene glycol, and combinations thereof.

In particular, a nonaqueous formulation is considered chemically stable if no more than about 35% of the C-peptide is degraded by chemical pathways, such as by oxidation, deamidation, and hydrolysis, after maintenance of the formulation at 37° C. for a period of two months, and a formulation is considered physically stable if, under the same conditions, no more than about 15% of the C-peptide contained in the formulation is degraded through aggregation. A drug formulation is stable according to the present invention if at least about 65% of the C-peptide remains physically and chemically stable after about two months at 37° C.

C-peptide for use in the present invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages, and microemulsions. Liposomes may also be used. Typical carriers include alcohol, water, mineral oil, liquid petrolatum, white petrolatum, glycerin, polyethylene glycol, and propylene glycol. Penetration enhancers may be incorporated—see, e.g., Finnin and Morgan: J. Pharm. Sci. 88(10): 955-958, (1999). Other means of topical administration include delivery by electroporation, iontophoresis, phonophoresis, sonophoresis, and microneedle or needle-free injection (e.g., the systems sold under the trademarks POWDERJECT™, BIOJECTT™).

Formulations for topical administration may be formulated to be immediate and/or modified release. Modified release formulations include delayed, sustained, pulsed, controlled, targeted and programmed release.

In another embodiment of a sustained release composition of C-peptide, the C-peptide is packaged in a liposome, which has demonstrated utility in delivering beneficial active agents in a controlled manner over prolonged periods of time. Liposomes are completely closed bilayer membranes containing an entrapped aqueous volume. Liposomes may be unilamellar vesicles possessing a single membrane bilayer or multilamellar vesicles with multiple membrane bilayers, each separated from the next by an aqueous layer. The structure of the resulting membrane bilayer is such that the hydrophobic (non-polar) tails of the lipid orient toward the center of the bilayer while the hydrophilic (polar) heads orient towards the aqueous phase.

Generally, in a liposome-drug delivery system, the active agent is entrapped in the liposome and then administered to the patient to be treated. However, if the active agent is lipophilic, it may associate with the lipid bilayer. The immune system may recognize conventional liposomes as foreign bodies and destroy them before significant amounts of the active agent reaches the intended disease site. Thus in one embodiment, the liposome may be coated with a flexible water-soluble polymer that avoids uptake by the organs of the mononuclear phagocyte system, primarily the liver and spleen. Suitable hydrophilic polymers for surrounding the liposomes include, without limitation, polyethylene glycol (PEG), polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxethylacrylate, hydroxymethylcellulose hydroxyethylcellulose, polyethyleneglycol, polyaspartamide and hydrophilie peptide sequences as described in U.S. Pat. Nos. 6,316,024; 6,126,966; 6,056,973; 6,043,094; the contents of which are incorporated by reference in their entirety.

Liposomes may be comprised of any lipid or lipid combination known in the art. For example, the vesicle-forming lipids may be naturally-occurring or synthetic lipids, including phospholipids, such as phosphatidylcholine, phosphatidylethanolamine, phosphatidic acid, phosphatidylserine, phasphatidylglycerol, phosphatidylinositol, and sphingomyelin as disclosed in U.S. Pat. Nos. 6,056,973 and 5,874,104. The vesicle-forming lipids may also be glycolipids, cerebrosides, or cationic lipids, such as 1,2-dioleyloxy-3-(trimethylamino) propane (DOTAP); N-;I-(2,3-ditetradecyloxy)propyl; -N,N-dimethyl-N-hydroxyethylammonium bromide (DMRIE); N 2,3-dioleyloxy)propyl; N,N-dimethyl-N-hydroxy ethylammonium bromide (DORIE); N;I-(2,3-dioleyloxy)propyl N,N,N-trimethylammonium chloride (DOTMA); 3; N—(N',N'-dimethylaminoethane) carbamoly; cholesterol (DC-Choi); or dimethyldioctadecylamnionium (DDAB) also as disclosed in U.S. Pat. No. 6,056,973. Cholesterol may also be present in the proper range to impart stability to the vesicle as disclosed in U.S. Pat. Nos. 5,916,588 and 5,874,104.

The liposomes for use in any of the methods or kits of the invention can be manufactured by standard techniques known to those of skill in the art. For example, in one embodiment, as disclosed in U.S. Pat. No. 5,916,588, a buffered solution of the active agent is prepared. Then a suitable lipid, such as hydrogenated soy phosphatidylcholine, and cholesterol, both in powdered form, are dissolved in chloroform or the like and dried by rotoevaporation. The lipid film thus formed is resuspended in diethyl ether or the like and placed in a flask, and sonicated in a water bath during addition of the buffered solution of the active agent. Once the ether has evaporated, sonication is discontinued and a stream of nitrogen is applied until residual ether is removed. Other standard manufacturing procedures are described in U.S. Pat. Nos. 6,352,716; 6,294, 191; 6,126,966; 6,056,973; 5,965,156; and 5,874,104. The liposomes of this invention can be produced by any method generally accepted in the art for making liposomes, including, without limitation, the methods of the above-cited documents (the contents of which are incorporated herein by reference).

Liposomes are also well-known in the art and readily available from companies experienced in providing liposomes for extended release drug delivery. For example, ALZA's (formerly Sequus Pharmaceutical's) liposomal technology for intravenous drug delivery sold under the trademark STEALTH® uses a polyethylene glycol coating on liposomes to evade recognition by the immune system; Gilead Sciences (formerly Nexstar's) liposomal technology sold under the trademark AMBISOME®, and FDA approved treatment for fungal infections; and NOF Corp. offers a wide variety of Good Manufacturing Practice (GMP)-grade phospholipids, phospholipids derivatives, and PEG-phospholipids sold under the tradenames COATSOME® and SUNBRIGHT®.

A search of patents, published patent applications, and related publications will also provide those skilled in the art reading this disclosure with significant possible liposomal technologies. U.S. Pat. Nos. 6,759,057; 6,406,713; 6,352, 716; 6,316,024; 6,294,191; 6,126,966; 6,056,973; 6,043,094; 5,965,156; 5,916,588; 5,874,104; 5,215,680; and 4,684,479; the contents of which are incorporated herein by reference, describe liposomes and lipid-coated microbubbles, and methods for their manufacture. Thus, one skilled in the art, considering both the disclosure of this invention and the disclosures of these other patents could produce a liposome for the sustained release of C-peptide.

In another embodiment of the present invention, the sustained release of C-peptide into the blood comprises a sustained release composition comprising C-peptide that is packaged in a microsphere. Microspheres have demonstrated utility in delivering beneficial active agents to a target area in a controlled manner over prolonged periods of time. Microspheres are generally biodegradable and can be used for subcutaneous, intramuscular, and intravenous administration.

Generally, each microsphere is composed of an active agent and polymer molecules as disclosed in U.S. Pat. No. 6,268,053, the active agent may be centrally located within a membrane formed by the polymer molecules, or, alternatively, dispersed throughout the microsphere because the internal structure comprises a matrix of the active agent and a polymer excipient. Typically, the outer surface of the microsphere is permeable to water, which allows aqueous fluids to enter the microsphere, as well as solubilized active agent and polymer to exit the microsphere.

In one embodiment, the polymer membrane comprises cross-linked polymers as disclosed in U.S. Pat. No. 6,395,302. When the pore sizes of the cross-linked polymer are equal or smaller than the hydrodynamic diameter of the active agent, the active agent is essentially released when the polymer is degraded. On the other hand, if the pore sizes of the cross-linked polymers are larger than the size of the active agent, the active agent is at least partially released by diffusion.

Additional methods for making microsphere membranes are known and used in the art and can be used in the practice of the invention disclosed herein. Typical materials for the outer membrane include the following categories of polymers: (1) carbohydrate-based polymers, such as methylcellulose, carboxymethyl cellulose-based polymers, dextran, polydextrose, chitins, chitosan, and starch (including hetastarch), and derivatives thereof; (2) polyaliphatic alcohols such as polyethylene oxide and derivatives thereof including PEG, PEG-acrylates, polyethyleneimine, polyvinyl acetate, and derivatives thereof; (3) polyvinyl polymers such as polyvinyl alcohol, polyvinylpyrrolidone, poly(vinyl) phosphate, poly(vinyl)phosphonic acid, and derivatives thereof; (4) polyacrylic acids and derivatives thereof; (5) polyorganic acids, such as polymaleic acid, and derivatives thereof; (6) polyamino acids, such as polylysine, and polyimino acids, such as polyimino tyrosine, and derivatives thereof; (7) co-polymers and block co-polymers, such as poloxamer 407 or Pluronic L-101; polymer, and derivatives thereof; (8) tert-polymers and derivatives thereof; (9) polyethers, such as poly(tetramethylene ether glycol), and derivatives thereof; (10) naturally-occurring polymers, such as zein, chitosan and pullulan, and derivatives thereof; (11) polyimids, such as poly n-tris(hydroxymethyl)methylmethacrylate, and derivatives thereof; (12) surfactants, such as polyoxyethylene sorbitan, and derivatives thereof; (13) polyesters such polyethylene glycol) (n) monomethyl ether mono(succinimidyl succinate)ester, and derivatives thereof; (14) branched and cyclo-polymers, such as branched PEG and cyclodextrins, and derivatives thereof; and (15) polyaldehydes, such as poly(perfluoropropylene oxide-b-perfluoroformaldehyde), and derivatives thereof as disclosed in U.S. Pat. No. 6,268,053, the contents of which are incorporated herein by reference. Other typical polymers known to those of ordinary skill in the art include poly(lactide-co-glycolide), polylactide homopolymer; polyglycolide homopolymer; polycaprolactone; polyhydroxybutyrate-polyhydroxyvalerate copolymer; poly(lactide-co-caprolactone); polyesteramides; polyorthoesters; poly 13-hydroxybutyric acid; and polyanhydrides as disclosed in U.S. Pat. No. 6,517,859, the contents of which are incorporated herein by reference.

In one embodiment, the microsphere of the present invention are attached to or coated with additional molecules. Such molecules can facilitate targeting, enhance receptor mediation, and provide escape from endocytosis or destruction. Typical molecules include phospholipids, receptors, antibodies, hormones, and polysaccharides. Additionally, one or more cleavable molecules may be attached to the outer surface of microspheres to target it to a predetermined site. Then, under appropriate biological conditions, the molecule is cleaved causing release of the microsphere from the target.

The microspheres for use in the sustained release compositions are manufactured by standard techniques. For example, in one embodiment, volume exclusion is performed by mixing the active agent in solution with a polymer or mixture of polymers in solution in the presence of an energy source for a sufficient amount of time to form particles as disclosed in U.S. Pat. No. 6,268,053. The pH of the solution is adjusted to a pH near the isoelectric point (pI) of the macromolecule. Next, the solution is exposed to an energy source, such as heat, radiation, or ionization, alone or in combination with sonication, vortexing, mixing or stirring, to form microparticles. The resulting microparticles are then separated from any unincorporated components present in the solution by physical separation methods well-known to those skilled in the art and may then be washed. Other standard manufacturing procedures are described in U.S. Pat. Nos. 6,669,961; 6,517,859; 6,458,387; 6,395,302; 6,303,148; 6,268,053; 6,090,925; 6,024,983; 5,942,252; 5,981,719; 5,578,709; 5,554,730; 5,407,609; 4,897,268; and 4,542,025; the contents of which are incorporated by reference in their entirety. Microspheres are well-known and readily available to one of ordinary skill in the art from companies experienced in providing such technologies for extended release drug delivery. For example, Epic Therapeutics, a subsidiary of Baxter Healthcare Corp., developed, a protein-matrix drug delivery system sold under the trademark PROMAXX® that produces bioerodible protein microspheres in a totally water-based process; OctoPlus developed, cross-linked dextran microspheres sold under the trademark OCTODEX® that release active ingredients based on bulk degradation of matrix rather than based on surface erosion.

A search of patents, published patent applications, and related publications will also provide those skilled in the art reading this disclosure with significant possible microsphere technologies for use in formulating sustained release compositions. For example, U.S. Pat. Nos. 6,669,961; 6,517,859; 6,458,387; 6,395,302; 6,303,148; 6,268,053; 6,090,925; 6,024,983; 5,942,252; 5,981,719; 5,578,709; 5,554,730; 5,407,609; 4,897,268; and 4,542,025; the contents of which are incorporated by reference in their entirety, describe microspheres and methods for their manufacture. One skilled in the art, considering both the disclosure of this invention and the disclosures of these other patents could make and use microspheres for the sustained release of C-peptide for use in any of the methods or kits claimed herein.

The C-peptide can be administered intranasally or by inhalation, typically in the form of a dry powder (either alone, as a mixture, e.g., in a dry blend with lactose, or as a mixed component particle, e.g., mixed with phospholipids, such as phosphatidylcholine) from a dry powder inhaler, as an aerosol spray from a pressurized container, pump, spray, atomizer (preferably an atomizer using electro hydrodynamics to produce a fine mist), or nebulizer, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, e.g., chitosan or cyclodextrin.

The pressurized container, pump, spray, atomizer, or nebulizer contains a solution or suspension of the compound(s) of the invention comprising, e.g., ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 μm). This may be achieved by any appropriate method, such as spiral jet milling, fluid bed jet milling, supercritical fluid processing to form nanoparticles, high pressure homogenization, or spray drying.

Capsules (made, e.g., from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose, and trehalose.

A suitable solution formulation for use in an atomizer using electro hydrodynamics to produce a fine mist may contain from 1 µg to 20 mg of C-peptide per actuation and the actuation volume may vary from 1 µL to 100 µL. A typical formulation may comprise C-peptide propylene glycol, sterile water, ethanol, and sodium chloride. Alternative solvents that may be used instead of propylene glycol include glycerol and polyethylene glycol. Suitable flavors, such as menthol and levomenthol, or sweeteners, such as saccharin or saccharin sodium, may be added to those formulations of the invention intended for inhaled/intranasal administration. Formulations for inhaled/intranasal administration may be formulated to be immediate and/or modified release using, e.g., PGLA. Modified release formulations include delayed, sustained, pulsed, controlled, targeted, and programmed release.

In the case of dry powder inhalers and aerosols, the dosage unit is determined by means of a valve that delivers a metered amount. Units in accordance with the invention are typically arranged to administer a metered dose or "puff" containing from 0.1 mg to 10 mg of C-peptide. The overall daily dose will typically be in the range 0.1 mg to 20 mg that may be administered in a single dose or, more usually, as divided doses throughout the day.

Kits are also contemplated for this invention. A typical kit would comprise a container, preferably a vial, for the C-peptide formulation comprising C-peptide in a pharmaceutically acceptable formulation, and instructions, and/or a product insert or label. In one aspect, the instructions include a dosing regimen for administration of said C-peptide to an insulin-dependent patient to reduce the risk, incidence, or severity of hypoglycemia. In one aspect, the kit includes instructions to reduce the administration of insulin by about 5% to about 35% when starting C-peptide therapy. In another aspect, the instructions include directions for the patient to closely monitor their blood glucose levels when starting C-peptide therapy. In another aspect, the instructions include directions for the patient to avoid situations or circumstances that might predispose the patient to hypoglycemia when starting C-peptide therapy.

EXAMPLES

Example 1

Demonstration of Altered Insulin Requirements During C-Peptide Therapy

I Overall Study Design

The study was a multicenter, double-blind, randomized, placebo-controlled phase II trial comparing the effect of subcutaneous injection (S.C.) of 500 nmoL/24 h (1.5 mg) C-peptide; 1,500 nmoL/24 h (4.5 mg) C-peptide and placebo treatment for 6 months in type 1 diabetes patients with peripheral neuropathy.

Five clinical centers participated in this study and patients were recruited to the study by advertisement and by screening of hospital records. Patients who were found eligible and who declared a willingness to participate, were invited to participate in the study and were subsequently screened for inclusion and exclusion criteria.

At the initial screening/baseline visit (S/B visit) the patients were assigned a screening number (starting with site number 1001). Written informed consent was obtained. Demographic data, medical history, concomitant medication including insulin regimen were recorded in addition to results from a physical examination and electrocardiography (ECG). Furthermore, two neurophysiological examinations were performed within 2-14 days, and neurological examination including symptom assessment were performed. Urine samples and blood samples for hematology, clinical chemistries, and metabolic control (HbA1c) as well as for study specific tests, i.e., C-peptide plasma levels and C-peptide antibodies were also drawn. In women of childbearing potential, pregnancy was excluded by assessment of human chorion gonadotropine (HCG). In addition, autonomic nerve function was assessed by determination of the expiration/inspiration ratio (E/I ratio) during deep breathing. If any information or result of examinations were in violation of the inclusion/exclusion criteria, further assessments were not performed and the patient was discontinued from the study. However, basic demographic data were always recorded.

The eligibility criteria were checked: if a patient did not fulfill the criteria they were discontinued from the trial. If the criteria were fulfilled the patient was randomized and given a unique randomization number starting with 6001. The patient was instructed about the trial medication treatment and the first dose was administered at the out-patient clinic under supervision of the study personnel. Instruction and distribution of the diary, trial medication, and other equipment were distributed.

Subsequent clinical visits, visit 1 (1.5 months±2 weeks from S/B visit), visit 2 (3 months±2 weeks from S/B visit) and visit 3 (4.5 months±2 weeks from S/B visit) and final visits, visit 4 (6 months±2 weeks from S/B visit) were scheduled, in relation to the start of study medication.

The second and fourth visits (at 1.5 and at 4.5 months from S/B visit) comprised of a nurse visit including assessment of vital signs. Used and unused clinical trial medication was returned by the patient and drug accountability was performed. The patient diary was reviewed including recording of concomitant medication, adverse events (AEs), and treatment compliance. In addition, a prior-to-dosing C-peptide sample at visit 3 was collected at site 1 (Karolinska Hospital), in 22 patients.

The third visit (at 3 months from S/B visit), comprised HbA1c and safety laboratory tests, and sampling of HLA type, C-peptide antibodies, and C-peptide levels in plasma, physical examination, and review of AEs. Used and unused clinical trial medication was returned by the patient and drug accountability was performed by the study staff. The patient diary was reviewed including recording of concomitant medication, AE, and treatment compliance.

At the final clinical visit (at 6 months from S/B visit), a safety assessment including physical examination, ECG, vital signs, body weight, and sampling for clinical safety laboratory tests were performed. Furthermore, the metabolic control (HbA1c) was assessed, as well as C-peptide antibodies and C-peptide levels in plasma. All efficacy variables including SCV, SNAP, MCV, MDL, CMAP, QST were performed (two examinations within 2-14 days). E/I ratio and neurological status were also assessed. All used and unused clinical trial medication was returned by the patient and drug accountability was performed by study staff. The patient diary was reviewed including recording of concomitant medication, AEs, and drug accountability. FIG. 1 summarizes the study procedures and assessments conducted at each time point.

A Selection of the Study Population & Inclusion Criteria

Patients fulfilling the following criteria were eligible for participation in this study: 1) given informed written consent, 2) age between 18-55 years, 3) BMI<30 kg/m$^2$, 4) duration of type 1 diabetes of more than 5 yrs, 5) normal renal function as assessed by serum creatinine below 120 µmol/L, 6) plasma or serum C-peptide<0.15 nmoL/L, 7) HbA1c<12%, 8) patients should have a diabetic distal symmetric neuropathy, according to the criteria defined at the San Antonio Conference on Diabetic Neuropathy (see below), 9) patients should have a measurable action potential (SNAP) in both sural nerves, 10) patient should have a SCV lower than 1.5 SD from body height-corrected reference value (defined as mean of both legs).

Criteria for Diabetic Neuropathy

The patients included in the study should have a diabetic distal symmetric neuropathy, according to the criteria defined at the San A"tonio Conference on Diabetic Neuropathy (American Diabetes Association et al. 1988), i.e., 2 out of 5 criteria below should be fulfilled. The respective criteria are defined as:

1. Symptoms of neuropathy, here defined as 1 point in the "Symptom assessment score".

2. Findings of neuropathy at clinical examination, here defined as 8 points in the "NIA score".

3. Findings of neurophysiological examination from at least 2 nerves, here defined as <−1.5 SD of reference values (mean of both nerves, and body height-corrected for SCV and MCV).

4. Finding on QST, here defined as >1.5 SD of reference values (mean of both legs) for at least one of the perception threshold variables for vibration, heat, and cold.

5. Pathological autonomic function test, here defined as an abnormal value (<−1.5 SD from reference value).

However, the decision had to be based on pathological findings for criteria 1, 2, or 4. Consequently, the 5$^{th}$ criterion was not included in practice.

Exclusion Criteria

Patients presenting any of the following exclusion criteria were not included in the study:

have been treated with any other investigational drug in the last 3 months before entering the study and have taken part in any other clinical trial including intervention during the duration of the study have known hypersensitivity against C-peptide, m-cresol, glycerol, or sodium phosphate have history of chronic alcohol or drug abuse within the last year or present been pregnant, breast feeding, or a women of childbearing potential not using adequate birth control (IUCD, barrier-method, oral contraceptive, abstinence)

have any medical or psychiatric condition, which could jeopardize or would compromise the patient's ability to participate in this trial or decrease the likelihood of obtaining satisfactory data to achieve the objective of the trial have neuropathy or signs of nerve dysfunction which may be a consequence of factors other than type 1 diabetes been transplanted (islet cell, kidney, or pancreas)

have had an amputation or wounds in the lower limbs that prohibit or interfere with the performance of neurological or neurophysiologic examinations have unstable glucose control in the clinical judgment of the investigator have concomitant medication such as oncolytic therapy or treatment with, e.g., steroids, tricyclic antidepressive, $Ca^{2+}$-channel blocker, antiepileptic agents, i.e., drugs that may interfere with the peripheral nerve function or measurement thereof.

Removal of Patients from Therapy or Assessments

Patients could withdraw her/his consent at any time without giving reasons and without prejudice to further treatment. A patient could also be withdrawn from the trial at any time for the following reasons at the discretion of the investigator or sponsor in the event that:

The investigator judged it necessary and in the best interest of the patient, in particular in case of a serious adverse event (SAE) or an inter-current disease.

If the patient failed to conform to the requirements of the study.

If the investigator considered the patient to be non-compliant in general and, in the opinion of the investigator, decreases the chance of obtaining satisfactory data to achieve the objective of the trial.

If a female patient became pregnant.

The patient could discontinue on the basis of an abnormal laboratory value. The investigator reviewed all abnormal values. If the abnormal value was considered to be of clinical relevance, the test was repeated and any action taken recorded.

Major protocol violations.

Inaccurate or incomplete data.

Unsafe or unethical practices.

Questionable safety of the investigational drug or as an administrative decision.

If a center did not recruit patients as planned, the sponsor could replace such a center by another center.

Patients who withdraw from the study were asked for their reason(s) for withdrawal and about the presence of any AEs. The reason(s) and date for withdrawal as well as presence of AEs were documented in the case report form (CRF).

Procedures in Case of Emergency

An envelope containing the randomization code for each patient was kept by the investigator at each site. The envelopes were returned to the trial manager un-opened after study termination. The randomization code was to be broken by opening of the sealed envelopes only in case of emergency when it was necessary to know the study medication or the batch number for the proper care of the patient, i.e., if an SAE occurred and the knowledge of the study medication was of importance for care of the patient, or required by the authorities. In case the randomization code was broken, the monitor or the trial manager had to be notified promptly either by phone or by fax, followed by a written report stating the name of the person breaking the code, the patient code, date and time, reason for breaking the code and any therapy instituted. If the code was broken due to an AE, the relationship to the study drug should be given.

B Treatments Administered

The trial medication, C-peptide, and matching placebo were supplied in 2.2 mL vials (Disetronic Pen glass vials) of identical appearance, for S.C. injection. The same treatment regimen was used for all patients, i.e., 4 daily injections concomitantly with injection of the regular insulin dose.

| Identity of investigational products | |
|---|---|
| Trial Medication 1 | |
| Name | Recombinant human C-peptide |
| Dosage form | Vials with 2.2 mL aqueous solution for subcutaneous injection |
| Strength | 3 mg/mL |
| Batch no. | 8 batches of 3 mg/mL were employed |
| Expiry date | Issued along with proven extended stability of the product in the Disetronic pen vials |
| Supplier | Creative Peptides Sweden AB |
| Trial Medication 2 | |
| Name | Recombinant human C-peptide |
| Dosage form | Vials with 2.2 mL aqueous solution for subcutaneous injection |
| Strength | 9 mg/mL |
| Batch no. | 8 batches of 9 mg/mL were employed |
| Expiry date | Issued along with proven extended stability of the product In the Disetronic pen vials |
| Supplier | Creative Peptides Sweden AB |
| Trial Medication 3 | |
| Name | Placebo |
| Dosage form | Vials with 2.2 mL aqueous solution for subcutaneous injection |
| Batch no. | 8 batches of placebo were employed |
| Expiry date | Issued along with proven extended stability of the product in the Disetronic pen vials |
| Supplier | Creative Peptides Sweden AB |

Packaging and Labeling

The investigational product was packed and labelled according to ICH GMP guidelines and to local law in such a way as to protect the products from deterioration during transport and storage. The investigational product was supplied in Disetronic Pen glass vials filled with 2.2 mL trial medication.

Storage Instructions

The trial medication was stored refrigerated (2-8° C.). Trial medication was shipped by the Sponsor to a central pharmacy (Karolinska Hospital Pharmacy), from which the investigator ordered medication when required in smaller batches. At the sites the investigators were responsible for safe and proper storage of the investigational drugs. Patients were advised to store the boxes with vials in a refrigerator as soon as possible upon receipt at the investigational site.

Procedures for Delivery and Supply

The investigational drug was shipped directly from the filling facility (Skandeborg, Denmark) to the Pharmacy of Karolinska Hospital, where labelling of boxes was performed. Initially, the investigator was supplied with trial medication for the first patients and for subsequent patients additional supplies were delivered from the hospital pharmacy on request.

Drug Accountability

The investigator was responsible for the maintenance of accurate and complete records showing the receipt and administration of investigational drug supplies. All supplies dispensed from the pharmacy during the study were accounted for throughout the study using the Drug Inventory Log which was handed over to each investigator prior to study start.

Method of Assigning Patients to Treatment Groups

At S/B visit each patient received consecutive run-in numbers starting with site no. +1001 (e.g., 21001 for the first patient at site 2). If eligible, patients were given, in consecutive order, randomization numbers starting with 6001 assigning them to start administration of one of three treatment arms of trial medication. When study medication was ordered from the central pharmacy, the pharmacist assigned an appropriate randomization number for that patient (starting with the lowest "free" study medication number in a consecutive order) and thereafter the medication was shipped to the investigational site. At arrival the ordered medication was recorded in the Drug Inventory Log. The eligible patient was given the lowest available number at the site in a consecutive order. The treatment assignment was performed using the Excel random number generator. The randomization was performed by an independent statistician.

Selection of Doses in the Study

The dose selection is based on data from previous studies, in which C-peptide has been replaced for 3 months (600 nmoL/24 h) and an effect on albumin excretion and sensory nerve conduction velocity has been observed (Johansson et al., 2000; Ekberg et al., 2003). In order to maintain adequate levels of C-peptide for as many hours of the day as possible, the daily dose was divided into four doses, injected subcutaneously using Disetronic Pen 25, and administered in the morning, at lunch, at dinner, and at bedtime. With the low dose (500 nmoL/24 h), given 4 times daily, a physiological mean plasma concentration of ~1 nmoL/L was expected, in keeping with the bioavailability of approximately 80% of subcutaneously administered C-peptide. To determine if C-peptide at a higher dose has an optimal effect, a 3 times higher dose (1,500 nmoL/24 h) was also administered.

Duration of Treatment and Site of Injection

The duration of treatment was 6 months (±2 weeks). The patients were instructed to administer the trial medication subcutaneously as 4 daily injections. The total dose of 500 nmol., 1,500 nmol., or placebo per day was divided into 4 portions ($\frac{1}{5}+\frac{1}{5}+\frac{1}{5}+\frac{2}{5}$) given in the morning (between 6:00-9:00), at lunch (11:00-14:00), at dinner (16:00-19:00) and in the evening before bed (21:00-24:00), i.e., in most cases at the same time as the patient's regular insulin injections. The patients were instructed to inject the trial medication into the abdominal wall, on the opposite side as the insulin injection.

The very first dose was given at the $2^{nd}$ S/B visit under supervision (i.e., not necessarily in connection to a regular injection of insulin). The investigator or designee instructed and demonstrated to the patient how to inject the trial medication using Disetronic Pen 25, and offered the opportunity for the patient to gain sufficient practical personal experience. Written instructions regarding storage and handling of trial medication were also provided. Study patients received study medication for ~8 weeks use at S/B visit, visit 1, visit 2, and visit 3. The content of one vial was expected to last for 2 days treatment. At clinical visits 1-4, the patient was asked to return both used and unused vials to the investigator.

Selection and Timing of Dose for Each Patient

The dose of the investigational drug was not individualized, and all patients administered the same dose in each dose arm. The timing of drug administration could vary between patients, however, for reasons of convenience the trial medication was in most cases administered at the time of the patients' regular insulin administration.

Blinding

Blinding was achieved by filling vials with C-peptide low dose, C-peptide high dose, and C-peptide diluent (placebo) solutions of identical appearance. Filling was performed by Pharma Scan, Skandeborg, Denmark, on behalf of Creative Peptides Sweden AB. All vials were labelled with a unique vial number by the Danish filler. Blinding and labelling of the boxes were performed by the Pharmacy at the Karolinska Hospital according to a computer-generated randomization schedule. Neither the investigators or the staff members, nor the patients were aware of which investigational drug was being administered during the trial.

The randomization list was kept unavailable to all persons involved in the study. The blinding was not revealed until the trial had ended and the data file was cleaned, secured, and unblinding was hence decided upon the clean file meeting. Unblinding, inadvertently or due to necessity (if, e.g., an SAE occurred and it was required by the authorities or necessary for the future treatment of a patient) could result in the patient being discontinued from the study. Whether the patient was to remain in the study or not after unblinding was to be a joint decision of the investigator and the trial manager. Any broken code should be clearly justified and explained by a comment on the CRF. However, no unblinding procedures were required during the study.

Prior and Concomitant Therapy

Patients maintained their prescribed therapy for glycemic control and recorded their insulin injections. All other treatments being taken by the patients on enrollment into the study and all treatments given in addition to the study treatment were regarded as concomitant medication.

Patients were instructed not to take any prescription medications or over-the-counter products other than those agreed upon with the investigator. Concomitant medications not permitted during the study were: $Ca^{2+}$-channel blockers, oncolytic therapy or treatment with, e.g., steroids, tricyclic antidepressive, antiepileptic agents, i.e., drugs that may have an influence on nerve function. Administration of medication for acute reasons (e.g., analgesics or antibiotics) was permitted, provided that, the dose, the frequency, and the reason were recorded by the patient in the diary, and data subsequently transferred to the CRF (trade name and/or generic name, timing, and dosage) and in the patient's medical records by the investigator. Therapy, which in the investigator's opinion became necessary during the course of the study, was not refused to the patient, but if the therapy was part of the exclusion criteria, the patient could be withdrawn from the study.

Treatment Compliance

Compliance with administration of investigational drugs was checked by visual control of returned unused and used vials and by review of patient's own recordings of drug administration in the diary. Furthermore, patients were asked about any handling problems according to predetermined questions in the CRF at visits 1, 2, 3, and 4. Compliance was considered sufficient if >80% of the intended total study dose had been administered. Patients with insufficient compliance were not included in the Per Protocol (PP) analysis of data. After completion of the study (post-data base closure), compliance was also checked by qualitative analysis of C-peptide in blood taken at visits 2 and 4.

Efficacy and Safety Variables

Demographics, underlying disease, related diseases, physical examination, and medical history.

At the S/B visit, demographics including date of birth, gender, ethnicity, body height, body weight, body mass index (BMI), and tobacco use were recoded. In addition, data on primary disease was recoded including duration of diabetes, daily insulin requirement, absence or presence of retinopathy (simplex, proliferative), nephropathy (microalbuminuria, proteinuria), and neuropathy (peripheral sensory, autonomic).

A medical history comprising relevant data on past and ongoing diseases was recorded.

Medications (insulin excluded) administered within 4 weeks prior to the S/B visit and ongoing at the time of study start were also recorded. Addition or removal of any medication was recorded throughout the study period.

Physical examinations were performed at the S/B visit, visit 2, and visit 4. ECG was performed at baseline and at end of study, i.e., visit 4 (at 6 months±2 weeks from the S/B visit).

Efficacy assessments.

Insulin Usage

Changes in insulin dosage and requirements were obtained from CRFs and based on a retrospective analysis of patient records reviewed by the investigators for information about potential changes in patients' insulin requirements.

Nerve Conduction Velocities (NCVs)

NCVs were determined twice at baseline and after 6 months of treatment (the mean of the duplicates were used for evaluation). NCV was performed with a technique that was similar to that used in the daily clinical routine with surface electrodes and digital equipment for stimulation and recording. Sensory nerve conduction velocity (SCV) and sensory nerve action potential (SNAP) amplitude bilaterally in the sural nerves, and motor nerve conduction velocity (MCV), compound muscle action potential (CMAP) and motor nerve distal latency (MDL) were determined bilaterally in the peroneal nerves in duplicate, twice at baseline, and twice after 6 months of treatment. The mean from the two legs and of the duplicates was used for efficacy (unless, in the opinion of the central reader or of the investigator there was a specific reason to disregard a result, e.g., due to poor quality of the assessment or for some other reason, e.g., an acute condition affecting only one leg). The examination was strictly standardized and performed according to instructions in the protocol and performed in a warm room, with the legs warmed with heat pads for at least 10 min prior to the nerve conduction measurements, in order to obtain skin temperatures >32° C.

The digital equipment for stimulation and recording used was sold under the trademark KEYPOINT® by Dantec Medical AIS, Skovlunde, Denmark or similar, providing a digital output from the recordings of the SNAP and the CMAP. A ground electrode was positioned on the tibial anterior aspect at the middle of the lower leg.

Motor Nerve Assessment

Stimulation. The peroneal nerve was stimulated with constant current pulses (0.10 ms duration, repetition frequency 1 Hz) through a hand-held double electrode probe pressed on the skin over the nerve with the cathode of the stimulator probe in the orthodrome direction and with both electrode disc placed over and parallel to the presumed location of the nerve. The probe had an inter-electrode distance 25 mm center-to-center, and each electrode a diameter of 7 mm. The intensity was increased by monitoring the evoked muscle response in order to establish the supramaximal level. The nerve was stimulated (1) at a fixed distance (80 mm) proximal to the muscle belly of m. extensor digitorum brevis of the foot and (2) at a position below the fibula head on the leg. At each site (1) and (2) a final single stimulus of supramaximal strength was applied and the motor response (see below) was saved for calculation. The distance between the sites (1) and (2) was measured and used in the calculation of velocity.

Motor response. The CMAP was recorded with surface electrodes (metal discs of 7 mm coated with electrode paste) placed over the muscle belly and at a site 50 mm distal to the muscle belly. The signal was recorded with a bandpass filter of 2 Hz to 10 kHz, the amplifier gain 5 mV/division (gain was increased if necessary) and sweep speed of 5 ms/division. The amplitude of CMAP was calculated from the level of the beginning of the response to its negative (upward) peak.

Motor nerve conduction. The MCV was calculated from the ratio of the distance between (1) and (2) over the latency differences between (1) and (2) of the beginning of the muscle response.

Sensory Nerve Assessment

The sural nerve was stimulated with the same stimulator and probe as above with pulses of 0.10 ms duration and a frequency 1 Hz. The site of stimulation was at the wrist on the back of the leg and the recording site was behind the lateral malleolus. Thus antidromic nerve stimulation was used, in order to obtain a larger signal due to the more superficial location of the nerve in the foot as compared to the wrist. After the recording site was established and fixed, the stimulation site was adjusted and measured to be 130 mm measured from the center of the nearest recording and stimulating electrode discs. The stimulation intensity was adjusted to the supramaximal level.

Recording. The recording probe consisted of two metal electrode discs of 7 mm with interelectrode distance 25 mm center-to-center and was placed over and parallel to the presumed location of the sural nerve. The site of the recording electrode was adjusted during repeated nerve stimulation in order to obtain the maximum response and thereafter its position was fixed with a strap around the foot. The amplifier was set to a gain of 20 µV/division, band pass filter 20 Hz to 10 kHz, and sweep speed 2 ms/division. SNAP was averaged during at least 4 (in case of low signals up to 40) stimulations given with a constant and supramaximal intensity, and the response was saved.

Sensory nerve conduction. The SCV was calculated from the ratio distance (130 mm) divided by latency from stimulus onset to the peak of SNAP (SCVp) or the start of SNAP (SCVi). The amplitude of SNAP was the peak value minus the baseline value defined by interpolation between the level at the beginning and the end of the SNAP.

Neurological Examination

The purpose of the neurological examination was to establish the current extent and severity of peripheral polyneuropathy. The examination was made according to a fixed protocol including sensory screening for touch, pin prick, vibration, heat and cold at the levels of the big toe, dorsum of the foot, and the lower leg (~10 cm below the patella), bilaterally. In addition, assessment of joint sense for the big toes and examination of reflexes were included. The observations were compiled into a score, "neuropathy impairment assessment (NIA) score". In addition, patients were asked about subjective symptoms using a symptom questionnaire.

Quantitative Sensory Testing (QST)

Thresholds of perception for heat and cold were determined using Marstock technique, twice at baseline, and after 6 months of treatment (the mean of the duplicates are used for evaluation). Taken together the QST measurements provide an evaluation of the degree of functional impairment as well as an indication of the regional distribution of the neurological impairment.

Temperature Thresholds

Temperature thresholds were assessed by equipment sold under the trademark THERMOTEST® (Somedic AB, Stockholm, Sweden) or similar. A probe with adjustable temperature was applied over the lateral dorsum of the foot and on the anterior aspect of the lower leg, ~10 cm below the patella. The temperature of the thermode was initially adjusted to 32° C. (baseline). The temperature of the thermode was automatically changed by a rate of 1° C./sec. The patients reported temperature sensations by pressing a button on perception of cold (repeated 5 times) and heat (repeated 5 times), according to the method of limits (Marstock technique). If the results were highly variable, the measurements were repeated. Measurements were done bilaterally and the mean was calculated. In case of a large variability of the threshold this was taken as a sign of abnormal sensation.

Vibration Thresholds

Vibration thresholds were assessed by a vibrameter sold under the trademark VIBRAMETER® (Somedic AB, Stockholm, Sweden) or similar. The vibrameter was applied on the skin over the first metatarsal (mid foot) and over the tibia about 10 cm below the knee. The frequency of vibration was 100 Hz and its intensity increased from 0 until the patient reports the feeling of vibration. The procedure was repeated at least three times and the mean threshold value calculated. Measurements were done bilaterally, in triplicate, and the average was calculated.

Heart Rate Variability

Autonomic nerve function was tested according to instructions in the protocol by measurement of E/I ratio during deep breathing. The deep breathing test consisted of two 70 sec periods of deep breathing with 3 min rest in between. The patient was told to inhale during 5 sec and exhale during 5 sec, i.e., 7 breathing cycles during each 70 sec period. The ratio between the longest R—R interval during expiration and the shortest R—R interval during inspiration was calculated breath by breath and the mean E/I value of 5 breaths was reported.

Evaluation of E/I ratio was not to be performed in patients who were on treatment with sympatomimetic agents or p-blockers. A renewed assessment after 6 months of treatment was only performed in those patients that presented with a pathological E/I ratio at baseline.

Laboratory Assessments

Hematology, Clinical Chemistries, and Urinalysis

The following laboratory tests were performed at the S/B visit, visit 2, and at end of study (visit 4):

Hematology: hemoglobin, hematocrit, mean cell volume, leukocytes, platelets, differential count Blood chemistry: sodium, potassium, C-reactive protein (CRP), alanine transaminase, aspartate transaminase, serum creatinine, albumin Urinanalysis: protein, blood, nitrite Other Tests:

The following laboratory tests were performed at the S/B visit, visit 2, and at end of study (visit 4):

HbA1c (metabolic control) and in women a urine sample for determination of HCG (human chorion gonadotropine)

C-peptide in plasma

C-peptide antibodies

HLA typing (only at visit 2)

Markers for Atherosclerosis

The total amount of blood drawn during the study did exceed 100 mL per patient.

Labelling and Handling of Samples

Laboratory tests for hematology, clinical chemistries, urine analysis, HbA1c, and HCG, as well as C-peptide plasma levels for screening (inclusion criteria) were analyzed at each site's local Department of Clinical Chemistry according to their standard operating procedures.

C-peptide plasma samples, C-peptide antibodies, and markers for atherosclerosis were processed (centrifuged, etc.) and stored frozen until transport to a central lab. HLA typing samples were shipped to a central lab for processing and storage until analysis. All samples there were labelled uniquely, including information about screening number and sample time.

Safety Measurements

The safety measurements comprised collection of AEs, spontaneously reported by the patient or recorded by the investigator at each clinical visit. Review of laboratory investigations, vital signs, and physical examinations was performed at the S/B visit, visit 2, and at end of study (visit 4). ECG was performed at the S/B visit and at visit 4.

Adverse Events

An AE was classified as "unexpected event" (i.e., if not specifically listed in the Investigator's Brochure) in terms of nature, severity, or frequency. All AEs, including intercurrent illnesses and increased severity or frequency of sign/symptoms of a concomitant disease was reported and documented as described below. AEs were documented on an "Adverse Event/Serious Adverse Event" page of the CRF and in the patient's medical records. Any AE occurring at any time after the end of the study, considered to be caused by the study medication—and therefore a possible adverse drug reaction—was reported to the sponsor.

The following observations were also to be considered as AEs:

Laboratory value(s) out of reference range and of clinical concern

Laboratory value(s) changed from patient's baseline value and considered of clinical concern Pre-existing physical findings which worsened compared to baseline and which believed to be clinically significant Physical findings (including vital sign) observed during the trial and which believed to be clinically significant.

Hypoglycemic events are common events in insulin-treated patients. For practical reasons only severe hypoglycemic events, i.e., if the patient required assistance from another person in order to regain normoglycaemia, were reported as an AE.

The investigators were asked to follow up all unresolved AEs during 30 days after treatment termination or until a stable status was achieved. This follow-up information was collected in the AE form.

Non-Immediate Reporting of All AEs

All non-serious AEs were recorded on the AE form in the CRF. The AE information was collected on a regular basis during the clinical trial by the trial manager and transferred to the Sponsor.

Immediate Reporting of SAEs

Regardless of severity all serious adverse events (SAEs) which occurred during the duration of the study were reported within 24 hours by telephone or telefax to the Clinical Project Manager or Drug Safety Officer of the Sponsor and in writing within 5 days. As far as possible, all points on the "Adverse Event/Serious Adverse Event" page of the CRF were covered in the initial telephone report or the completed form. The form was then sent by mail to responsible staff of Creative Peptides. After receipt of the initial report, the responsible staff reviewed the information and contacted the investigator, if necessary, to obtain further information for assessment of the event. When required, a follow-up report including all new information obtained on the serious adverse event was prepared and sent to Clinical Project Manager or Drug Safety Officer of the Sponsor. The report was marked "Follow-up report". Copies of all SAEs reported during the study were submitted to the authorities.

Assessment of Laboratory Values

Coagulation, Hematology, Clinical Chemistry

Before starting the study, the investigator supplied the Sponsor with a list of the normal laboratory ranges and units of measurement for the laboratory variables to be determined during the study at the site. All abnormal laboratory (those out of the normal range) values required comments on the CRF, regardless of the clinical significance:

Error—Include improper sample preparation, hemolysis, delayed transit to laboratory, etc.

Not relevant—Abnormality that was not alarming.

Patient condition—Abnormality that was a consequence of the patient's disease, age, etc.

Adverse event—Clinically relevant abnormal value that cannot be explained by the above assessment flags. Adverse Event/Serious Adverse Event CRF was filled in.

Assessment of Adverse Events

The period of observation for AEs extended from the time the patient started on trial medication until end of the study. AEs were divided into the categories "serious" and "non-serious". This determined the procedure used to report/document the AE. An SAE is any untoward medical occurrence that:

results in death, is life-threatening, requires hospitalization or prolongation of existing hospitalization, results in persistent or significant disability/incapacity, is a congenital anomaly/birth defect other "important medical events".

"Important medical events" that may not result in death, be life-threatening, or require hospitalization may be considered a SAE when, based upon appropriate medical judgment, they may jeopardize the patient and may require medical or surgical intervention to prevent one of the outcomes listed in the definition. Examples of such medical events include allergic bronchospasms requiring intensive treatment in an emergency room or at home, blood dyscrasias, or convulsions that do not result in hospitalization, or the development of drug dependency or drug abuse.

"Life-threatening" means that the patient is at immediate risk of death from the event as it occurred. It does not include an event that, had it occurred in a more severe form, might have caused death. "Requires hospitalization or prolongation of existing hospitalization" should be defined as hospital admission/prolongation required for treatment of the AE. Hospital admission for scheduled elective surgery would not be an SAE. "Disability" means a substantial disruption of a person's ability to conduct normal life functions.

AEs, which do not fall into these categories, are defined as non-serious. It should be noted that a severe AE need not be serious in nature and that a serious AE need not, by definition, be severe.

Regardless of the classification of an AE as serious or non-serious (see above), its severity was assessed as mild, moderate, or severe, according to medical criteria alone:

| | |
|---|---|
| mild = | does not interfere with routine activities |
| moderate = | interferes with routine activities |
| severe = | impossible to perform routine activities |

Patient was instructed by the investigator to report the occurrence of any AE. All AEs, regardless of severity, were followed up by the investigator until satisfactory resolution. All patients experiencing AEs—whether considered associated (means associated if reasonable possibility that the event may have been caused by the drug) with the use of the study medication or not—was monitored until symptoms subside and any abnormal laboratory values had returned to baseline, or until there was a satisfactory explanation for the changes observed, or until death, in which case a full pathologist's report was supplied, if possible. All findings were reported on an "Adverse event" page in the CRF and in the patient's medical records.

Withdrawal from the clinical study and therapeutic measures was done at the discretion of the investigator. A full explanation for the discontinuation from the clinical study was made on the appropriate CRF.

The sponsor provided all investigators involved in a clinical investigation with information regarding clinically relevant AEs.

Primary Endpoints

The primary efficacy variable was the nerve conduction velocity in the sural nerve (SCV) and more specifically, the change of conduction velocity from baseline to 6 months (visit 4). The assessment of SCV was determined bilaterally twice at the S/B visit and at visit 4 and the mean of the 4 recordings, respectively, was used for evaluation of efficacy. The measurement of SCV was strictly standardized.

Drug Concentrations Measurements

Blood samples for determination of C-peptide in plasma were drawn at the S/B visit, visit 2, and at end of study (visit 4). The baseline assessments primarily aimed at demonstrating the extent of C-peptide deficiency in the study population.

The sampling of C-peptide in plasma at visits 2 and 4 coincided with the clinical visit and the time between the most recent administration of the trial drug and sampling varied between patients. Thereby, the result of C-peptide concentrations in plasma was less suitable for pharmacokinetic evaluations, but the results contributed to the assessment of treatment compliance.

Data Quality Assurance

A site visit was performed by the trial manager and the monitor prior to the start of the trial, to review the protocol in detail with the investigator and to assure the availability of appropriate study personnel and their ability to properly conduct the study according to Good Clinical Practice (GCP) procedures.

The study site was visited periodically during the study by the monitor to check the clinical facilities and that the investigational team adhered to the study protocol and that the results of the study were recorded accurately in the CRFs. An audit was performed at one site (Uppsala University Hospital) and at the central pharmacy (Karolinska Hospital) during the study. No major violations were found at the audits. During monitoring visits, reported data were reviewed with regard to accuracy and completeness and data were verified against source documents (e.g., patient files, ECG recordings, laboratory notes, etc.). All data reported in the CRF were supported by source documents unless otherwise stated by the source data verification list.

Data Management

The Case Report Forms (CRF) were monitored and edited by the investigator. CRF data was subsequently transferred to a database and accuracy checked by double-entry of data. The data were sent electronically as a Microsoft Excel file to the data manager/statistician, as well as to an additional statistician. The data manger/statistician then transferred the data to a SAS database and performed statistical calculation according to a predetermined statistical analyses plan. The second statistician transferred the data into a SPSS program, performed calculations, and the results of these were confirmed to be identical to the results of the first statistician. All primary and secondary variables in the SAS database were proofread checked against the data in the CRF. After cleaning the file, all data was transferred to a CD-ROM (read-only-memory).

Statistical Analysis of Primary and Secondary Variables

Descriptive statistics were performed on all variables collected. Analyses were performed on an intent-to-treat (ITT) and a per-protocol (PP) basis. The primary efficacy variable was change from baseline to 6 months of treatment for SCV and comparisons of changes between the treatment groups. Non-parametrical statistical tests (Wilcoxon type) were used. Mean, standard deviation, median, and ranges are presented herein. An improvement of the patient's glycemic control (HbA1c) was expected in all treatment groups and this change was evaluated. Exploratory multivariate analyses including possible predictors of the dependent variables was performed on the primary efficacy variable (change baseline to 6 months) using HbA1c as one of the predictors.

Statistical Analysis of Safety Variables and Adverse Events

Descriptive statistics were used for safety variables. For lab parameters summary statistics were presented as change from baseline and between doses. The changes from baseline were calculated and compared with normal ranges. The safety analysis set included all patients who obtained at least one dose of the investigational drug. AEs were coded according to the MedDRA dictionary. The frequencies of AEs are tabulated by body system and included/preferred term.

Determination of Sample Size

The power analyses of this study was based on the experience from the 3 months treatment study on sub-clinical diabetic neuropathy, where SCV was improved by 2.7 m/s in the C-peptide treated group and the common SD for the two groups (active and placebo) was 4.07 m/s. The following estimates were done:

Primary Analysis, Comparison Between Placebo and Active Treatment

A two group t-test with a 0.050 two-sided significance level will have 80% power to detect the difference in change (baseline to 6 months) between a Group 1 (placebo) mean, $\mu_1$, of 0 m/s and a Group 2 (active drug: high+low dose) mean, $\mu_2$, of 2.7 m/s, a difference in means of −2.7 m/s, assuming that the common standard deviation is 4.07 m/s, when the sample sizes in the two groups are 28 and 56, respectively (total sample size 84).

Secondary Analysis, Differences Between Low and High Dose

A two group t-test with a 0.050 two-sided significance level will have 80% power to detect the difference in change (baseline to 6 months) between a Group 1 (low dose) mean, $\mu_1$, of 2.7 m/s and a Group 2 (high dose) mean, $\mu_2$, of 5.0 m/s, a difference in means of −2.3 m/s, assuming that the common standard deviation is 4.07 m/s, when the sample sizes in the two groups are 51 and 51, respectively (total sample size 102).

Secondary Analysis Test of Equivalence of Effects of High and Low Dose

When the sample size in each group is 40, a two group 0.05 one-sided t-test will have 80% power to reject the null hypothesis that the effects of high and low doses are not equivalent (the difference in means, $\mu_H - \mu_L$, is 2.3 m/s or further from zero in the same direction) in favor of the alternative hypothesis that the means of the two groups are equivalent, assuming that the expected difference in means is 0.0 and the common standard deviation is 4.07 m/s.

In accordance with the above calculations the intention was to include 50 evaluable patients per group, i.e., a total of 150 evaluable patients.

II Study Patients

Disposition of Patients

Patients were recruited to the study by advertisements and by screening of hospital records of patients with type 1 diabetes. All patients reporting interest for participation in the study were screened for eligibility. One-hundred-sixty-one (161) patients met the inclusion criteria. All these patients were found eligible and were randomized to the investigational drugs, 56 patients to low-dose C-peptide, 52 patients to high-dose C-peptide, and 53 patients to placebo. Additionally, one patient was randomized but found not to be C-peptide negative and, consequently, did not start the treatment (Table E1, FIG. 2).

Screening Deviations

Among the randomized patients (n=162) the following were included in the study in spite of minor violations to the inclusion/exclusion criteria, Table E1.

TABLE E1

Screening deviations

| Low-dose C-peptide Reason | High-dose C-peptide Reason | Placebo Reason |
|---|---|---|
| Not applicable | Pregnant at screening/baseline visit - not noticed by site staff; withdrawn from the study immediately when apparent (at visit 1) Suspected alcohol abuse, but denied by patient. Confirmed when patient had completed the study. | The baseline C-peptide was above acceptance limit for participation - patient never started the treatment |

Minor Protocol Deviations, Patients Included in the Per Protocol (PP) Analyses

The following patients were included in the PP analysis in spite of minor protocol violations during the study, Table E2.

TABLE E2

Minor protocol deviations

| Low-dose C-peptide Reason | High-dose C-peptide Reason | Placebo Reason |
|---|---|---|
| C-peptide sample result at V2 viewed by monitor by mistake | C-peptide sample result at V2 viewed by investigator and study nurse by mistake (not seen by neurologist or neurophysiologists) | C-peptide sample result at V2 viewed by investigator and study nurse by mistake (not seen by neurologist or neurophysiologists) |
| Suspected activation of multiple sclerosis, but without symptoms at S/B and V4 | C-peptide sample result at V2 viewed by investigator and study nurse by mistake (not seen by neurologist or neurophysiologists) | Concomitant medication: low dose lithium during study |
| Patient has HIV, disease status and concomitant medication unlikely to affect nerve function | Vitamin $B_{12}$ deficiency - oral replacement started, disease status or concomitant medication unlikely to affect nerve function | |
| Patient has rheumatoid arthritis, diagnosed 2000, and due to short duration this is unlikely to affect nerve function | Concomitant medication: low dose felodipine started during study | |
| NCV measured at a skin temperature <32° C. NCV measured at a skin temperature <32° C. | Concomitant medication: felodipine ongoing at S/B, stopped after 2 months | |

S/B = screening/baseline; V2 = visit 2; V4 = visit 4

Other Minor Protocol Violations:

time between visits, was shorter or longer than stated in the protocol (45 patients)

inappropriate use of the study medication; vials used >2 days and/or doses were combined (60 patients)

had medical conditions and/or concomitant medication that potentially might influence nerve function (23 patients)

Minor Protocol Deviations, Patients Excluded from the PP Analyses

For the following protocol deviations, decisions were taken that variables should be excluded from PP analyses, Table E3.

TABLE E3

Minor protocol deviations excluded from the PP analyses

| Minor protocol deviations excluded from the PP analyses | Treatment | | | |
|---|---|---|---|---|
| | Low-dose C-peptide | High-dose C-peptide | Placebo | Decision |
| E/I ratio measured despite patient taking β-blocker or sympaticomimetic drugs | 6 patients | 4 patients | 5 patients | E/I data from these patients will not be evaluated |
| S/B sex questionnaire filled in after treatment start | | | 1 patient | Sex Quest data from this patient will be excluded from the PP analysis |

TABLE E3-continued

Minor protocol deviations excluded from the PP analyses

| Minor protocol deviations excluded from the PP analyses | Treatment | | | Decision |
|---|---|---|---|---|
| | Low-dose C-peptide | High-dose C-peptide | Placebo | |
| Treatment started prior to S/B2 measurement of NCV and QST | 1 patient | | | SB2 data from this patient will be excluded in the PP analyses |
| NIA performed after treatment stop | | 1 patient | 1 patient | NIA data from these patients will be excluded from the PP analysis |
| Treatment stopped prior to measurement of NCV and QST at V4:2 | 1 patient | | | V4:2 data from this patient will be excluded from the PP analyses |

Major Protocol Deviations

Three patients in the high-dose C-peptide group, one patient in the low-dose C-peptide group, and one patient in the placebo group had major protocol deviations and were excluded from the PP analysis of efficacy, Table E4.

TABLE E4

| Major protocol deviations | | |
|---|---|---|
| Low-dose C-peptide Reason | High-dose C-peptide Reason | Placebo Reason |
| Unsuccessful compliance based on review of patient diary, only ~65% of study medication was taken during the study | Shortened treatment period (4 months) due to summer vacation | Medical condition, patient had hypothyreosis, onset between visits 2 and 3, which could influence nerve function |
| | Suspected alcohol abuse, but denied by patient. Confirmed later, when completed the study. Unsuccessful compliance based on review of patient diary, only ~54% of study medication was taken during the study | |

Patient Discontinuations

Fifteen (15) patients withdrew their consent to participate in the study, and two patients were withdrawn from the study, Table E5.

TABLE E5

| Patient discontinuations | | |
|---|---|---|
| Low-dose C-peptide Reason | High-dose C-peptide Reason | Placebo Reason |
| Depression worsened, pain hand/feet, hyperglycemia and worsening of sight problem (WC) | Injection needle too rough (WC) | Too busy, unwilling to continue (WC) |
| Too big burden of work (WC) | Pregnancy (screening failure) | Increased appetite and unstable blood glucose (WC) |
| | Family reasons (WC) | Pain and haematoma at injections (WC) |
| | Too many injections (WC) | Failed to keep appointments, did not manage the study (WC) |
| | Failed to keep appointments on several occasions (WC) | Family problems (WC) |
| | Too busy (WC) | |
| | Patient frightened for worsening of her retinopathy (WC) | |
| | Relapse of rheumatoid arthritis (AE) | |
| | Patient in police custody (AE) | |
| | Increased incidence of hypoglycemic events (WC) | |

WC = patients withdrawn consent; AE = adverse event

III Efficacy Evaluation

Data Sets Analyzed

Two data sets were created based on patient evaluability, the Intent-To-Treat (ITT) and Per-Protocol (PP) data sets. The ITT data set comprises all 161 patients who attended the first clinical screening visit (excluded is the one patient who was randomized but never started study medication).

The PP data set is a subset of the ITT data set excluding patients with major protocol deviations as defined in the study protocol or other major protocol violation not foreseen in the study protocol. With respect to the PP data set, the patient evaluability was decided upon before declaring clean file and breaking the treatment code.

The evaluation of the primary and secondary efficacy variables were based on the PP data set whereas the evaluation of safety data was based on the ITT data set. Missing values were handled according to the last-value-carried-forward (ITT LVCF) technique.

In addition, a third data set comprising those patients in the PP data set with a SCVp at screening/baseline better than −2.5 SD, henceforth referred to as "SCVp>−2.5 at SB".

Demographics and Other Baseline Characteristics

The demographics and key characteristics of the study patients are summarized in Table E6. All treatment groups were well matched with no statistically significant differences between the groups with respect to the demographic variables.

TABLE E6

Demographics and key characteristics of the study population
(ITT data set) (n = 161)

| | Low-dose C-peptide | | High-Dose C-peptide | | Placebo | |
|---|---|---|---|---|---|---|
| | Mean ± SD | Median (min; max) | Mean ± SD | Median (min; max) | Mean ± SD | Median (min; max) |
| Age (years) | 44 ± 7.3 | 44 (29; 55) | 43.5 ± 7.2 | 44.5 (25; 55) | 42.5 ± 7.6 | 43 (22; 54) |
| Gender female/male | 20/36 | | 22/30 | | 29/24 | |
| Body weight (kg) | 78 ± 12.8 | 76.3 (54; 110) | 73.8 ± 12.1 | 73 (51; 102) | 74.3 ± 10.7 | 73 (59; 105) |
| Height (cm) | 176.6 ± 10.8 | 177 (156; 205) | 172.6 ± 8.2 | 172.5 (148; 190) | 172.4 ± 9.7 | 173 (148; 200) |
| BMI (kg/m+hu 2+l ) | 24.9 ± 2.8 | 24.6 (19.2; 29.7) | 24.7 ± 3.1 | 24.0 (17.6; 30.0) | 24.9 ± 2.5 | 24.6 (20.6; 30.0) |
| Diabetes duration (yrs) | 31 ± 8.8 | 31.5 (6; 48) | 28.2 ± 11.1 | 27 (11; 51) | 28.7 ± 9.3 | 29 (10; 48) |
| Age at diabetes onset (yrs) | 13.8 ± 8.1 | 12.5(3; 45) | 16.1 ± 11 | 13 (0; 38) | 14.6 ± 8.7 | 13 (3; 32) |
| Insulin dose (IUkg/24 h) | 0.64 ± 0.14 | 0.63 (0.41; 0.98) | 0.69 ± 0.21 | 0.65 (0.38; 1.51) | 0.63 ± 0.18 | 0.62 (0.28; 1.14) |
| HbA1c (%) | 7.57 ± 1.19 | 7.45 (4.6; 10.2) | 7.60 ± 1.31 | 7.55 (5.1; 11) | 7.91 ± 1.36 | 7.90 (4.9; 10.9) |
| C-peptide at screening (nmoL/L) | 0.01 ± 0.03 | 0.00 (0; 0.16) | 0.03 ± 0.04 | 0.00 (0; 0.20) | 0.01 ± 0.01 | 0.00 (0; 0.07) |
| Disposition of patients | | | | | | |
| Safety ITT (n) | 56 | | 52 | | 53 | |
| Efficacy PP (n) | 53 | | 39 | | 47 | |

Characteristics of the Primary Disease

Baseline data on the primary disease are given in Table E7. The diabetes duration was on the order of 30 years in all groups, ranging from 11-51 years in the high-dose C-peptide group, 6-48 years in the low-dose C-peptide group, and 10-48 years in the placebo group. The daily insulin requirements, level of metabolic control (HbA1c), and fasting blood glucose level were similar in all three groups.

TABLE E7

Baseline data for the PP population with
"SCVp >−2.5 SD at baseline"

| | Low-dose C-peptide n = 31 | | High-dose C-peptide n = 18 | | Placebo n = 21 | |
|---|---|---|---|---|---|---|
| | Mean ± SD | Median (min; max) | Mean ± SD | Median (min; max) | Mean ± SD | Median (min; max) |
| Age (years) | 44 ± 7.6 | 44 (33; 55) | 45 ± 5.8 | 46 (35; 54) | 43 ± 5.9 | 42 (31; 54) |
| Gender female/male | 21/19 | | 11/7 | | 11/10 | |
| Body weight (kg) | 78 ± 14.1 | 78 (54; 110) | 71 ± 12.6 | 72 (51; 95) | 75 ± 12.2 | 73 (60; 105) |
| Height (cm) | 177 ± 11.7 | 178 (159; 205) | 169 ± 9.9 | 168 (148; 190) | 173 ± 8.7 | 174 (163; 200) |
| BMI (kg/m$^2$) | 24.5 ± 2.8 | 23.8 (20.1; 29.7) | 24.9 ± 2.9 | 24.6 (20.7; 29.9) | 25.0 ± 2.6 | 24.3 (21.9; 30.0) |
| Diabetes duration (yrs) | 31 ± 9.5 | 31 (9; 48) | 32 ± 12.8 | 29 (12; 51) | 27 ± 7.3 | 26 (14; 43) |
| Age at diabetes onset (yrs) | 14 ± 8.8 | 13 (3; 45) | 13 ± 11.4 | 12 (0; 38) | 16 ± 9.1 | 16 (3; 32) |
| Insulin dose (IU/kg/24 h) | 0.62 ± 0.16 | 0.59 (0.41; 0.98) | 0.64 ± 0.14 | 0.62 (0.38; 0.98) | 0.61 ± 0.13 | 0.62 (0.36; 0.78) |
| HbA1c (%) | 7.33 ± 1.13 | 7.40 (4.6; 9.6) | 7.54 ± 0.99 | 7.50 (6.1; 9.1) | 7.60 ± 1.48 | 7.60 (4.9; 10.5) |
| C-peptide at screening (nmoL/L) | 0.01 ± 0.02 | 0.00 (0; 0.10) | 0.03 ± 0.03 | 0.01 (0; 0.09) | 0.01 ± 0.01 | 0.00 (0; 0.05) |

The following number of patients administered their insulin by infusion pump, whereas the remaining patients all used S.C. injections:
- Low-dose C-peptide group; n=14
- High-dose C-peptide group; n=8
- Placebo group; n=16

Conditions related to the primary disease of the study patients (peripheral and autonomic neuropathy, retinopathy, nephropathy) reported at the S/B visit are presented in Table E8.

TABLE E8

Diabetes complications (peripheral and autonomic neuropathy, retinopathy, nephropathy) known at baseline (ITT data set, n = 161)

|  | Low-dose C-peptide n = 56 N (%) | High-dose C-peptide n = 52 N (%) | Placebo n = 53 N (%) |
|---|---|---|---|
| No neuropathy | 25 (44.6%) | 21 (40.4%) | 27 (50.9%) |
| Peripheral neuropathy | 21 (37.5%) | 24 (46.2%) | 19 (35.8%) |
| Autonomic neuropathy | 2 (3.6%) | 2 (3.8%) | 1 (1.9%) |
| Both peripheral and autonomic neuropathy | 8 (14.3%) | 5 (9.6%) | 6 (11.3%) |
| No retinopathy | 6 (10.7%) | 10 (19.2%) | 8 (15.1%) |

TABLE E8-continued

Diabetes complications (peripheral and autonomic neuropathy, retinopathy, nephropathy) known at baseline (ITT data set, n = 161)

|  | Low-dose C-peptide n = 56 N (%) | High-dose C-peptide n = 52 N (%) | Placebo n = 53 N (%) |
|---|---|---|---|
| Simplex retinopathy | 32 (57.1%) | 20 (38.5%) | 19 (35.8%) |
| Proliferative retinopathy | 18 (32.1%) | 22 (42.3%) | 25 (47.2%) |
| No nephropathy | 48 (85.7%) | 45 (86.5%) | 43 (81.1%) |
| Microalbuminuria | 7 (12.5%) | 7 (13.5%) | 7 (13.2%) |
| Proteinuria | 1 (1.8%) | 0 | 2 (3.8%) |

Medical History

At the start of the study, 53 patients (95%) in the low-dose C-peptide group, 51 patients (98%) in the high-dose C-peptide group, and 50 patients (94%) in the placebo group had other ongoing diseases or medical conditions besides the primary and primary-related diseases, Table E9. Numbers in brackets in the table refer to number of patients in each category. Since a single patient may have several different medical conditions, the total number of occurrences do not equal the total number of patients in each treatment group.

TABLE E9

Ongoing diseases or medical conditions, except primary disease at study start (ITT data set). Number in parentheses equals number of patients per diagnosis.

| Organ system | Low-dose C-peptide n = 56 Specifications | High-dose C-peptide n = 52 Specifications | Placebo n = 53 Specifications | Total |
|---|---|---|---|---|
| Metabolic-Endocrine | Hyperlipidemia (7) Hypothyreos (3) Severe hypoglycemia with unconsciousness (1) | Benign thyroid tumor (1) Hyperlipidemia (3) Hyperthyreos (1) Hypothyreos (5) | Cystic changes in breast (1) Hypothyreos (4) Hyperlipidemia (3) | 29 |
| Cardio vascular | Hyperlipidemia (3) Hypertension (14) Varicose veins (1) | Angina pectoris (1) Heartbeat palpitaion episodes (1) Hyperlipidemia (1) Hypertension (13) | Hyperlipidemia (6) Hypertension (10) | 50 |
| Pulmonary |  | Asthma bronchiale (6) | Bronchial constriction (1) Unspecific coughing (1) Asthma bronchiale (2) | 10 |
| Hepato-Gastro intestinal | Constipation (2) Diarrhea (1) Gastritis (3) Lactose intolerance (1) Primary biliary cirrhosis (1) | Celiachi (1) Colon irritable (1) Diffuse gastric and bowel symptom (1) Gastritis (4) Gluten and lactose intolerance (1) Small tumor below umbilicus (1) Nausea, vomiting (1) Ulcerative colitis (1) Diarrhea intermittent (1) | Chronic bowel inflammation (1) Gastritis/Duodenitis (3) Gastropares/gastrointestinal pain/constipation (5) Unspecific dyspepsia (1) | 30 |
| Renal/Genito Urological | Genital Mucosis (1) Impotence (2) Microalbuminuria (1) Recurrent urinary tract infection (1) Ovarian cyst (1) Incontinence problem (1) | Erectile dysfunction (1) Myoma uteri (1) | Albuminuria (1) Erectile dysfunction (1) Endometriosis (1) Menorraghia (1) | 13 |

TABLE E9-continued

Ongoing diseases or medical conditions, except primary disease at study start (ITT data set). Number in parentheses equals number of patients per diagnosis.

| Organ system | Low-dose C-peptide n = 56 Specifications | High-dose C-peptide n = 52 Specifications | Placebo n = 53 Specifications | Total |
|---|---|---|---|---|
| Haematological/ Lymphatic | HIV (1) | Anaemia or $B_{12}$ deficiency (3) Thrombocytosis (1) | Mild chronic lymphatic leukemia (1) PAI-1 deficiency (1) | 7 |
| Dermatological | Acne (1) Dermatomycosis (1) Dura molle (1) Eczema (7) Granuloma annuale (2) Psoriasis (1) Vitiligo (1) | Dry skin (2) Eczema (1) Granuloma anulare (1) Lichea planus (1) Psoriasis (2) Vitiligo (2) | Acne (2) Carbunculosis (1) Diabetic dermopathy (1) Herpes Infection (2) Eczema (2) Herpes zoster (1) | 32 |
| Allergies | Allergic rhinitis (2) Allergy (Birch, mold, furs, nickel, cat, dogs, penicillin, pollen) (11) Rhinoconjunctivitis (2) | Allergic asthma (1) Allergic rhinitis (4) Allergy (cats, dogs, penicillin, pollen) (10) Stress urticaria (1) Urticaria against food (1) | Allergy (cats, dogs, penicillin, foods, pollen) (13) Rhinoconjunctivitis (2) Anxiety, insomnia (1) | 48 |
| Musculo Skeletal Fibromyalgia (1) | Carpal tunnel syndrome (4) Carpal tunnel syndrome (1) Frozen shoulder (4) Head/back/shoulder/ neck/leg and/or muscle pain (4) Hip-joint arthritis (1) Arthritis dig I (1) Omarthritis (1) Headache now and then (1) Rheumatoid arthritis (1) Spontaneous metatarsal fractures (1) Shoulder/hip stiffness (2) Trigger op (1) Duputrytren's tcontracture (1) Atralgi, general all joints (1) Arthritis shoulder (1) Whiplash (1) Artrophati (Arthros) hands (1) Osteochondrit op.knee past (1) Epicondylitis elbow (1) Heel spur (1) Head trauma with epidural bleeding (not operated) (1) | Arthritis (2) Carpal tunnel Dig I left nail Frozen shoulder (3) Neck and shoulder stiffness/pain (4) Omarthritis (1) Osteopathi (1) Osteoporosis (1) Whiplash (1) | Bursitis left knee (1) Shoulder pain (2) crushed (1) Left thumb sprained (1) Carpal tunnel syndrome (10) Whiplash (1) Costal and clavicular fracture (1) Fibromyalgia (1) Frozen shoulder (2) Knee injury - arthrosis (2) Inguinal hernia (1) Omarthritis (1) Pain knee/shoulder/neck (3) Knee injury (1) Shoulder/hip/back stiffness (4) Shoulder tendinitis (3) Finger tendoclevage - multiple (1) Fractures; os naviculare/tibia/ fibula (2) Osteoporosis (1) Duputrytrens contracture (1) Neckproblem from arachnoidal cystic changes (1) | 87 |
| Neurological | Headache/Migraine (8) Mild numbness in hand (1) Paraesthesias legs (1) Autonomic neuropathy (1) Unspecific symptoms from feet (1) | Erectile dysfunction (1) Headache/Migraine now and then (4) Paraesthesias hand (1) Vertebra compression C5-C6 (1) Whiplash (1) Facialis paresis (1) Meniere (1) | Erectile dysfunction (1) Headache (2) Mild burning felling in feet (1) Mild sensation feeling toe (1) Tension headache (1) Vertigo-unclear (1) | 28 |
| Sense Organs | Blindness (2) Decreased vision (1) Reduced hearing (2) | Blind right eye (1) Glaucoma (2) Reduced/Hearing loss (3) | Cataract (2) Impaired hearing (2) Impaired vision (1) | 24 |

TABLE E9-continued

Ongoing diseases or medical conditions, except primary disease at study start (ITT data set). Number in parentheses equals number of patients per diagnosis.

| Organ system | Low-dose C-peptide n = 56 Specifications | High-dose C-peptide n = 52 Specifications | Placebo n = 53 Specifications | Total |
|---|---|---|---|---|
| Other | Cataract (1) Lipoma (1) Sjogrens syndrome (1) | Recurrent vax plug (1) Tinnitus (1) Vasomotoric rhinitis (1) Dystrophia lateral cornea bilat. (1) Dyslexia (1) Episodes of dizziness and tachycardia (1) Weight increase since years (1) | Mb Meniere (1) Enucleated eye dex (1) Vitreus and retinal eye op (1) Adenoma breast (1) Insomnia (1) Snoring - sleep apnea (1) | 8 |
| Total | 124 | 112 | 130 | 366 |

Concurrent Medication

The medications taken at study start and during the study are shown in Table E10.

TABLE E10

Medications taken within 4 weeks of study start and medications taken during the study (ITT data set). The Anatomical Therapeutic Chemical (ATC) Classification System is used for the classification of the drugs.

| ATC Classification System, Anatomical groups | ATC Classification System, Therapeutic main groups | Low-dose C-peptide n = 56 | High-dose C-peptide n = 52 | Placebo n = 53 |
|---|---|---|---|---|
| A. Alimentary tract and metabolism | Drugs for acid-related disorders | 7 | 3 | 10 |
| | Drugs for functional gastrointestinal disorder | 1 | 1 | 1 |
| | Bile and liver therapy | 1 | | |
| | Laxatives | 1 | 1 | 3 |
| | Antidiarrheals intestinal anti-inflammatory/anti-infective agents | 2 | 4 | 3 |
| | Antiobesity preparation | 1 | | |
| | Drugs used in diabetes | 2 | | |
| | Vitamins | 5 | 1 | |
| | Mineral supplements | 1 | 3 | 1 |
| B. Blood and blood forming organs | Antithrombotic agents | 5 | 12 | 10 |
| | Antihemorrhagics | 1 | 1 | |
| | Antianemic preparations | 7 | 2 | |
| | Parenteral carbohydrate solution | 1 | 3 | |
| C. Cardio vascular system | Vasodilators used in cardiac | 2 | | |
| | Diuretics | 11 | 5 | |
| | Beta-blocking agents | 7 | 5 | 6 |
| | Calcium channel blockers | 2 | 2 | |
| | Agents acting on renin-angio-tensin system | 19 | 16 | 16 |
| | Serum lipid-reducing agents | 17 | 12 | 13 |
| D. Dermatologicals | Antifungals for dermatological use | 1 | 1 | |
| | Dermatological emollients and protectives | 1 | 1 | 1 |
| | Antipsoriatics | 2 | | |
| | Antibiotics and chemotherapeutics for dermatological use | 3 | 1 | |
| | Corticosteroids, dermatological preparations | 1 | 5 | 1 |
| | Anti-acne preparations | 1 | | |
| | Other dermatological preparation | 1 | | |
| G. Genito-urinary system and sex hormones | Gynecological anti-infectives and antiseptics | 1 | 1 | |
| | Sex hormones and modulators of the genital systems | 3 | 6 | 7 |
| | Drugs used in erectile dysfunction | 6 | 3 | 3 |
| H. Systemic hormonal | Corticosteroids for systemic use | 1 | 2 | 3 |
| | Thyroid hormones | 3 | 9 | 8 |
| | Glycogenolytic hormones | 3 | 1 | 1 |

TABLE E10-continued

Medications taken within 4 weeks of study start and medications taken during the study (ITT data set). The Anatomical Therapeutic Chemical (ATC) Classification System is used for the classification of the drugs.

| ATC Classification System, Anatomical groups | ATC Classification System, Therapeutic main groups | Low-dose C-peptide n = 56 | High-dose C-peptide n = 52 | Placebo n = 53 |
|---|---|---|---|---|
| preparations, excluding sex hormones and insulins | | | | |
| J. Anti-infectives for systemic use | Antibacterials for systemic use | 16 | 18 | 17 |
| | Antimycotics for systemic use | 2 | | |
| | Antivirals for systemic use | 5 | 1 | |
| | Vaccines | 1 | | 3 |
| L. Antineoplastic and immunomodulating agents | Hormone antagonists and related agents | 2 | | |
| M. Musculoskeletal system | Anti-inflammatory and antirheumatic products, non-steroids | 42 | 23 | 51 |
| | Topical products for joint and muscular pain | | 1 | |
| | Drugs affecting bone structure and mineralization | | | 1 |
| N. Nervous system | Anesthetics, local | 1 | 2 | |
| | Analgesics, opioids | 8 | 7 | 6 |
| | Other analgesic and antipyretics | 49 | 23 | 51 |
| | Antimigraine preparations | 4 | 1 | |
| | Antipsychotics | | 3 | 2 |
| | Anxiolytics | 3 | 4 | 1 |
| | Hypnotics and sedatives | 3 | 3 | 8 |
| | Antidepressants | 12 | 9 | 5 |
| | Psychostimulants, agents used for ADHD and nootropics | 1 | 1 | |
| | Parasympathomimetics | 1 | | |
| | Drugs used in nicotine dependence | 1 | | |
| | General anesthetics | 2 | 1 | 2 |
| P. Antiparasitic products, insecticides and repellents | Agents against amoebiasis and other protozoal diseases | | 1 | |
| | Antinematodal agents | | 1 | |
| R. Respiratory system | Decongestants and other nasal preparations for topical use | 1 | 3 | 6 |
| | Nasal decongestants for systemic | 4 | 3 | 1 |
| | Adrenergics, inhalants | 2 | 8 | 4 |
| | Other drugs for obstructive airway diseases, inhalants | 1 | 3 | 2 |
| | Adrenergics for systemic use | 1 | 1 | |
| | Other systemic drugs for obstructive airway diseases | 1 | | |
| | Cough and cold preparations | 2 | 5 | 2 |
| | Antihistamines for systemic use | 12 | 8 | 8 |
| S. Sensory organs | Ophthalomolgical | 1 | | |
| | Ophthalomolgical antiinfectives | 4 | 2 | 2 |
| | Ophthalomolgical antiglaucoma preparations and miotics | 1 | 3 | |
| | Ophthalmological mydriatics and cycloplegics | 2 | | |
| | Ophthalmological decongestants and antiallergics | | 1 | 3 |
| | Ophthalomolgical corticosteroids and anti-infectives in combination | 2 | 1 | |

Figures in the table refer to number of patients using each category of drug. Since a single patient may have used several medications, the total number of occurrences does not equal the total number of patients in each treatment group. Three patients in the low-dose C-peptide group, six patients in the high-dose C-peptide group, and six patients in the placebo group had not taken any medication within 4 weeks prior to study start nor had they any ongoing medication during the study.

Neurophysiological Assessments

Baseline neurophysiological characteristics of the patients are presented in Tables E11 and E12. Nerve conduction velocity in the sural and peroneal nerves was assessed with good reproducibility (coefficient of variation 2-3%). The reproducibility of the compound action potentials had considerably higher variability as known from previous studies.

TABLE E11

Baseline data on neurophysiological assessments
(ITT data set, n = 161)

| | Low-dose C-peptide n = 56 | | High-dose C-peptide n = 52 | | Placebo n = 53 | |
|---|---|---|---|---|---|---|
| | Mean ± SD | Median (min; max) | Mean ± SD | Median (min; max) | Mean ± SD | Median (min; max) |
| SCVp (m/s) | 35.29 ± 3.42 | 35.76 (26.68; 43.03) | 35.78 ± 3.43 | 35.75 (25.18; 42.60) | 35.29 ± 3.76 | 36.13 (25.40; 41.63) |
| SCVp (SDS) | −2.49 ± 0.95 | −2.30 (−5.46; −0.83) | −2.59 ± 0.93 | −2.42 (−5.74; −1.24) | −2.78 ± 1.19 | −2.56 (−6.92; −1.07) |
| SCVi (m/s) | 44.35 ± 4.52 | 44.89 (31.75; 56.00) | 44.65 ± 4.57 | 44.84 (34.90; 54.23) | 43.91 ± 5.13 | 43.78 (31.53; 52.70) |
| SCVi (SDS) | −3.04 ± 0.97 | −2.95 (−5.98; −1.34) | −3.26 ± 0.99 | −3.05 (−5.59; −1.21) | −3.46 ± 1.26 | −3.33 (−7.50; −1.32) |
| SNAP (W) | 4.60 ± 3.32 | 3.66 (0.88; 16.76) | 5.14 ± 3.65 | 3.85 (0.98; 18.50) | 4.33 ± 3.21 | 3.35 (0.94; 14.00) |
| MCV (m/s) | 39.29 ± 5.51 | 39.61 (20.68; 47.65) | 40.71 ± 3.61 | 39.70 (34.28; 51.13) | 40.35 ± 4.42 | 41.05 (25.33; 49.58) |
| CMAP (mV) | 3.27 ± 2.33 | 2.83 (0.13; 12.88) | 3.51 ± 2.07 | 3.01 (0.33; 9.18) | 3.12 ± 2.01 | 3.08 (0.15; 8.15) |
| MDL (ms) | 4.59 ± 0.86 | 4.40 (3.43; 8.33) | 4.37 ± 0.51 | 4.34 (3.38; 5.68) | 4.56 ± 0.86 | 4.45 (3.25; 7.90) |

Sensory nerve conduction velocity in the sural nerves (SCVp) was reduced in the patients at baseline (−2.62 SD as compared to a healthy population). The peak velocity (SCVp) amounted on average to 35.4 m/s and the SCVi to 44.3 m/s (−3.25 SD from normal). Also motor nerve conduction velocity in the peroneal nerves was reduced, mean 40.1 m/s, corresponding to −2.95 SD.

TABLE E12

Baseline data for the PP population with
"SCVp >−2.5 SD at baseline"

| | Low-dose C-peptide n = 31 | | High-dose C-peptide n = 18 | | Placebo n = 21 | |
|---|---|---|---|---|---|---|
| | Mean ± SD | Median (min; max) | Mean ± SD | Median (min; max) | Mean ± SD | Median (min; max) |
| SCVp (m/s) | 37.07 ± 2.36 | 37.15 (31.48; 43.03) | 38.64 ± 2.41 | 38.14 (34.00; 42.60) | 38.01 ± 1.85 | 38.20 (33.58; 41.63) |
| SCVp (SDS) | −1.83 ± 0.43 | −1.87 (−2.50; −0.83) | −1.87 ± 0.35 | −1.92 (−2.48; −1.24) | −1.78 ± 0.35 | −1.75 (−2.32; −1.21) |
| SCVi (m/s) | 46.40 ± 3.60 | 46.43 (39.03; 56.00) | 48.26 ± 3.55 | 48.03 (41.80; 54.23) | 47.50 ± 2.92 | 47.25 (42.30; 52.70) |
| SCVi (SDS) | −2.46 ± 0.61 | −2.51 (−3.69; −1.34) | −2.59 ± 0.58 | −2452 (−3.67; −1.21) | −2.46 ± 0.65 | −2.34 (−3.73; −1.32) |
| MCV (m/s) | 41.46 ± 3.76 | 41.65 (33.65; 47.65) | 43.01 ± 3.83 | 42.55 (37.00; 51.13) | 41.85 ± 3.18 | 42.35 (33.35; 46.48 |
| MCV (SDS) | −2.28 ± 1 0.15 | −2.48 (−4.77; -0.34) | −2.32 ± 0.98 | −2.38 (−4.23; −0.43) | −2.41 ± 0.74 | −2.34 (−3.60; −0.89) |

Quantitative Sensory Assessments

Quantitative sensory testing revealed elevated thresholds at baseline, especially to vibration and cold stimulation, which were more pronounced in the feet than in the lower legs, Table E13. The reproducibility of the perception thresholds assessments were significantly less than for conduction velocity (coefficient of variation for vibration 21%, heat 14%, and cold 21%).

TABLE E13

Baseline data on quantitative sensory function
assessments (ITT data set, n = 161)

| | Low-dose C-peptide n = 56 | | High-dose C-peptide n = 52 | | Placebo n = 53 | |
|---|---|---|---|---|---|---|
| | Mean ± SD | Median (min; max) | Mean ± SD | Median (min; max) | Mean ± SD | Median (min; max) |
| Cold threshold foot (SDS) | 3.04 ± 2.11 | 2.82 (−2.32; 7.37) | 3.34 ± 2.13 | 3.28 (−0.59; 8.01) | 3.71 ± 2.11 | 3.96 (−0.96; 7.92) |
| Cold threshold lower leg (SDS) | 1.98 ± 1.62 | 1.75 (−1.18; 5.65) | 2.47 ± 1.99 | 2.43 (−1.38; 8.28) | 2.50 ± 2.00 | 2.13 (−1.14; 8.64) |
| Heat threshold foot (SDS) | 1.13 ± 0.82 | 1.19 (−0.75; 3.06) | 1.20 ± 1.03 | 1.24 (−1.68; 3.37) | 1.40 ± 0.97 | 1.26 (−0.58; 3.61) |
| Heat threshold lower leg (SDS) | 0.66 ± 1.06 | 0.75 (−3.14; 2.93) | 0.93 ± 1.31 | 1.16 (−2.79; 3.26) | 0.85 ± 1.12 | 0.93 (−1.28; 3.38) |
| Vibration threshold foot (SDS) | 1.73 ± 1.37 | 1.77 (−0.85; 4.40) | 1.96 ± 1.48 | 1.75 (−0.81; 7.78) | 2.06 ± 1.58 | 1.76 (−0.79; 6.02) |
| Vibration threshold lower leg (SDS) | 0.49 ± 0.92 | 0.44 (−1.33; 2.83) | 0.77 ± 1.27 | 0.47 (−0.98; 6.81) | 0.72 ± 1.13 | 0.51 (−1.37; 4.37) |

SDS = standard deviation score

Neurological Impairment Assessments and Symptoms

Pathological neurological findings (NIA>7 points) were present in 86% of the patients at baseline when assessed by the neurological examination. The average NIA score was 17.1 points, Table E14. The reproducibility for the neurological assessment was >25% (coefficient of variation).

TABLE E14

Baseline data on neurological assessment (ITT data set, n = 161)

| | Low-dose C-peptide n = 56 | | High-dose C-peptide n = 52 | | Placebo n = 53 | |
|---|---|---|---|---|---|---|
| | Mean ± SD | Median (min; max) | Mean ± SD | Median (min; max) | Mean ± SD | Median (min; max) |
| Neurological assessments | | | | | | |
| Total NIA score | 17.20 ± 9.65 | 16.0 (0.0; 39.0) | 16.92 ± 9.45 | 16.50 (0.0; 46.0) | 17.15 ± 11.44 | 16.0 (0.0; 56.57) |
| Great toe score | 7.23 ± 4.77 | 7.0 (0.0; 19.0) | 8.12 ± 4.23 | 8.00 (0.0; 18.0) | 7.14 ± 4.40 | 6.0 (0.0; 18.0) |
| Foot score | 4.59 ± 3.60 | 4.0 (0.0; 14.0) | 4.12 ± 3.41 | 4.00 (-0.0; 16.0) | 4.13 ± 3.70 | 4.0 (0.0; 16.67) |
| Lower leg score | 1.64 ± 2.03 | 1.0 (0.0; 8.0) | 1.65 ± 2.51 | 0.0 (0.0; 12.0) | 2.23 ± 3.02 | 0.0 (0.0; 14.0) |
| Symptom assessments | | | | | | |
| Total symptom score | 0.59 ± 1.06 | 0.00 (0; 4) | 0.75 ± 1.38 | 0.00 (0; 6) | 0.43 ± 0.69 | 0.00 (0; 3) |

Thirty five (35) percent of the randomized patients reported subjective symptoms from the lower limbs at baseline. Seven (7) of the patients presented with symptoms in their upper limbs.

ECG and Vital Signs

Baseline data on ECG recordings and vital signs are shown in Table E15. Sixteen (16) percent of the patients presented with an abnormal ECG at baseline. The following abnormalities were reported (number of patients in parentheses)—none was of serious clinical significance in the opinion of the investigator:

sinus tachycardia (2)

right electrical axis (2)

minor intraventricular conduction defect (1)

QRS deviation as after inferior myocardial infarction (1)

bundle block (6)

prolonged QTc interval or borderline (4)

slight ST-T changes (3)

TABLE E15

Baseline ECG and vital signs (ITT data set)

| | Low-dose C-peptide n = 56 | | High-dose C-peptide n = 52 | | Placebo n = 53 | |
|---|---|---|---|---|---|---|
| Variable | Mean ± SD | Median (min; max) | Mean ± SD | Median (min; max) | Mean ± SD | Median (min; max) |
| Heart rate (beats/min) | 71.5 ± 11.0 | 72 (51; 104) | 74.3 ± 11.7 | 74 (47; 102) | 73.7 ± 10.2 | 72 (54; 103) |
| QTc-interval (ms) Bazett | 401 ± 17 | 399 (368; 445) | 404 ± 22 | 400 (350; 460) | 406 ± 21 | 403 (367; 461) |
| QTc-interval (ms) Fredericia | 390 ± 16 | 389 (358; 432) | 389 ± 18 | 384 (350; 442) | 393 ± 18 | 391 (358; 433) |
| BPs (mm Hg) | 131 ± 15.7 | 130 (102; 180) | 132.7 ± 15.1 | 132 (98; 180) | 133.3 ± 13.9 | 134 (105; 160) |
| BPd (mm Hg) | 77 ± 10.1 | 79.5 (52; 111) | 76.1 ± 9.9 | 78.5 (54; 95) | 76.9 ± 7.0 | 78 (60; 90) |

BPs = systolic blood pressure; BPd = diastolic blood pressure

Clinical Assessments after 3 Months (Visit 2)

Glycemic control (HbA1 c) was slightly decreased in all three treatment groups by on average 0.2%.

Clinical Assessments after 6 Months (Visit 4)

Metabolic Control (HbA1c)

The change of metabolic control, as reflected by reduced HbA1 c, is presented in Table E16. There was a statistical significant reduction in the low-dose C-peptide group, but the reduction was even greater in the placebo group. Statistical correlation analyses did not show any correlation between the change in HbA1c with the change in SCV after 6 months of treatment.

TABLE E16

Change in HbA1c at 6 months (visit 4) (ITT data set)

|  | Low-dose C-peptide n = 55 | | High-dose C-peptide n = 43 | | Placebo n = 49 | | $p <$ C-peptide groups vs. placebo | $p <$ Low- vs. high-dose groups |
| --- | --- | --- | --- | --- | --- | --- | --- | --- |
|  | Mean ± SD [$p <$ within group] | Median (min-max) | Mean ± SD [$p <$ within group] | Median (min-max) | Mean ± SD [$p <$ within group] | Median (min-max) | | |
| HbA1c | −0.21 ± 0.70 [0.013] | −0.20 (−2.20; 1.90) | −0.03 ± 0.77 [ns] | −0.10 (−2.20; 1.50) | −0.42 ± 0.72 [0.001] | −0.30 (−2.30; 0.90) | ns | ns | ns = not significant

Insulin Requirements

Figure 3:
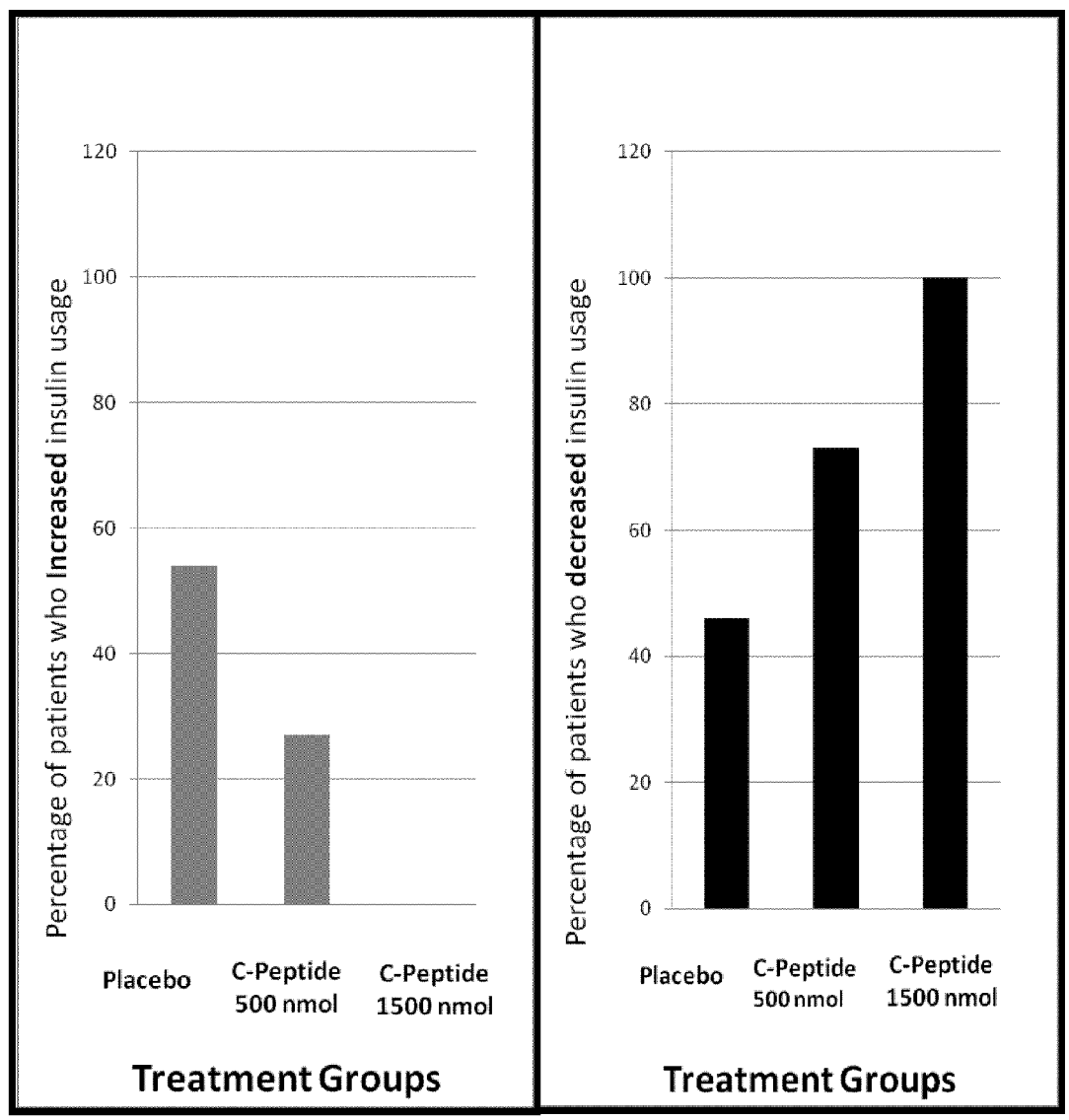
FIG. 3 shows the change in reported insulin requirements at 6 months as compared to baseline insulin usage in a sub-population of responding patients.

In the retrospective review of insulin requirements after 6 months of C-peptide therapy there were notes found in ~70% of the patients' charts. Out of these, 40 patients, corresponding to 39% of the patients, reported that their insulin dose regimen had changed during the study period Table E17 (FIG. 3). The majority of the patients had reduced their insulin doses, and in a comparison between the placebo patients and those receiving C-peptide the insulin doses were significantly reduced in the latter group (p<0.003).

TABLE E17

Change in insulin requirements at 6 months as compared to baseline

| Insulin dose | Low-dose C-peptide n = 15 | High-dose C-peptide n = 12 | Placebo n = 13 |
| --- | --- | --- | --- |
| Increased insulin dose | 4 (27%) | 0 | 7 (54%) |
| Reduced insulin dose | 11 (73%) | 12 (100%) | 6 (46%) |

Patients receiving high-dose C-peptide therapy showed a more pronounced reduction in insulin administration compared to the low-dose C-peptide and placebo groups. Treatment and placebo groups were statistically significant (Active—Placebo p<0.003; High—Placebo p<0.005). Differences between the high- and low-dose C-peptide groups were less significant (p<0.07).

Patients reporting reduced insulin usage, required on average about 14% less insulin compared to their daily insulin requirement before starting C-peptide therapy. More importantly the range of insulin reduction observed during these studies (2% to 32%) varied by more than 10-fold among different patients. These numbers refer to the long-term adjustment of insulin dose that the patients made during C-peptide therapy. It is therefore possible that greater reductions may have been made for short periods of time or on single occasions, but were not reported in the current study. In fact as shown below, C-peptide therapy significantly increased the incidence of hypoglycemic coma compared to the placebo-treated group, even in spite of these reductions in insulin usage (Table E18).

TABLE E18

Incidence of hypoglycemic events and hypoglycemic coma. Numbers in parentheses denote numbers of AEs, in judgment of the investigator, probably/possibly was related to study drug.

| System Organ Class | Preferred Term | Low-dose C-peptide | High-dose C-peptide | Placebo |
| --- | --- | --- | --- | --- |
| Metabolism and nutritional disorders | Blood glucose fluctuation | 0 | 0 | 1 |
| | Hyperglycemia | 1 (1) | 1 | 1 |
| | Hypoglycemia | 2 (1) | 5 (1) | 5 |
| | Hypoglycemic coma | 2 | 2 | 0 |
| | Hyperlipidemia | 1 | 0 | 0 |
| | Hypothyroidism | 0 | 0 | 1 |
| | Increased appetite | 0 | 0 | 1 |
| | Insulin sensitivity | 1 (1) | 0 | 1 (1) |
| | Vitamin B12 deficiency | 0 | 1 | 0 |

Table E18 shows treatment emergent adverse events of any severity for only metabolic and nutritionally related disorders; a complete listing of all emergent adverse events is provided in Table E26. The clinical trial data demonstrates that treatment with C-peptide resulted in 4 occurrences of hypoglycemic coma compared to none in the placebo group. It should also be noted that hypoglycemic events were not reported as adverse events unless the severity of the event required assistance by another person or else in the opinion of the investigator should be reported as an adverse event. Thus it is possible that hypoglycemic events may have been under reported in this study. Accordingly, the current study clearly establishes that C-peptide therapy was associated with an increase in the rate of hypoglycemic coma compared to the placebo group. Consistent with the patient reported reduction in insulin administration, the present study demonstrates a connection between C-peptide therapy and an increased risk of hypoglycemia, and in particular the risk of severe hypoglycemia and coma in a subset of patients.

C-Peptide Concentrations

Figure 4:
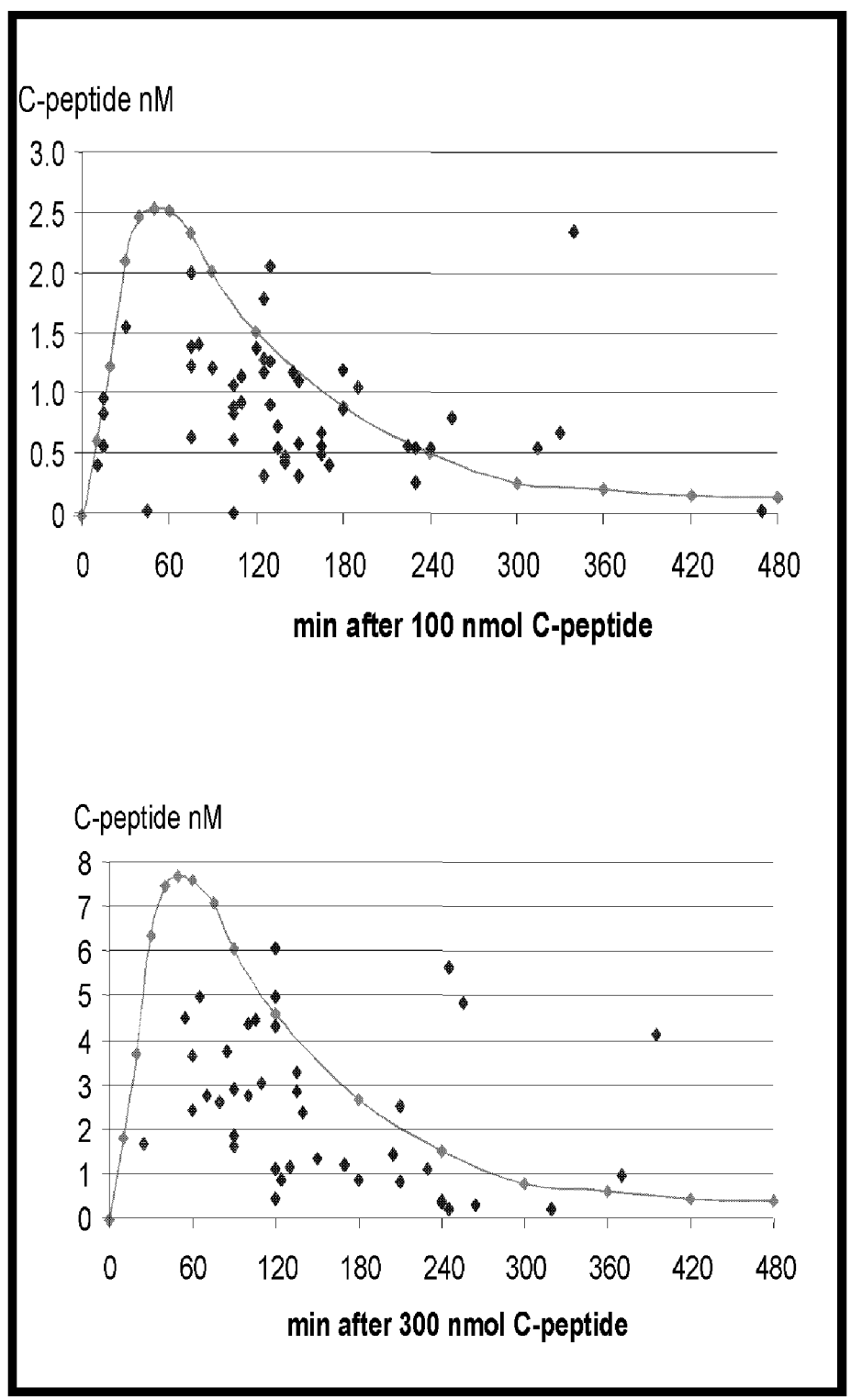
FIG. 4 shows C-peptide plasma levels in the low- and high-dose groups at the 3 month visit (diamond symbols) in relation to theoretical pharmacokinetic data (solid line) extrapolated from an earlier study.

C-peptide plasma levels were measured at baseline, and after 3 and 6 months of treatment. Analysis was performed by the Department of Clinical Chemistry Karolinska University Hospital, Solna using a time-resolved fluoroimmunoassay (AutoDelfia, Wallac Oy, Turku, Finland). Compared to data generated in an earlier pharmacokinetic study, the concentrations obtained in the present study are slightly lower than expected (FIG. 4), but the results demonstrate similar variability as for, e.g., insulin when administered by the patients under everyday-like conditions. The plasma levels of C-peptide attained in this study ranged from about 0.2 nM to a maximum of about 6 nM in the high dose group.

C-peptide plasma levels were also measured pre-dosing in the morning in 22 randomly selected patients at the Karolinska Hospital after 4.5 months of study treatment (visit 3). As compared to the C-peptide concentration at baseline, the C-peptide plasma level at this visit was unchanged in the placebo-treated patients (0±0.008 nmoL/L; n=10), increased by 0.045±0.092 nmoL/L in the low-dose C-peptide group (n=8) and increased by 0.13±0.083 nmoL/L in the high-dose C-peptide group (n=4). Although the patient number is very small, it must be concluded that there is likely no significant accumulation occurring following repeated C-peptide dosing in the dose ranges employed in the present study.

Change from Baseline (BL) to 6 Months Treatment (Visit 4) in Neurophysiological Assessments Following C-peptide administration for 6 months there was significant improvement of SCV in the active groups (low- and high-dose C-peptide groups combined), but this change was not significantly different from that of the placebo group (Table E20). Analyzing the numbers of responders, defined as a patient with an improvement in SCVp of >1 m/s, in each treatment group, there were 19% in the placebo group vs. 37% in the active group (p<0.0317; Table E19). There was no statistically significant difference between the responses in the low- and high-dose C-peptide groups.

TABLE E19

Responders per treatment group. A responder is defined as patients with improvement in SCVp of >1 m/s from baseline, an improvement suggested to be of clinical significance, taking study duration into consideration (DCCT Group 1995a).* p < 0.0317, C-peptide groups vs. placebo group with Pearson Chi-square test.

|  | C-peptide groups n = 92 | Placebo group n = 47 |
|---|---|---|
| Numbers of responders | 34 | 9 |
| Responders per treatment group | 37.0%* | 19.1% |

TABLE E20

Change from baseline to 6 months treatment (mean and median differences) in neurophysiological function (PP data set). Improvements in MCV, SCV, CMAP, and SNAP are indicated by positive differences.

|  | Low-dose C-peptide n = 53 | | High-dose C-peptide n = 39 | | Placebo n = 47 | | p < C-peptide groups vs. placebo | p < Low- vs. high-dose groups |
|---|---|---|---|---|---|---|---|---|
|  | Mean ± SD [p < within group] | Median (min; max) | Mean ± SD [p < within group] | Median (min; max) | Mean ± SD [p < within group] | Median (min; max) |  |  |
| SCVp (m/s) | 0.38 ± 1.95 [ns] | 0.48 (−6.12; 40) | 0.63 ± 1.65 [0.028] | 0.30 (−2.33; 5.80) | 0.24 ± 1.87 [ns] | 0.33 (−3.57; 8.18) | ns | ns |
| SCVi (m/s) | 0.77 ± 3.13 [0.052] | 0.52 (−9.85; 8.22) | 1.14 ± 2.23 [0.004] | 1.03 (−3.45; 6.45) | 0.75 ± 2.62 [ns] | 1.25 (−4.15; 9.65) | ns | ns |
| SNAP (μV) | −0.06 ± 1.21 | −0.13 (−2.80; 3.93) | 0.09 ± 1.30 | 0.13 (−2.95; 4.70) | 0.24 ± 1.54 | 0.05 (−3.03; 7.03) | ns | ns |
| MCV (m/s) | −0.25 ± 1.39 | −0.18 (−4.35; 2.15) | −0.57 ± 1.53 [0.026] | −0.70 (−3.70; 2.98) | −0.53 ± 1.48 [0.034] | −0.25 (−5.0; 2.13) | ns | ns |
| CMAP (mV) | −0.15 ± 0.49 | −0.13 (−1.33; 0.88) | −0.17 ± 0.72 | −0.07 (−2.23; 1.15) | −0.15 ± 0.53 | −0.08 (−2.35; 0.75) | ns | ns |
| MDL (ms) | 0.05 ± 0.44 | 0.03 (−1.20; 1.10) | −0.0 ± 0.22 | 0.0 (−0.45; 0.65) | 0.01 ± 0.46 | 0.05 (−0.85; 1.55) | ns | ns | ns = not significant

Figure 5:
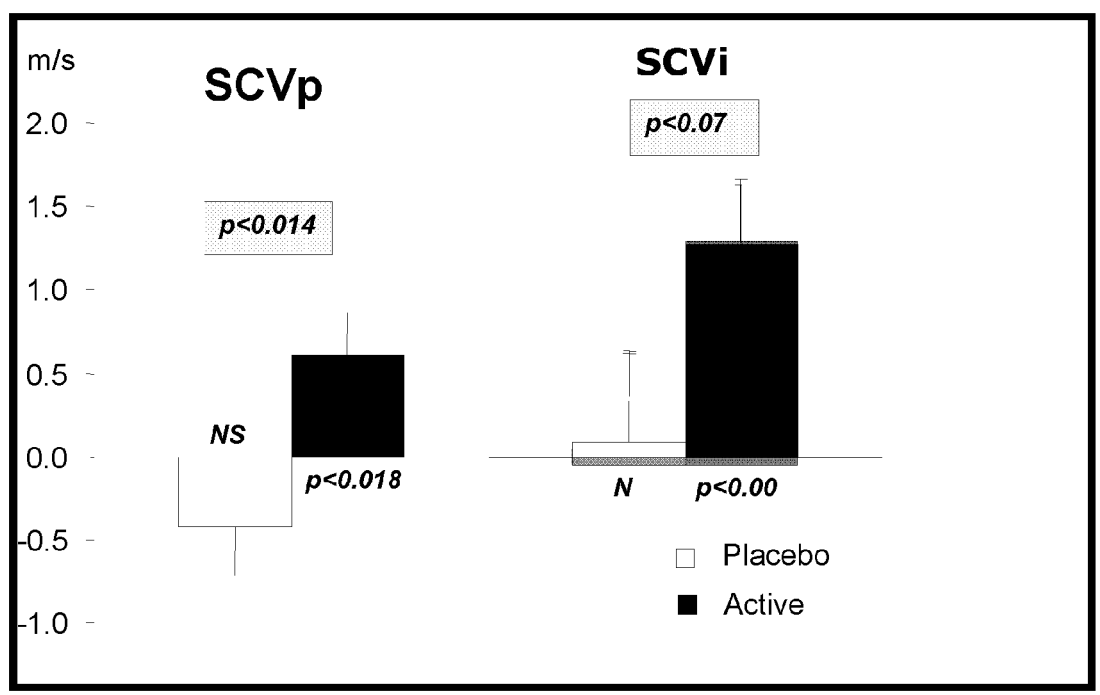
FIG. 5 shows the change in peak sensory nerve conduction velocity (SCVp) from baseline to 6 months of treatment in patients with SCVp>−2.5 standard deviations (SD) at baseline.

With a study duration as short as 6 months it is conceivable that patients who were less affected with neuropathy at baseline have a greater potential for an improvement during this relatively short treatment period. Thus, a subgroup analysis was performed in the subset of patients with less affected SCVp at baseline (SCVp>−2.5 SD, n=70). In this group, C-peptide induced an improvement of SCVp amounting to 1.03 m/s greater than that of the placebo group (C-peptide: 0.61 m/s; placebo: −0.42 m/s; p<0.015), FIG. 5; Table E21. In this group of patients there were no statistically significant differences in response to C-peptide in low and high doses.

TABLE E21

Change from baseline to 6 months treatment (mean and median differences) in neurophysiological assessments in the subgroup of patients with SCVp > −2.5 SD at baseline, treated with low-dose C-peptide, high-dose C-peptide, and placebo.

| | Low-dose C-peptide n = 31 | | High-dose C-peptide n = 18 | | Placebo n = 21 | | p < C-Low-peptide group vs. placebo | p < Low- vs. high-dose groups |
|---|---|---|---|---|---|---|---|---|
| | Mean ± SD [p-within group] | Median (min-max) | Mean ± SD [p < within group] | Median (min-max) | Mean ± SD [p < within group] | Median (min-max) | | |
| SCVp (m/s) | 0.46 ± 1.94 [ns] | 0.68 (−3.23; 4.0) | 0.86 ± 1.33 [0.004] | 0.63 (−2.27; 3.27) | −0.42 ± 1.32 [ns] | −0.05 (−3.57; 1.45) | 0.014 | ns |
| SCVi (m/s) | 1.13 ± 2.76 [0.032] | 0.88 (−5.25; 6.30) | 1.53 ± 2.19 [0.010] | 2.16 (−3.45; 4.50) | 0.07 ± 2.51 [ns] | 0.60 (−3.50; 3.63) | 0.077 | ns |
| SNAP (µV) | 0.08 ± 1.43 [ns] | −0.13 (−2.80; 3.93) | 0.47 ± 1.69 [ns] | 0.40 (−2.95; 4.70) | 0.90 ± 1.74 [ns] | 0.47 (−1.95; 7.03) | ns | ns |
| MCV (m/s) | −0.34 ± 1.43 [ns] | −0.35 (−4.35; 2.15) | −0.65 ± 1.19 [0.049] | −0.77 (−3.10; 1.28) | −0.55 ± 1.56 [ns] | −0.45 (−5.0; 1.88) | ns | ns |
| CMAP (mV) | −0.13 ± 0.54 [ns] | −0.10 (−1.33; 0.88) | −0.26 ± 0.78 [ns] | −0.29 (−2.23; 1.15) | −0.11 ± 0.55 [ns] | −0.07 (−1.68; 0.75) | ns | ns |
| MDL (ms) | 0.05 ± 0.44 [ns] | 0.02 (−0.80; 1.10) | −0.05 ± 0.27 [ns] | −0.10 (−0.45; 0.65) | 0.05 ± 0.38 [ns] | 0.15 (−0.60; 0.72) | ns | ns | ns = not significant

Figure 6:
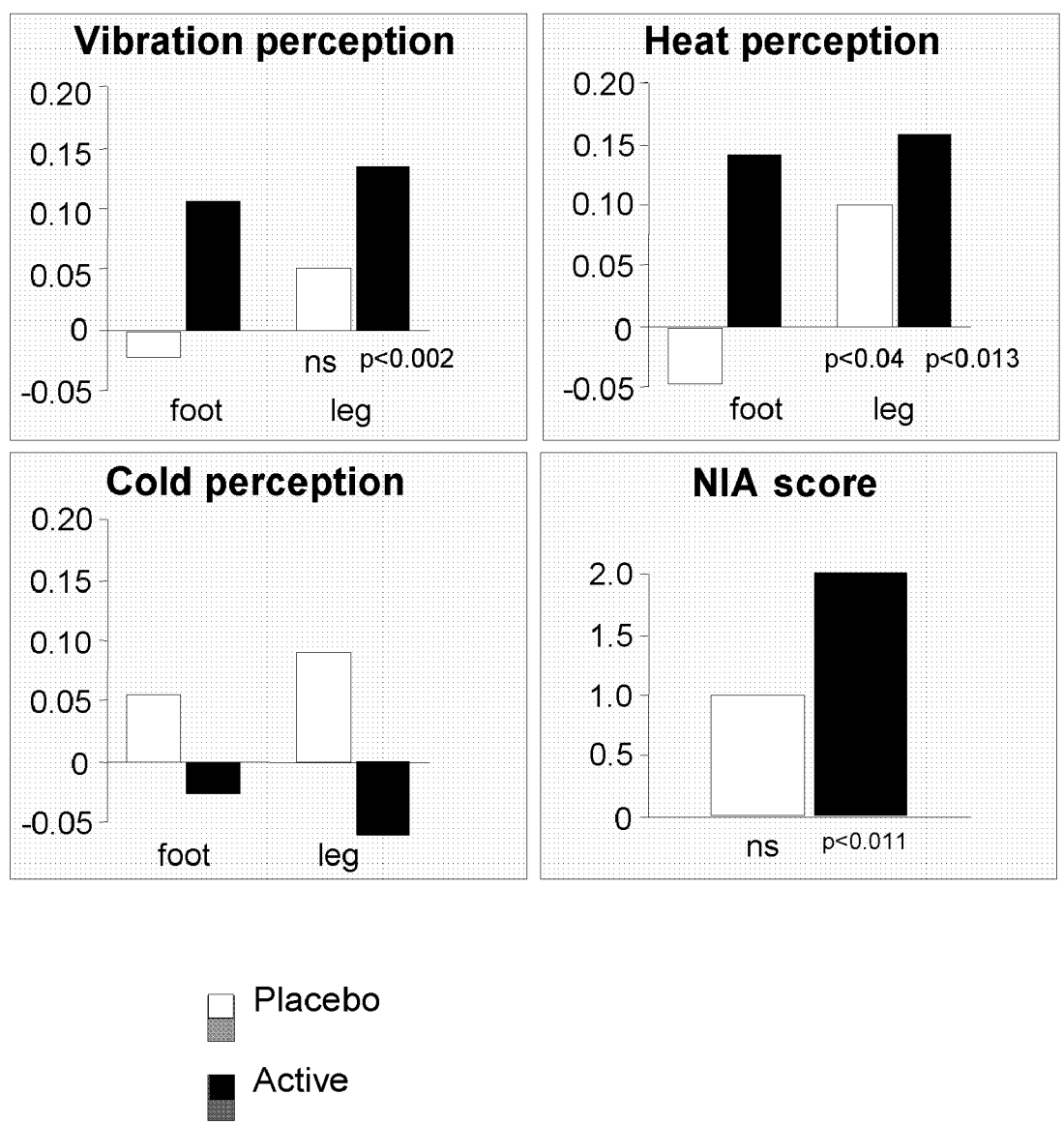
FIG. 6 shows the median changes in perception thresholds and neurological impairment assessment scores in patients from baseline to 6 months of treatment.

Change from Baseline (BL) to 6 Months Treatment (Visit 4) in Quantitative Sensory Function Assessments Following C-peptide administration, there was a tendency towards an improvement in the C-peptide-treated groups for vibration and heat perception as compared to placebo, but it did not reach statistical significance (Table E22; FIG. 6). C-peptide did not have an effect on cold perception.

Change from Baseline (BL) to 6 Months Treatment (Visit 4) in Neurological Impairment Assessments and Symptoms Following C-peptide administration for 6 months there was a significant improvement in total NIA score. The score was decreased by −2.16 points (both C-peptide groups), but this change was not statistically significantly different from that in the placebo group (−0.94 point), FIG. 6. No significant changes in symptoms were observed during the study. See Table E23.

TABLE E22

Change from baseline to 6 months treatment (mean and median differences) in quantitative sensory function (PP data set). Improvements in QST are

| | Low-dose C-peptide n = 53 | | High-dose C-peptide n = 39 | | Placebo n = 47 | | p < C-peptide group vs. placebo | p < Low-peptides vs. high-dose groups |
|---|---|---|---|---|---|---|---|---|
| | Mean ± SD [p < within group] | Median (min; max) | Mean ± SD [p < within group] | Median (min; max) | Mean ± SD [p < within group] | Median (min; max) | | |
| Cold threshold foot (SDS) | 0.14 ± 1.33 [ns] | −0.02 (−3.04; 4.73) | −0.18 ± 1.27 [ns] | 0.04 (−3.34; 2.10) | −0.10 ± 0.86 [ns] | −0.06 (−1.71; 1.61) | ns | ns |
| Cold threshold lower leg (SDS) | 0.10 ± 1.13 [ns] | 0.19 (−2.67; 3.40) | −0.12 ± 1.06 [ns] | 0.01 (−2.18; 2.47) | −0.07 ± 0.94 [ns] | −0.09 (−1.93; 2.0) | ns | ns |
| Heat threshold foot (SDS) | −0.08 ± 0.59 [ns] | −0.22 (−1.42; 1.15) | −0.10 ± 0.81 [ns] | −0.01 (−2.44; 1.60) | −0.02 ± 0.61 [ns] | 0.05 (−1.30; 1.34) | ns | ns |
| Heat threshold lower leg (SDS) | −0.30 ± 0.74 [0.006] | −0.26 (−1.79; 1.31) | −0.07 ± 0.82 [ns] | −0.12 (−2.09; 2.24) | −0.21 ± 0.63 [0.041] | −0.10 (−1.66; 1.30) | ns | ns |
| Vibration threshold foot (SDS) | −0.07 ± 0.68 [ns] | −0.11 (−1.42; 2.18) | −0.12 ± 0.69 [ns] | −0.10 (−1.93; 0.92) | −0.03 ± 0.86 [ns] | 0.02 (−2.75; 2.16) | ns | ns |
| Vibration threshold lower leg (SDS) | −0.18 ± 0.46 [0.013] | −0.09 (−1.61; 0.68) | −0.22 ± 0.79 [0.057] | −0.24 (−2.64; 2.18) | −0.09 ± 0.57 [ns] | −0.05 (−1.97; 1.17) | ns | ns | ns = not significant

TABLE E23

Change from baseline to 6 months treatment (mean and median differences) in neurological assessments and symptoms (PP data set). Improvements in NIA and symptom assessment (SA) are indicated by negative differences.

| | Low-dose C-peptide n = 53 | | High-dose C-peptide n = 39 | | Placebo n = 47 | | p < C-peptide groups vs. placebo | p < Low- vs. high-dose groups |
|---|---|---|---|---|---|---|---|---|
| | Mean ± SD [p < within group] | Median (min; max) | Mean ± SD [p < within group] | Median (min; max) | Mean ± SD [p < within group] | Median (min; max) | | |
| *Neurological assessments* | | | | | | | | |
| Total NIA score | −1.74 ± 7.06 [ns] | −2.0 (−18.0; 16.0) | −2.75 ± 8.18 [0.043] | −2.0 (−38.0; 10.0) | −0.94 ± 6.45 [ns] | −1.0 (−15.0; 17.0) | ns | ns |
| Big toe score | −0.38 ± 3.56 | 0 (−9.0; 8.0) | −1.32 ± 3.80 | −1.0 (−14.00; 6.0) | −0.37 ± 3.25 | 0 (−8.0; 6.0) | ns | ns |
| Foot score | −0.88 ± 2.88 | 0 (−8.0; 7.0) | −1.24 ± 3.65 | 0 (−14.0; 7.0) | −0.16 ± 2.75 | 0 (−7.0; 6.0) | ns | ns |
| Lower leg | −0.55 ± 1.91 | 0 (−5.0; 4.0) | −0.55 ± 2.65 | 0 (−12.0; 4.0) | −0.96 ± 2.15 | 0 (−5.0; 6.0) | ns | ns |
| *Symptom assessment* | | | | | | | | |
| Sum Symptom Score | −0.02 ± 1.03 [ns] | 0.0 (−3.0; 3.0) | −0.13 ± 1.22 [ns] | 0.0 (−5.0; 3.0) | −0.07 ± 0.68 [ns] | 0.0 (−2.0; 2.0) | ns | ns | ns = not significant

Change from Baseline (BL) to 6 Months Treatment (Visit 4) in Autonomic Nerve Function The change in E/I ratio is presented in Table E24. There was no significant effect on the E/I ratio in any of the three treatment groups. In the subgroup of patients with pathological E/I ratio at baseline, the change in E/I ratio was on average 1% (not significant).

TABLE E24

Change from baseline to 6 months treatment (mean and median differences) in autonomic nerve function (ITT data set), excluding patients on concomitant beta-blockers. Improvements in E/I ratio are indicated by positive differences.

| | Low-dose C-peptide n = 50 | | High-dose C-peptide n = 48 | | Placebo n = 48 | | p < C-peptide groups vs. placebo | p < vs. high-dose groups |
|---|---|---|---|---|---|---|---|---|
| | Mean ± SD [p < within group] | Median (min; max) | Mean ± SD [p < within group] | Median (min; max) | Mean ± SD [p < within group] | Median (min; max) | | |
| E/I ratio | −0.01 ± 0.06 [ns] | 0.00 (−0.22; 0.11) | 0.01 ± 0.07 [ns] | 0.00 (−0.24; 0.21) | 0.02 ± 0.13 [ns] | 0.00 (−0.09; 0.84) | ns | ns | ns = not significant; BPs = systolic blood pressure; BPd = diastolic blood pressure

TABLE E25

Change from baseline to 6 months treatment (mean and median differences) in ECG and vital signs recording (visit 4) (PP data set). A reduction in QTc is indicated by a negative difference.

| | Low-dose C-peptide n = 53 | | High-dose C-peptide n = 39 | | Placebo n = 47 | | p< |
|---|---|---|---|---|---|---|---|
| | Mean ± SD | Median (min-max) | Mean ± SD | Median (min-max) | Mean ± SD | Median (min-max) | |
| Heart rate (bpm) | −0.9 ± 8.2 | −2.0 (−20; 22) | −3.2 ± 10.0 | −4.0 (−22; 19) | −0.8 ± 9.4 | −2.0 (−20; 28) | ns |

TABLE E25-continued

Change from baseline to 6 months treatment (mean and median differences) in ECG and vital signs recording (visit 4) (PP data set). A reduction in QTc is indicated by a negative difference.

| | Low-dose C-peptide n = 53 | | High-dose C-peptide n = 39 | | Placebo n = 47 | | |
|---|---|---|---|---|---|---|---|
| | Mean ± SD | Median (min-max) | Mean ± SD | Median (min-max) | Mean ± SD | Median (min-max) | p< |
| QTc-interval (ms) Bazett | −0.1 ± 17.5 | 0.0 (−48; 47.2) | −4.5 ± 20.3 | 0.0 (−58; 36.6) | −2.0 ± 23.5 | 0.0 (−44; 100) | ns |
| QTc-interval (ms) Fredericia | 0.9 ± 14.1 | 1.3 (−43; 41.1) | −0.5 ± 16.2 | 0.0 (−44; 38.2) | −1.1 ± 18.6 | −3.3 (−31; 95.9) | ns |
| BPs (mm Hg) | −2.1 ± 12.8 | −1.0 (−40; 22) | −8.8 ± 10.0 | −8.0 (−34; 15) | −4.8 ± 12.2 | −4.0 (−41; 27) | ns |
| BPd (mm Hg) | −2.7 ± 8.2 | −1.0 (−28; 20) | −2.6 ± 8.0 | −1.0 (−22; 11) | −3.1 ± 8.0 | −5.0 (−20; 15) | ns |

ECG and Vital Signs

There were no clinically significant abnormalities in ECG reported during the study medication treatment, nor were there any significant changes in heart rate, blood pressure, and QTc in any of the three treatment groups (Table E25). However, there was a significantly greater decrease in systolic blood pressure in the high-dose C-peptide group compared to the low-dose C-peptide group (p<0.004), but this decrease was not statistically different from that in the placebo group.

Assessment of Antibody Formation Against C-Peptide

Samples for the assessment of antibody formation were collected at baseline and at visits 2 and 4. An appropriate enzyme-linked immunoabsorbant assay (ELISA) method was developed and assessments carried out. The results indicate no or very weak reactivity to C-peptide both at baseline and after 3 and 6 months of C-peptide treatment.

Compliance

The assessment of compliance was based on the integrated information obtained from the patient's diary with recordings of drug administration, by the visual control of returned unused and used vials and by questioning about any handling problems according to predetermined questions at clinical visits 1, 2, 3, and 4. Compliance was also checked after closure of the database by qualitative analysis of C-peptide in blood samples taken at visits 2 and 4. The final assessment as to the individual patient's compliance was made at the clean file meeting. Compliance was considered sufficient, i.e., >80% of the intended total study dose had been administered, in all patients but one in the high-dose C-peptide group and one in the low-dose C-peptide group. They were considered major violators and their data were excluded from the PP analysis of efficacy.

Statistical/Analytical Issues

Adjustments for Covariates

An improvement of the patient's glycemic control (HbA1c) was expected in all treatment groups and this change was evaluated. Exploratory multivariate analyses including possible predictors of the dependent variables were performed on the primary efficacy variable (change baseline to 6 months) using HbA1c as one of the predictors. There were no correlations found between change in glycemic control and change in SCV.

Handling of Dropouts or Missing Data

In the statistical calculations in the ITT population, last-value-carried-forward (LVCF) was used for missing data.

Multicenter Studies

Patients were recruited from 5 sites in Sweden: site 1. Karolinska Hospital, Stockholm; site 2. Lundby Hospital/Sahlgrenska University Hospital, Gothenburg; site 4. Linkbpings University Hospital; site 5. Uppsala University Hospital; and site 6. Huddinge University Hospital (site 3 withdrew their participation already before the study start). Potential "site-differences" were evaluated using multivariate analyses. There were no differences in study conduct, patient characteristics, or clinical settings with respect to response between the sites.

Use of an "Efficacy Subset" of Patients

The analyses of efficacy (primary and secondary variables) were performed in the PP data set and in those of the patients in the PP data set who had SCVp>−2.5 SD at baseline. The basis for the selection of this latter group rests with the possibility to influence severely affected nerves during a relatively short treatment period—with study duration as short as 6 months it is conceivable that patients who were less affected with neuropathy at baseline have a greater potential for an improvement during a relatively short treatment period. Thus, a subgroup analysis was performed in the subset of the patients, with less affected SCVp at baseline.

Drug-Drug and Drug-Disease Interactions

The exclusion criteria specifically excluded concurrent therapies with drugs, which potentially might interact with the effect of the investigational drug, i.e., $Ca^{2+}$-channel blockers. The study design and total number of patients in the study do not allow any conclusions as to a relationship between response and past and/or current illness or ongoing concomitant medication.

Efficacy Conclusions

Diabetic Neuropathy

It is concluded that C-peptide given in a therapeutic dose (500 nmoL/day) for 6 months exerts a beneficial effect on nerve function in patients with early stage neuropathy. The higher dose level (3 times the lower dose) did not result in a statistically significantly greater effect. The present study confirms and extends previous findings to a group of patients with manifest diabetic neuropathy.

Insulin Usage

It is concluded that in at least a subpopulation of patients, C-peptide replacement therapy results in a sustained reduction in insulin requirements. The higher dose level (3 times the lower dose) resulted in a slightly bigger effect, however this was not reach statistical significance difference (p<0.07) between the high and low doses of C-peptide. Patients reporting reduced insulin usage, required on average about 14% less insulin compared to their daily insulin requirement before starting C-peptide therapy. In a subpopulation of patients significantly greater decreases (up to 32%) in insulin usage were reported. This finding was both an important and unexpected finding compared to previous clinical trials with C-peptide.

Hypoglycemia

It is concluded that in at least a subpopulation of patients, C-peptide replacement therapy results in an increased risk of hypoglycemic coma. There was no clear difference in the incidence of coma with the high and low C-peptide doses. This increased incidence of hypoglycemic coma occurred even in the context of reduced insulin usage and strongly suggests that C-peptide therapy increases the risk of hypoglycemia in general, and in particular, the incidence of severe hypoglycemia, including hypoglycemic coma.

IV. Safety Evaluation

Extent of Exposure

The low-dose regimen was expected to give a mean physiological plasma concentration of ~1 nmoL/L during the 24 h period. The high dose regimen was expected to result in concentrations ~3 times those of the low dose regimen. The actual exposure is described in section above on "C-peptide concentrations". Blood samples for determination of C-peptide in plasma were drawn at the S/B visit, visit 2, and at end of study visit 4. The sampling of C-peptide in plasma at visits 2 and 4 coincided with the clinical visit and the time between the most recent administration of the trial drug and sampling varied between patients. Thereby, the results of C-peptide concentrations in plasma became less suitable for pharmacokinetic evaluations.

Brief Summary of Adverse Events

Fifty-two (52) patients in the high-dose C-peptide group, 56 patients in the low-dose C-peptide group, and 53 patients in the placebo group (ITT data set) were evaluated for safety.

No deaths were reported during the study. There were two SAEs reported during the study, and one patient withdrew from the study treatment due to an AE. In total, there were 173 AEs reported in 48 out of 56 patients (86%) in the low-dose C-peptide group, 154 AEs in 44 out of 52 patients (85%) in high-dose C-peptide group, and 166 AEs reported in 44 out of 53 patients (83%) in the placebo group. The most frequently reported AEs were headache and nasopharyngitis, both equally occurring between the three treatment groups (Table E26).

Display of Adverse Events

TABLE E26

Treatment emergent AEs of any severity listed by SOC and preferred term(PP data set). Numbers in parentheses denote numbers of AEs, possibly related to study drug.

| SOC | Preferred Term | Low-dose C-peptide | High-dose C-peptide | Placebo |
|---|---|---|---|---|
| Blood and lymphatic system disorder | Anemia | 1 | 1 | |
| | Hemorrhage | | 1 | |
| Cardiac disorder | Cardiac arrhythmia | 1 | | |
| | ST elevation (ECG) | 1 | | |
| | Tachycardia (stress | 1 | | |
| Eye disorder | Dacryocanaliculitis | 1 | | |
| | Macular edema | | 1 | 1 |
| | Retinopathy proliferative | | | 1 |
| | Vitreous hemorrhage | | 1 | |
| | Vision decreased | 1 | | |
| Gastro-intestinal Disorders | Abdominal pain | | 3 | 1 |
| | Aptyalism | | 1 | |
| | Celiac disease | 1 | | |
| | Constipation | | | 1 |
| | Diarrhea | 2 | 1 | 3 |
| | Dysphagia | | | 1 |
| | Flatulence | 1 | | |
| | Gastritis | | 1 | 1 |
| | Nausea | 1 | 4 | |
| | Reflux gastritis | 2 | | |
| | Tooth ache | 2 | 3 | 2 |
| General disorders and administration site conditions | Pyrexia | 3 | | 3 |
| | Chest pain | | 2 | |
| | Fatigue | | 2 | |
| | Feeling abnormal | | 3 | 4 (1) |
| | Injection site burning | | 1 (1) | |
| | Injection site hemorrhage | | | 2 (1) |
| | Peripheral edema | | | 3 |
| Immune system disorders | Allergic urticaria | 1 | | |
| | Dermatitis allergic | 1 | | 1 |
| | Rheumarthritis | 1 | | |
| | Season allergy | 1 | | |
| Infections and infestations | Acute HIV infection | 1 | | |
| | Borrelia infection | 1 | | |
| | Bronchitis | 1 | | |
| | Candidiasis | 2 | | |
| | Eye infection | | | 2 |
| | Gastroenteritis | 2 | 7 | 2 |
| | Herpes simplex | 1 | | |
| | Herpeszoster | 1 | | |
| | Influenza | 1 | | 4 |
| | Nasopharyngitis | 31 | 23 | 26 |
| | Otitis | 1 | 2 | |
| | Pharyngitis | 1 | 2 | 3 |
| | Perianal abscess | | | 1 |
| | Rhinitis | | | 1 |
| | Sinusitis | 4 | 2 | 2 |
| | Sepsis | | 1 | |
| | Skin infection | 5 | 1 | |
| | Tonsilitis | 1 | 2 | 1 |
| | Tooth infection | | 2 | 1 |
| | Upper respiratory tract infection | 3 | 1 | 3 |
| | Urinary tract infection | 3 | 1 | 6 |
| Injury poisoning, procedural complications | Alcohol poisoning | | | 1 |
| | Blister | | 2 | |
| | Dizziness | | 1 | |
| | Eye injury | | 1 | |
| | Food poisoning | | 1 | |
| | Joint sprain ankle | 1 | 1 | 1 |

TABLE E26-continued

Treatment emergent AEs of any severity listed by SOC and preferred term(PP data set). Numbers in parentheses denote numbers of AEs, possibly related to study drug.

| SOC | Preferred Term | Low-dose C-peptide | High-dose C-peptide | Placebo |
|---|---|---|---|---|
| | Knee injury | | 1 | |
| | Pain in extremity | | | 1 |
| | Rib fracture/injury | 1 | 2 | |
| | Scar | | 1 | |
| | Skin injury | 2 | | |
| | Tooth injury | | 1 | |
| Investigations | Cardiac murmur | | 1 | |
| | Elevated serum | 1 | | |
| | Hematuria | | 1 | |
| | Hepatic enzyme increase | 2 (1) | 2 | 1 |
| | Hypercalcemia | | 1 | |
| | Hyperkalaemia | 1 | | 1 |
| | Laparoscopy | | | 1 |
| | Leucopenia | | 1 | |
| | Lymph node enlargement | | 1 | |
| | Weight decreased | | | 1 |
| | Weight increased | 1 | | |
| Metabolism and nutritional disorders | Blood glucose fluctuation | | | 1 |
| | Hyperglycemia | 1 (1) | 1 | 1 |
| | Hypoglycemia | 2 (1) | 5 (1) | 5 |
| | Hypoglycemic coma | 2 | 2 | |
| | Hyperlipidemia | 1 | | |
| | Hypothyroidism | | | 1 |
| | Increased appetite | | | 1 |
| | Insulin sensitivity | 1 (1) | | 1 (1) |
| | Vitamin B12 deficiency | | 1 | |
| Musculoskeletal and connective tissue disorder | Arthralgia | 3 | 3 | 6 (1) |
| | Arthritis | 1 | 1 | |
| | Arthropathy | 2 | 1 | 1 |
| | Back pain | | 2 | 4 |
| | Epicondylitis | 1 | 1 | |
| | Exostosis | 2 | | |
| | Muscle spasm | | 1 | |
| | Muscle cramp | 1 | | 1 |
| | Muscular atrophy | | 1 | |
| | Musculoskeletal chest | 1 | | |
| | Myalgia | 3 | 1 | |
| | Pain in extremity | 3 (1) | 4 | 8 (1) |
| | Pain in jaw | | | 1 |
| | Pain in neck | 1 | | 1 |
| | Pain in shoulder | | 1 | |
| | Periarthritis | | | 1 |
| | Synovial disorder | 1 | | |
| | Tendinitis | | 1 | |
| | Tendinous contracture | 1 | | |
| | Tendosynovitis | | 1 | |
| | Torticollis | | 1 | |
| Nervous system disorders | Burning sensation | | 1 | |
| | Carpal tunnel syndrome | 1 | | 1 |
| | Dizziness | 2 | | 1 |
| | Headache | 35 | 17 | 31 (3) |
| | Hyperaesthesia | | 1 (1) | |
| | Hyperthermeasthesia | 2 (2) | | |
| | Hypoaesthesia | 2 | | |
| | Insomnia | | | 1 (1) |
| | Migraine | | 1 | |
| | Multiple sclerosis | 1 | | |
| | Pain in extremity | | | 1 (1) |
| | Paraesthesia | 2 (1) | 2 (2) | 2 (2) |
| | Restless legs syndrome | | 1 | |
| | Sciatica | | 1 | |
| | Sensory loss | | 1 | 2 |
| | Vertigo | | 1 | |
| Pregnancy, puerperium and perinatal conditions | Pregnancy | | 2 | |
| Psychiatric disorders | Depression | 1 | | 1 |
| | Panic disorder | 1 | | |
| | Stress disorder | 1 | | |
| Renal and urinary disorder | Nephritis | | | 1 |
| Reproductive system and breast disorders | Dysmenorrhea | | | 1 |
| | Menopausal disorder | | 1 | 1 |
| | Menstruation irregular | | 1 | 1 |
| Respiratory, thoracic, and mediastinal disorders | Asthma | 1 | | |
| | Cough | | 1 | 1 |
| | Epistaxis | | 1 | 3 |
| Skin and subcutaneous tissue disorders | Dry skin | 1 | | |
| | Fibroma | 1 | | |
| | Skin induration | 2 | 1 | |
| | Skin infection | | 2 | |
| | Sweating increased | | 1 | |
| | Tinea | | | 1 |
| Surgical and Medical | Eye operation | 1 | | |
| | Limb operation | 1 | 1 | |
| | Tooth extraction | | 1 | 1 |
| Vascular disorders | Arterial disorder | | 1 | 1 |
| | Hypertension | 1 | 1 | 1 |
| | Hypotension | | 1 | |
| Total | | 173 (8) | 156 (5) | 166 (12) |

Analysis of Adverse Events

AEs were reported in all but 8 patients in the low-dose C-peptide group, 6 patients in high-dose C-peptide group, and 9 patients in placebo group. A total number of 495 AEs were reported during the study. The numbers of AEs were similar in all dose groups within the different SOCs. The most frequently reported AE was headache, followed by nasopharyngitis, both equally occurring in all dose groups. One-hundred-fifty-five (155) AEs were reported as having moderate intensity (51 in low-dose C-peptide group, 43 in high-dose C-peptide group, and 61 in placebo group) and 12 AEs were reported with severe intensity (1 in low-dose C-peptide group, 9 in high-dose C-peptide group, and 2 in placebo group). A listing of these patients is shown in Table E27.

TABLE E27

Treatment emergent AEs of moderate and severe intensity (ITT data set).
S (Severe), M (Moderate); followed by number of AE incidences in parentheses.

| SOC | Preferred Term | Low-dose C-peptide | High-dose C-peptide | Placebo |
|---|---|---|---|---|
| Cardiac | ST elevation | M (1) | | |
| Eye disorder | Dacryocanaliculitis | M (1) | | |
| | Retinopathy proliferative | | | M (1) |
| | Vitreous | | M (1) | |
| | Vision decreased | M (1) | | |
| Gastrointestinal Disorders | Abdomnial pain | | M (1) | |
| | Celiac disease | M (1) | | |
| | Constipation | | | M (1) |
| | Diarrhea | | S (1) | M (1) |
| | Dysphagia | | | M (1) |
| | Gastritis | | M (1) | |
| | Nausea | M (1) | M (1) | |
| | Toothache | M (1) | M (2) | M (2) |
| General disorders and administration site conditions | Pyrexia | M (1) | | M (2) |
| | Fatigue | | M (1) | |
| | Feeling abnormal | | M (3) | M (1) |
| | Edema peripheral | | | M (1) |
| Infections and infestations | Acute HIV infection | M (1) | | |
| | Borrelia infection | M (1) | | |
| | Bronchitis | M (1) | | |
| | Gastroenteritis | | M (3) | M (1) |
| | Herpes zoster | M (1) | | |
| | Nasopharyngitis | M (6) | M (8) | M (7) |
| | Otitis | M (1) | | |
| | Pharyngitis | S (1) | M (1) | M (3) |
| | Perianal abscess | | | M (1) |
| | Sinusitis | M (4) | M (2) | M (1) |
| | Sepsis | | S (1) | |
| | Tonsillitis | M (1) | | M (1) |
| | Tooth infection | | | M (1) |
| | Urinary tract | | | M (2) |
| Injury poisoning, procedural complications | Alcohol poisoning | | | M (1) |
| | Dizziness | | M (1) | |
| | Knee injury | | M (1) | |
| | Pain in extremity | | | M (1) |
| | Rib fracture/injury | | M (1); S (1) | |
| Investigations | Hepatic enzyme increase | | S (1) | |
| Metabolism and nutritional disorders | Blood glucose fluctuation | | | M (1) |
| | Hyperglycemia | | S (1) | M (1) |
| | Hypoglycemia | M (2) | M (1); S (1) | M (1); S (2) |
| | Hypoglycemic | M (1) | S (2) | |
| | Hyperlipidemia | M (1) | | |
| | Increased appetite | | | M (1) |
| Musculoskeletal and connective tissue dissorder | Arthralgia | M (1) | M (1) | M (2) |
| | Arthritis | M (1) | M (1) | |
| | Arthropathy | M (1) | | |
| | Back pain | | M (1) | M (1) |
| | Epicondylitis | | M (1) | |
| | Muscle cramp | M (1) | | M (1) |
| | Myalgia | M (2) | | |
| | Pain in extremity | | M (2) | M (4) |
| | Pain in neck | | | M (1) |
| | Tendinous | M (1) | | |
| Nervous system disorders | Carpal tunnel syndrome | M (1) | | |
| | Dizziness | M (1) | | |
| | Headache | M (11) | M (3) | M (15) |
| | Migraine | | M (1) | |
| | Paraesthesia | | M (1) | |
| | Restless legs syndrome | | M (1) | |
| | Sciatica | | M (1) | |
| Pregnancy, puerperium and perinatal conditions | Pregnancy | | S (1) | |
| Psychiatric disorders | Depression | M (1) | | M (1) |
| | Stress disorder | M (1) | | |

TABLE E27-continued

Treatment emergent AEs of moderate and severe intensity (ITT data set).
S (Severe), M (Moderate); followed by number of AE incidences in parentheses.

| | | Treatment | | |
| --- | --- | --- | --- | --- |
| SOC | Preferred Term | Low-dose C-peptide | High-dose C-peptide | Placebo |
| Renal and urinary disorder | Nephritis | | | M (1) |
| Respiratory, thoracic and mediastinal disorders | Epistaxis | | | M (1) |
| Skin and subcutaneous tissue disorders | Skin infection | M (1) | | |
| Surgical and Medical | Limb operation | M (1) | M (1) | |
| | Tooth extraction | | | M (1) |
| Vascular disorders | Hypotension | | M (1) | |
| Total Adverse Events | | Moderate = 51 Severe = 1 | Moderate = 43 Severe = 9 | Moderate = 61 Severe = 2 |

Twenty-five (25) AEs (8 in low-dose C-peptide group, 5 in high-dose C-peptide group and 12 in placebo group) spread on different AE diagnosis, were in the opinion of the investigators reported as possibly/probably related to the study drug.

Hypoglycemic events were noted by the patient and were not reported as AEs, unless the severity of the event required assistance by another person or else in the opinion of investigator it should be reported as an AE. There were 14 treatment emergent symptomatic hypoglycemic episodes and two hypoglycemic coma episodes requiring external assistance.

Deaths, Other Serious Adverse Events, and Other Significant Adverse Events

There were no deaths in this trial. Two SAEs occurred during the study.

Analysis and Discussion of Deaths, Other Serious Adverse Events, and Other Significant Adverse Events Two SAEs occurred during the study, both patients were treated with high-dose C-peptide (1,500 nmoL/24 h). The assessments of the events relationship to the trial medication were by the investigators at both sites "unlikely/not related".

Clinical Laboratory Evaluation

There were generally very few deviations outside the normal range in most of the laboratory tests and when observed most of them were of minor clinical significance. Following the study treatment there were few shifts from normal to abnormal and there were no significant changes in any of the variables.

Vital Signs, Physical Findings, and Other Observations to Safety

There were no clinically significant abnormalities in ECG reported during the study medication treatment, nor were there any significant changes in heart rate, blood pressure, and QTc in any of the three treatment groups (Table E25).

Safety Conclusions

C-peptide was well tolerated in the doses of 500-1,500 nmoL/24 h and no adverse drug reactions or significant changes in safety variables (blood chemistries and vital signs) were observed during the study period. No local reactions were reported.

V. Discussion And Overall Conclusions

Overall Conclusions

Neuropathy

It is concluded that C-peptide given in a therapeutic dose for 6 months was well tolerated and had a beneficial effect on nerve function in patients with early stage neuropathy. Thus, C-peptide used as a complement to regular insulin therapy may provide an effective approach to the management of the long-term complications of type 1 diabetes such as neuropathy.

The primary variable in the present study, sensory nerve conduction velocity (SNCV), improved significantly within the group of patients receiving active treatment, but the difference in SNCV response after C-peptide therapy versus placebo treatment did not attain statistical significance. Consequently, the study did not meet its primary end point. However, further statistical analyses show that there were significantly more "responders" in the C-peptide-treated groups compared to the placebo group (p<0.03), responders being defined as patients with an improvement in SNCV greater than 1 m/s, an increase recognized by the DCCT study to be of clinical significance. In view of the exploratory nature of this trial, the result of the responder analysis can be viewed as a positive study outcome.

Subgroups

A subgroup of the patients was subjected to further statistical analysis. Thus, in the half of the patient group that showed the less severe nerve dysfunction (n=70), as evaluated from the degree of SNCV reduction at baseline, there was significant improvement in SNCV within the C-peptide treated group. In the corresponding placebo group there was minimal change in SNCV compared to baseline, and the improvement in the C-peptide groups was significantly greater than that in the placebo group. Moreover, analysis of the responders in this subgroup again demonstrated a significantly greater number of responders in the patients on active treatment compared to placebo. These findings confirm and extend the results from a previous 3-month phase II trial in which type 1 diabetes patients with early stage (sub-clinical)

neuropathy were found to markedly improve their SNCV during C-peptide replacement therapy. The findings suggest that the beneficial effect of C-peptide—at least in studies with 3-6 months duration—is most pronounced in the less diseased patients, emphasizing the need for early intervention in this disorder.

Insulin Requirements

Insulin use could be evaluated in approximately one-fourth of the patients, and within this group, several patients reported having modified their insulin dose during the course of the trial. Significantly more patients stated that they had reduced their insulin dose among the C-peptide-treated patients compared to placebo, especially in the high-dose C-peptide group.

The observation of reduced long-term insulin usage in the present trial was unexpected, and surprising. Indeed, although some studies have indicated that C-peptide and insulin may interact synergistically on the insulin signalling pathway, this is an effect that appears to be limited to situations when the insulin and C-peptide are co-administered at the same site (Shafqat et al.: Cell. Mol. Life. Sci. 63: 1805-1811, (2006)) and is believed to be due to the dispersal of zinc insulin hexamers via C-peptide.

Such an effect was not expected in the present study, because patients injected insulin and C-peptide at opposite sides of their abdomens (see "Duration of treatment and site of injection",). Thus C-peptide would never be present at a high enough local concentration to directly impact the hexameric state of injected insulin. Thus, this observation represents the first time a sustained reduction in long-term requirements for insulin usage has been reported in clinical reports with C-peptide administered via S.C. injection.

Hypoglycemia

The identification of sustained reduction in insulin requirements in the present study has ramifications for the development of effective and safe C-peptide replacement therapies for the treatment of the long-term complications of diabetes. Specifically this discovery highlights the need to carefully monitor a patient's insulin requirements, and susceptibility to hypoglycemia when initiating C-peptide therapy, so as to reduce the risk of the patient developing hypoglycemia and hypoglycemic coma. This study represents a well-controlled environment with very carefully monitored patients. In spite of this oversight and support, and the context of a self-reported reduction in insulin usage with some patients, there were four cases of hypoglycemic coma, all in the treated group. Two of the hypoglycemic coma episodes required external assistance. These observations are consistent with the hypothesis that the management of insulin dosage is more challenging upon initiating C-peptide therapy and in some patients requires lowering of the insulin dosage to avoid serious hypoglycemic events, including coma. Additionally this discovery makes possible the development of new dosing regimens with C-peptide together with insulin that provide for improved glycemic control, effective treatment of the long-term complications of diabetes, and reduce or eliminate unwanted weight gain through reduction in insulin usage.

REFERENCES FOR EXAMPLES SECTION

American Diabetes Association and American Academy of Neurology (1988). Report and recommendation of the San Antonio Conference on Diabetic Neuropathy (consensus statement). Diabetes Care 11: 592-597.

Dalla Vestra, M., A. Saller, E. Bortoloso, M. Mauer and P. Fioretto (2000). Structural involvement in type 1 and type 2 diabetic nephropathy. Diabetes Metab 26 (suppl 4): 8-14.

DCCT Group (1993). The effect of intensive treatment of diabetes on the development and progression of long-term complications in insulin-dependent diabetes mellitus. New Engl J. Med. 329: 977-983.

DCCT Group (1995a). Effect of intensive diabetes treatment on nerve conduction in the diabetes control and complications trial. Ann Neurol 38: 869-880.

DCCT Group (1995b). Effect of intensive therapy on the development and progression of diabetic nephropathy in the Diabetes Control and Complications Trial. The Diabetes Control and Complications (DCCT) Research Group. Kidney Int 47(6): 1703-1720.

Ekberg, K., T. Brismar, B.-L. Johansson, et al. (2003). Amelioration of sensory nerve dysfunction by C-peptide in patients with type 1 diabetes. Diabetes 52: 536-541.

Forst, T., T. Kunt, T. Pohlmann, et al. (1998). Biological activity of C-peptide on the skin microcirculation in patients with insulin dependent diabetes mellitus. J. Clin. Invest. 101: 2036-2041.

Hansen, A., B.-L. Johansson, J. Wahren and H. Bibra von (2002). C-peptide exerts beneficial effects on myocardial blood flow and function in patients with type 1 diabetes. Diabetes 51(10): 3077-3082.

Johansson, B.-L., K. Borg, E. Fernqvist-Forbes, et al. (2000). Beneficial effects of C-peptide on incipient nephropathy and neuropathy in patients with type I diabetes. Diabetic Medicine 17(3): 181-189.

Johansson, B.-L., K. Borg, E. Fernqvist-Forbes, et al. (1996). C-peptide improves autonomic nerve function IDDM patients. Diabetologia 39: 687-695.

Johansson, B.-L., B. Linde and J. Wahren (1992a). Effects of C-peptide on blood flow, capillary diffusion capacity and glucose utilization in the exercising forearm of Type I (insulin-dependent) diabetic patients. Diabetologia 35: 1151-1158.

Johansson, B.-L., S. Sjöberg and J. Wahren (1992b). The influence of human C-peptide on renal function and glucose utilization in Type I (insulin-dependent) diabetic patients. Diabetologia 35: 121-128.

Johansson, B.-L., J. Sundell, K. Ekberg, et al. (2004). C-peptide improves adenosine-induced myocardial vasodilation in type 1 diabetes patients. Am J Physiol Endocrinol Metab 286(1): E14-E19.

Kitamura, T., K. Kimura, K. Makondo, et al. (2003). Proinsulin C-peptide increases nitric oxide production by enhancing mitogen-activated protein-kinase-dependent transcription of endothelial nitric oxide synthase in aortic endothelial cells of Wistar rats. Diabetologia 46(12): 1698-1705.

Ohtomo, Y., A. Aperia, B. Sahlgren, B.-L. Johansson and J. Wahren (1996). C-peptide stimulates rat renal tubular $Na^+$, $K^+$-ATPase activity in synergism with neuropeptide Y. Diabetologia 39: 199-205.

Polonsky, K., B. Given and E. van Cauter (1988). Twenty-four-hour profiles and pulsatile patterns of insulin secretion in normal and obese subjects. J. Clin. Invest. 81: 442-448.

Rigler, R., A. Pramanik, P. Jonasson, et al. (1999). Specific binding of proinsulin C-peptide to human cell membranes. Proc Natl Acad Sci USA 96: 13318-13323.

Shafqat, J., L. Juntti-Berggren, Z. Zhong, et al. (2002). Proinsulin C-peptide and its analogues induce intracellular $Ca^{2+}$ increases in human renal tubular cells. Cell Mol Life Sci 59: 1185-1189.

Sima, A. A. and K. Sugimoto (1999). Experimental diabetic neuropathy: an update. Diabetologia 42: 773-788.

Sima, A. A., W. Zhang, K. Sugimoto, et al. (2001). C-peptide prevents and improves chronic type 1 diabetic polyneuropathy in the BB/Wor rat. Diabetologia 44: 889-897.

Sundkvist, G., L. Almer and B. Lilja (1979). Respiratory influence on heart rate in diabetes mellitus. Br Med J 1(6168): 924-925.

Wahren, J., K. Ekberg, J. Johansson, et al. (2000). Role of C-peptide in human physiology. Am J Physiol Endocrinol Metab 278: E759-E768.

Wallerath, T., T. Kunt, T. Forst, et al. (2003). Stimulation of endothelial nitric oxide synthase by proinsulin C-peptide. Nitric Oxide 9: 95-102.

Zhong, Z., A. Davidescu, I. Ehron, et al. (2005). C-peptide stimulates ERK1/2 and JNK MAP-kinases via activation of PKC in human renal tubular cells. Diabetelogia 48: 187-197.

Zhong, Z., O. Kotova, A. Davidescu, et al. (2004). C-peptide stimulates Na+,K+-ATPase via activation of ERK1/2 MAP kinases in human renal tubular cells. Cell Mol Life Sci 61: 2782-2790.

SEQ. ID. No. 1

Type: Protein

Organism: Homo sapiens

EAEDLQVGQVELGGGPGAGSLQPLALEGSLQ
SEQ. ID. No. 2

Type: Protein

Organism: Pan troglodytes

EAEDLQVGQVELGGGPGAGSLQPLALEGSLQ
SEQ. ID. No. 3

Type: Protein

Organism: Gorilla gorilla

EAEDLQVGQVELGGGPGAGSLQPLALEGSLQ
SEQ. ID. No. 4

Type: Protein

Organism: Pongo pygmaeus

EAEDLQVGQVELGGGPGAGSLQPLALEGSLQ
SEQ. ID. No. 5

Type: Protein

Organism: Chiorocebus aethiops

EAEDPQVGQVELGGGPGAGSLQPLALEGSLQ
SEQ. ID. No. 6

Type: Protein

Organism: Canis lupus familiaris

EVEDLQVRDVELAGAPGEGGLQPLALEGALQ
SEQ. ID. No. 7

Type: Protein

Organism: Oryctolagus cuniculus

EVEELQVGQAELGGGPDAGGLQPSALELALQ
SEQ. ID. No. 8

Type: Protein

Organism: Rattus norvegicus

EVEDPQVAQLELGGGPGAGDLQTLALEVARQ
SEQ. ID. No. 9

Type: Protein

Organism: Apodemus semotus

EVEDPQVAQLELGGGPGAGDLQTLALEVARQ
SEQ. ID. No. 10

Type: Protein

Organism: Geodia cydonium

EVEDPQVGQVELGAGPGAGSEQTLALEVARQ
SEQ. ID. No. 11

Type: Protein

Organism: Mus musculus

EVEDPQVAQLELGGGPGAGDLQTLALE
SEQ. ID. No. 12

Type: Protein

Organism: Mus caroli

EVEDPQVAQLELGGGPGAGDLQTLALE
SEQ. ID. No. 13

Type: Protein

Organism: Rattus norvegicus

EVEDPQVPQLELGGGPGAGDLQTLALEVARQ
SEQ. ID. No. 14

Type: Protein

Organism: Rattus losea

EVEDPQVAQQELGGGPGAGDLQTLALEVARQ
SEQ. ID. No. 15

Type: Protein

Organism: Niviventer coxingi

EVEDPQVPQLELGGGPGTGDLQTLALEVARQ
SEQ. ID. No. 16

Type: Protein

Organism: Microtus kikuchii

VEDPQVAQLELGGGPGAGDLQTLALE
SEQ. ID. No. 17

Type: Protein

Organism: Rattus norvegicus

EVEDPQVPQLELGGGPEAGDLQTLALEVARQ
SEQ. ID. No. 18

Type: Protein

Organism: Felis catus

EAEDLQGKDAELGEAPGAGGLQPSALEAPLQ
SEQ. ID. No. 19

Type: Protein

Organism: Mesocricetus auratus

VEDPQVAQLELGGGPGADDLQTLALE
SEQ. ID. No. 20

Type: Protein

Organism: Niviventer coxingi

EVEDPQVAQLELGEGPEAGDLQTLALEVARQ
SEQ. ID. No. 21

Type: Protein

Organism: Apodemus semotus

EVEDPQVEQLELGGAPGTGDLETLALEVARQ
SEQ. ID. No. 22

Type: Protein

Organism: Rattus losea

EVEDPQVPQLELGGSPEAGDLQTLALEVARQ
SEQ. ID. No. 23

Type: Protein

Organism: Meriones unguiculatus

VEDPQMPQLELGGSPGAGDLQALALEVARQ
SEQ. ID. No. 24

Type: Protein

Organism: Psammomys obesus

VDDPQMPQLELGGSPGAGDLRALALEVARQ
SEQ. ID. No. 25

Type: Protein

Organism: Sus scrofa

EAENPQAGAVELGGGLGGLQALALEG
SEQ. ID. No. 26

Type: Protein

Organism: Rhinolophus ferrumequinum

EVEDPQAGQVELGGGPGTGGLQSLALEGPPQ
SEQ. ID. No. 27

Type: Protein

Organism: Equus przewalskii

EAEDPQVGEVELGGGPGLGGLQPLALAGPQQ
SEQ. ID. No. 28

Type: Protein

Organism: Bos Taurus

EVEGPQVGALELAGGPGAGGLEGPPQ
SEQ. ID. No. 29

Type: Protein

Organism: Otolemur garnettii

DTEDPQVGQVGLGGSPITGDLQSLALDVPPQ
SEQ. ID. No. 30

Type: Protein

Organism: Artificial Sequence

EXEXXQXXXXELXXXXXXXXXXXXALBXXXQ
SEQ. ID. No. 31

Type: Protein

Organism: Artificial Sequence

EGSLQ
SEQ. ID. No. 32

Type: Protein

Organism: Artificial Sequence

EAEDLQVGQVEL
SEQ. ID. No. 33

Type: Protein

Organism: Artificial Sequence

GXEXXQXXXXELXXXXXXXXXXXXALBXXXQ

---

We claim:

1. A method for treating an insulin-dependent human patient, comprising the steps of:
   a. administering insulin to said patient, wherein said patient has neuropathy;
   b. administering subcutaneously to said patient a therapeutic dose of C-peptide in a different site as that used for said patient's insulin administration;
   c. adjusting the dosage amount, type, or frequency of insulin administered based on monitoring said patient's altered insulin requirements resulting from said therapeutic dose of C-peptide, wherein said adjusted dose of insulin reduces the risk, incidence, or severity of hypoglycemia, wherein said adjusted dose of insulin is at least 10% less than said patient's insulin dose prior to starting C-peptide treatment.

2. The method of claim 1, wherein said patient has established neuropathy.

3. The method of claim 1, wherein said patient is being treated for a long-term complication of type 1 diabetes.

4. The method of claim 1, wherein the hypoglycemia is severe hypoglycemia.

5. The method of claim 1, wherein the hypoglycemia is asymptomatic hypoglycemia.

6. The method of claim 1 wherein said therapeutic dose of C-peptide is from about 1.5 mg to about 4.5 mg/24 hours.

7. The method of claim 1, wherein said administration of C-peptide is via a sustained release composition or device.

8. The method of claim 1, wherein said adjusted dose of insulin is at about 10% to about 35% less than said patient's insulin dose prior to starting C-peptide treatment.

9. The method of claim 1, wherein said therapeutic dose of C-peptide has been administered to said patient for at least one week prior to step c of claim 1.

10. The method of claim 1, wherein said patient has type 1.5 diabetes.

11. The method of claim 1, wherein said therapeutic dose of C-peptide maintains an average steady state concentration of C-peptide ($C_{ss\text{-}ave}$) in said patient's plasma of between about 0.2 nM and about 6 nM.

12. A method of reducing insulin usage in an insulin-dependent human patient, comprising the steps of:
   a. administering insulin to said patient, wherein said patient has neuropathy;
   b. administering subcutaneously to said patient a therapeutic dose of C-peptide in a different site as that used for said patient's insulin administration;
   c. adjusting the dosage amount, type, or frequency of insulin administered based on monitoring said patient's altered insulin requirements resulting from said therapeutic dose of C-peptide, wherein said adjusted dose of insulin does not induce hypoglycemia, wherein said adjusted dose of insulin is at least 10% less than said patient's insulin dose prior to starting C-peptide treatment.

13. The method of claim 12, wherein said patient has established neuropathy.

14. The method of claim 12, wherein said patient is being treated for a long-term complication of type 1 diabetes.

15. The method of claim 12, wherein said therapeutic dose of C-peptide is from about 1.5 mg to about 4.5 mg/24 hours.

16. The method of claim 12, wherein said therapeutic dose of C-peptide has been administered to said patient for at least one week prior to step c of claim 12.

17. The method of claim 12, wherein said adjusted dose of insulin is about 10% to about 35% less than said patient's insulin dose prior to starting C-peptide treatment.

18. The method of claim 12, wherein said patient has type 1.5 diabetes.

19. The method of claim 12, wherein said therapeutic dose of C-peptide maintains an average steady state concentration of C-peptide ($C_{ss\text{-}ave}$) in said patient's plasma of between about 0.2 nM and about 6 nM.

20. The method of claim 12, wherein said monitoring is conducted over an evaluation period of about two weeks after starting C-peptide therapy.

* * * * *

UNITED STATES PATENT AND TRADEMARK OFFICE
CERTIFICATE OF CORRECTION

PATENT NO. : 7,855,177 B1  
APPLICATION NO. : 12/796149  
DATED : December 21, 2010  
INVENTOR(S) : John Wahren et al.

It is certified that error appears in the above-identified patent and that said Letters Patent is hereby corrected as shown below:

On the title page, under Related U.S. Application Data, item [63] the following information should be inserted after item [60] Provisional Application No. 61/255,560, filed on October 28, 2009.

--U.S. Non-Provisional Application Serial No. 12/717,794, filed on Mar. 4, 2010--

Signed and Sealed this
Twenty-first Day of October, 2014

Michelle K. Lee
*Deputy Director of the United States Patent and Trademark Office*

SEQUENCE LISTING

```
<160> NUMBER OF SEQ ID NOS: 33

<210> SEQ ID NO 1
<211> LENGTH: 31
<212> TYPE: PRT
<213> ORGANISM: Homo sapiens

<400> SEQUENCE: 1

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 2
<211> LENGTH: 31
<212> TYPE: PRT
<213> ORGANISM: Pan troglodytes

<400> SEQUENCE: 2

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 3
```

```
<211> LENGTH: 31
<212> TYPE: PRT
<213> ORGANISM: Gorilla gorilla

<400> SEQUENCE: 3

Glu Ala Glu Asp Leu Gln Val Gly Gln Val Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 4
<211> LENGTH: 31
<212> TYPE: PRT
<213> ORGANISM: Pongo pygmaeus

<400> SEQUENCE: 4

Glu Ala Glu Asp Leu Gln Val Gly Gln Val Glu Leu Gly Gly Pro
1               5                   10                  15

Gly Ala Gly Ser Leu Gln Pro Leu Ala Leu Glu Gly Ser Leu Gln
            20                  25                  30

<210> SEQ ID NO 5
<211> LENGTH: 31
<212> TYPE: PRT
<213> ORGANISM: Chlorocebus aethiops

<400> SEQUENCE: 5

Glu Ala Glu Asp Pro Gln Val Gly Gln Val Glu Leu Gly Gly Pro
1               5                   10                  15

Gly Ala Gly Ser Leu Gln Pro Leu Ala Leu Glu Gly Ser Leu Gln
            20                  25                  30

<210> SEQ ID NO 6
<211> LENGTH: 31
<212> TYPE: PRT
<213> ORGANISM: Canis lupus familiaris

<400> SEQUENCE: 6

Glu Val Glu Asp Leu Gln Val Arg Asp Val Glu Leu Ala Gly Ala Pro
1               5                   10                  15

Gly Glu Gly Gly Leu Gln Pro Leu Ala Leu Glu Gly Ala Leu Gln
            20                  25                  30

<210> SEQ ID NO 7
<211> LENGTH: 31
<212> TYPE: PRT
<213> ORGANISM: Oryctolagus cuniculus

<400> SEQUENCE: 7

Glu Val Glu Glu Leu Gln Val Gly Gln Ala Glu Leu Gly Gly Pro
1               5                   10                  15

Asp Ala Gly Gly Leu Gln Pro Ser Ala Leu Glu Leu Ala Leu Gln
            20                  25                  30

<210> SEQ ID NO 8
<211> LENGTH: 31
<212> TYPE: PRT
<213> ORGANISM: Rattus norvegicus

<400> SEQUENCE: 8

Glu Val Glu Asp Pro Gln Val Ala Gln Leu Glu Leu Gly Gly Gly Pro
1               5                   10                  15
```

-continued

Gly Ala Gly Asp Leu Gln Thr Leu Ala Leu Glu Val Ala Arg Gln
            20                  25                  30

<210> SEQ ID NO 9
<211> LENGTH: 31
<212> TYPE: PRT
<213> ORGANISM: Apodemus semotus

<400> SEQUENCE: 9

Glu Val Glu Asp Pro Gln Val Ala Gln Leu Glu Leu Gly Gly Gly Pro
1               5                   10                  15

Gly Ala Gly Asp Leu Gln Thr Leu Ala Leu Glu Val Ala Arg Gln
            20                  25                  30

<210> SEQ ID NO 10
<211> LENGTH: 31
<212> TYPE: PRT
<213> ORGANISM: Geodia cydonium

<400> SEQUENCE: 10

Glu Val Glu Asp Pro Gln Val Gly Gln Val Glu Leu Gly Ala Gly Pro
1               5                   10                  15

Gly Ala Gly Ser Glu Gln Thr Leu Ala Leu Glu Val Ala Arg Gln
            20                  25                  30

<210> SEQ ID NO 11
<211> LENGTH: 27
<212> TYPE: PRT
<213> ORGANISM: Mus musculus

<400> SEQUENCE: 11

Glu Val Glu Asp Pro Gln Val Ala Gln Leu Glu Leu Gly Gly Gly Pro
1               5                   10                  15

Gly Ala Gly Asp Leu Gln Thr Leu Ala Leu Glu
            20                  25

<210> SEQ ID NO 12
<211> LENGTH: 27
<212> TYPE: PRT
<213> ORGANISM: Mus caroli

<400> SEQUENCE: 12

Glu Val Glu Asp Pro Gln Val Ala Gln Leu Glu Leu Gly Gly Gly Pro
1               5                   10                  15

Gly Ala Gly Asp Leu Gln Thr Leu Ala Leu Glu
            20                  25

<210> SEQ ID NO 13
<211> LENGTH: 31
<212> TYPE: PRT
<213> ORGANISM: Rattus norvegicus

<400> SEQUENCE: 13

Glu Val Glu Asp Pro Gln Val Pro Gln Leu Glu Leu Gly Gly Gly Pro
1               5                   10                  15

Gly Ala Gly Asp Leu Gln Thr Leu Ala Leu Glu Val Ala Arg Gln
            20                  25                  30

<210> SEQ ID NO 14
<211> LENGTH: 31
<212> TYPE: PRT
<213> ORGANISM: Rattus losea -continued

<400> SEQUENCE: 14

Glu Val Glu Asp Pro Gln Val Ala Gln Gln Leu Gly Gly Gly Pro
1               5                   10                  15

Gly Ala Gly Asp Leu Gln Thr Leu Ala Leu Glu Val Ala Arg Gln
            20                  25                  30

<210> SEQ ID NO 15
<211> LENGTH: 31
<212> TYPE: PRT
<213> ORGANISM: Niviventer coxingi

<400> SEQUENCE: 15

Glu Val Glu Asp Pro Gln Val Pro Gln Leu Glu Leu Gly Gly Pro
1               5                   10                  15

Gly Thr Gly Asp Leu Gln Thr Leu Ala Leu Glu Val Ala Arg Gln
            20                  25                  30

<210> SEQ ID NO 16
<211> LENGTH: 26
<212> TYPE: PRT
<213> ORGANISM: Microtus kikuchii

<400> SEQUENCE: 16

Val Glu Asp Pro Gln Val Ala Gln Leu Glu Leu Gly Gly Gly Pro Gly
1               5                   10                  15

Ala Gly Asp Leu Gln Thr Leu Ala Leu Glu
            20                  25

<210> SEQ ID NO 17
<211> LENGTH: 31
<212> TYPE: PRT
<213> ORGANISM: Rattus norvegicus

<400> SEQUENCE: 17

Glu Val Glu Asp Pro Gln Val Pro Gln Leu Glu Leu Gly Gly Gly Pro
1               5                   10                  15

Glu Ala Gly Asp Leu Gln Thr Leu Ala Leu Glu Val Ala Arg Gln
            20                  25                  30

<210> SEQ ID NO 18
<211> LENGTH: 31
<212> TYPE: PRT
<213> ORGANISM: Felis catus

<400> SEQUENCE: 18

Glu Ala Glu Asp Leu Gln Gly Lys Asp Ala Glu Leu Gly Glu Ala Pro
1               5                   10                  15

Gly Ala Gly Gly Leu Gln Pro Ser Ala Leu Glu Ala Pro Leu Gln
            20                  25                  30

<210> SEQ ID NO 19
<211> LENGTH: 26
<212> TYPE: PRT
<213> ORGANISM: Mesocricetus auratus

<400> SEQUENCE: 19

Val Glu Asp Pro Gln Val Ala Gln Leu Glu Leu Gly Gly Gly Pro Gly
1               5                   10                  15

Ala Asp Asp Leu Gln Thr Leu Ala Leu Glu
            20                  25

```
<210> SEQ ID NO 20
<211> LENGTH: 31
<212> TYPE: PRT
<213> ORGANISM: Niviventer coxingi

<400> SEQUENCE: 20

Glu Val Glu Asp Pro Gln Val Ala Gln Leu Glu Leu Gly Glu Gly Pro
1               5                   10                  15

Glu Ala Gly Asp Leu Gln Thr Leu Ala Leu Glu Val Ala Arg Gln
            20                  25                  30

<210> SEQ ID NO 21
<211> LENGTH: 31
<212> TYPE: PRT
<213> ORGANISM: Apodemus semotus

<400> SEQUENCE: 21

Glu Val Glu Asp Pro Gln Val Glu Gln Leu Glu Leu Gly Gly Ala Pro
1               5                   10                  15

Gly Thr Gly Asp Leu Glu Thr Leu Ala Leu Glu Val Ala Arg Gln
            20                  25                  30

<210> SEQ ID NO 22
<211> LENGTH: 31
<212> TYPE: PRT
<213> ORGANISM: Rattus losea

<400> SEQUENCE: 22

Glu Val Glu Asp Pro Gln Val Pro Gln Leu Glu Leu Gly Gly Ser Pro
1               5                   10                  15

Glu Ala Gly Asp Leu Gln Thr Leu Ala Leu Glu Val Ala Arg Gln
            20                  25                  30

<210> SEQ ID NO 23
<211> LENGTH: 30
<212> TYPE: PRT
<213> ORGANISM: Meriones unguiculatus

<400> SEQUENCE: 23

Val Glu Asp Pro Gln Met Pro Gln Leu Glu Leu Gly Gly Ser Pro Gly
1               5                   10                  15

Ala Gly Asp Leu Gln Ala Leu Ala Leu Glu Val Ala Arg Gln
            20                  25                  30

<210> SEQ ID NO 24
<211> LENGTH: 30
<212> TYPE: PRT
<213> ORGANISM: Psammomys obesus

<400> SEQUENCE: 24

Val Asp Asp Pro Gln Met Pro Gln Leu Glu Leu Gly Gly Ser Pro Gly
1               5                   10                  15

Ala Gly Asp Leu Arg Ala Leu Ala Leu Glu Val Ala Arg Gln
            20                  25                  30

<210> SEQ ID NO 25
<211> LENGTH: 26
<212> TYPE: PRT
<213> ORGANISM: Sus scrofa

<400> SEQUENCE: 25

Glu Ala Glu Asn Pro Gln Ala Gly Ala Val Glu Leu Gly Gly Gly Leu
1               5                   10                  15
```

-continued

Gly Gly Leu Gln Ala Leu Ala Leu Glu Gly
            20                  25

<210> SEQ ID NO 26
<211> LENGTH: 31
<212> TYPE: PRT
<213> ORGANISM: Rhinolophus ferrumequinum

<400> SEQUENCE: 26

Glu Val Glu Asp Pro Gln Ala Gly Gln Val Glu Leu Gly Gly Gly Pro
1               5                   10                  15

Gly Thr Gly Gly Leu Gln Ser Leu Ala Leu Glu Gly Pro Pro Gln
            20                  25                  30

<210> SEQ ID NO 27
<211> LENGTH: 31
<212> TYPE: PRT
<213> ORGANISM: Equus przewalskii

<400> SEQUENCE: 27

Glu Ala Glu Asp Pro Gln Val Gly Glu Val Glu Leu Gly Gly Gly Pro
1               5                   10                  15

Gly Leu Gly Gly Leu Gln Pro Leu Ala Leu Gly Pro Gln Gln
            20                  25                  30

<210> SEQ ID NO 28
<211> LENGTH: 26
<212> TYPE: PRT
<213> ORGANISM: Bos taurus

<400> SEQUENCE: 28

Glu Val Glu Gly Pro Gln Val Gly Ala Leu Glu Leu Ala Gly Gly Pro
1               5                   10                  15

Gly Ala Gly Gly Leu Glu Gly Pro Pro Gln
            20                  25

<210> SEQ ID NO 29
<211> LENGTH: 31
<212> TYPE: PRT
<213> ORGANISM: Otolemur garnettii

<400> SEQUENCE: 29

Asp Thr Glu Asp Pro Gln Val Gly Gln Val Gly Leu Gly Gly Ser Pro
1               5                   10                  15

Ile Thr Gly Asp Leu Gln Ser Leu Ala Leu Asp Val Pro Pro Gln
            20                  25                  30

<210> SEQ ID NO 30
<211> LENGTH: 31
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(10)
<223> OTHER INFORMATION: Xaa can be any naturally occurring amino acid

```
<220> FEATURE:
<221> NAME/KEY: misc_feature
<222> LOCATION: (13)..(24)
<223> OTHER INFORMATION: Xaa can be any naturally occurring amino acid
<220> FEATURE:
<221> NAME/KEY: misc_feature
<222> LOCATION: (28)..(30)
<223> OTHER INFORMATION: Xaa can be any naturally occurring amino acid

<400> SEQUENCE: 30

Glu Xaa Glu Xaa Xaa Gln Xaa Xaa Xaa Xaa Glu Leu Xaa Xaa Xaa Xaa
1               5                   10                  15

Xaa Xaa Xaa Xaa Xaa Xaa Xaa Xaa Ala Leu Asx Xaa Xaa Xaa Gln
            20                  25                  30

<210> SEQ ID NO 31
<211> LENGTH: 5
<212> TYPE: PRT
<213> ORGANISM: Artificial Sequence
<220> FEATURE:
<223> OTHER INFORMATION: Synthesized

<400> SEQUENCE: 31

Glu Gly Ser Leu Gln
1               5

<210> SEQ ID NO 32
<211> LENGTH: 12
<212> TYPE: PRT
<213> ORGANISM: Artificial Sequence
<220> FEATURE:
<223> OTHER INFORMATION: Synthesized

<400> SEQUENCE: 32

Glu Ala Glu Asp Leu Gln Val Gly Gln Val Glu Leu
1               5                   10

<210> SEQ ID NO 33
<211> LENGTH: 31
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(10)
<223> OTHER INFORMATION: Xaa can be any naturally occurring amino acid
<220> FEATURE:
<221> NAME/KEY: misc_feature
<222> LOCATION: (13)..(24)
<223> OTHER INFORMATION: Xaa can be any naturally occurring amino acid
<220> FEATURE:
<221> NAME/KEY: misc_feature
<222> LOCATION: (28)..(30)
<223> OTHER INFORMATION: Xaa can be any naturally occurring amino acid

<400> SEQUENCE: 33

Gly Xaa Glu Xaa Xaa Gln Xaa Xaa Xaa Xaa Glu Leu Xaa Xaa Xaa Xaa
1               5                   10                  15

Xaa Xaa Xaa Xaa Xaa Xaa Xaa Xaa Ala Leu Asx Xaa Xaa Xaa Gln
            20                  25                  30
```